(12) United States Patent
Bong et al.

(10) Patent No.: US 9,029,112 B2
(45) Date of Patent: May 12, 2015

(54) KETOREDUCTASE-MEDIATED STEREOSELECTIVE ROUTE TO ALPHA CHLOROALCOHOLS

(71) Applicant: Codexis, Inc., Redwood City, CA (US)

(72) Inventors: Yong Koy Bong, Singapore (SG); Michael Vogel, Rhauderfehn (DE); Steven J. Collier, Concord, MA (US); Vesna Mitchell, San Jose, CA (US); Jagadeesh Mavinahalli, Maharashtra (IN)

(73) Assignee: Codexis, Inc., Redwood City, CA (US)

( * ) Notice: Subject to any disclaimer, the term of this patent is extended or adjusted under 35 U.S.C. 154(b) by 0 days.

(21) Appl. No.: 14/313,465

(22) Filed: Jun. 24, 2014

(65) Prior Publication Data

US 2014/0308732 A1 Oct. 16, 2014

Related U.S. Application Data

(62) Division of application No. 13/378,618, filed as application No. PCT/US2010/039511 on Jun. 22, 2010, now Pat. No. 8,796,002.

(60) Provisional application No. 61/303,057, filed on Feb. 10, 2010, provisional application No. 61/219,162, filed on Jun. 22, 2009.

(51) Int. Cl.
| | |
|---|---|
| *C07H 21/00* | (2006.01) |
| *C12N 15/00* | (2006.01) |
| *C12N 5/10* | (2006.01) |
| *C12N 1/21* | (2006.01) |
| *C12P 21/00* | (2006.01) |
| *C12P 7/28* | (2006.01) |
| *C12P 13/02* | (2006.01) |
| *C12P 17/02* | (2006.01) |
| *C12N 9/04* | (2006.01) |
| *C12N 9/02* | (2006.01) |

(52) U.S. Cl.
CPC ............ *C12N 9/0008* (2013.01); *C12N 9/0006* (2013.01); *C12P 7/28* (2013.01); *C12P 13/02* (2013.01); *C12P 17/02* (2013.01)

(58) Field of Classification Search
USPC .......... 435/190, 189, 320.1, 69.1, 325, 252.3; 536/23.2
See application file for complete search history.

(56) References Cited

U.S. PATENT DOCUMENTS

| | | | |
|---|---|---|---|
| 5,559,030 | A | 9/1996 | Matsuyama et al. |
| 5,700,670 | A | 12/1997 | Yamagishi et al. |
| 5,891,685 | A | 4/1999 | Yamagishi et al. |
| 6,399,339 | B1 | 6/2002 | Wolberg et al. |
| 6,645,746 | B1 | 11/2003 | Kizaki et al. |
| 6,800,477 | B2 | 10/2004 | Patel et al. |
| 7,083,973 | B2 | 8/2006 | Patel et al. |
| 7,582,468 | B2 | 9/2009 | Bowers et al. |
| 7,794,993 | B2 | 9/2010 | Kizaki et al. |
| 7,915,022 | B2 | 3/2011 | Kizaki et al. |
| 2006/0286646 | A1 | 12/2006 | Patel et al. |
| 2008/0206826 | A1 | 8/2008 | Meudt et al. |
| 2010/0248317 | A1 | 9/2010 | Gupta et al. |

FOREIGN PATENT DOCUMENTS

| | | |
|---|---|---|
| WO | 9522625 A1 | 8/1995 |
| WO | 9720078 A1 | 6/1997 |
| WO | 9735966 A1 | 10/1997 |
| WO | 9827230 A1 | 6/1998 |
| WO | 0107567 A1 | 2/2001 |
| WO | 0175767 A1 | 10/2001 |
| WO | 2005018579 A2 | 3/2005 |
| WO | 2008038050 A2 | 4/2008 |
| WO | 2009040080 A1 | 4/2009 |
| WO | 2009042984 A1 | 4/2009 |

OTHER PUBLICATIONS

Alanvert, E. et al., "Highly stereoselective biocatalytic reduction of alpha-halo ketones," Tetrahedron: Symmetry vol. 20: 2462-2466 (2009).
Santaniello, E., et al., "Chiral Synthesis of a component of amanita muscaria, (−)4-hydroxypyrrolidin-2-one, and assessment of its absolute configuration," Journal Chemical Research, vol. 132:132-133 (1984).
Zhu, D. et al, "Green synthesis of important pharmaceutical building blocks: enzymatic access to enantiomerically pure α-chloroalcohols," Tetrahedron: Asymmetry 16:3275-3278 (2005).
Genbank No. YP_001165929 dated May 8, 2007.
Genbank No. AB{64403.1 dated Apr. 18, 2007.
Kambourakis, S., et al., "Ketoreductases in the synthesis of valuable chiral intermediates: application in the synthesis of α-hydroxy β-amino and β-hydroxy γ-amino acids," Tetrahedron, 60:663-339 (2004).

*Primary Examiner* — Delia Ramirez
(74) *Attorney, Agent, or Firm* — Codexis, Inc.

(57) ABSTRACT

The present disclosure relates to engineered ketoreductase polypeptides and uses thereof for the preparation of α-chloroalcohols from α-chloroketones. Also provided are polynucleotides encoding the engineered ketoreductase polypeptides and host cells capable of expressing the engineered ketoreductase polypeptides.

14 Claims, No Drawings

SEQUENCE LISTING

```
<160> NUMBER OF SEQ ID NOS: 80

<210> SEQ ID NO 1
<211> LENGTH: 792
<212> TYPE: DNA
<213> ORGANISM: Artificial Sequence
<220> FEATURE:
<223> OTHER INFORMATION: Codon optimized sequence of ketoreductase from
      Novosphingobium aromaticivorans

<400> SEQUENCE: 1
atgccgcttg aaatgacgat tgctctcaac aatgtggtcg ccgtcgtcac cggcgcggcg      60
ggaggcatcg gccgcgaact ggtcaaggcg atgaaggccg ccaacgccat cgtcatcgcc     120
accgacatgg cccccctcggc cgatgtcgaa ggcgcggacc attatctcca gcacgacgtg     180
acgagcgagg ccggctggaa ggccgtcgcg gcgctggccc aggaaaagta cgggcgcgtc     240
gatgcgctgg tgcacaacgc gggcatctcg atcgtcacga gttcgaaga cactccgctg     300 tccgatttcc accgcgtgaa cacggtcaac gtcgattcca tcatcatcgg tacgcaggtc     360
ctgctgccgc tgctcaagga aggcggcaag gcgcgcgcag gggcgcctc ggtggtcaac      420 ttctccagcg tcggggcct gcgcggcgcg gcgttcaatg cggcctattg caccagcaag     480
gcggcggtga agatgctctc gaagtgcctc ggcgcggaat tcgcggcgct cggctacaac     540
atccgcgtca actccgtgca tccggcggc atcgataccc cgatgctcgg ctcgatcatg     600
gacaagtacg tcgaactcgg cgctgccccc tcgcgcgagg tggcccaggc cgcgatggaa     660
```

```
atgcgccacc cgatcggtcg catgggtcgc cctgccgaaa tgggcggcgg cgtggtctat    720
ctctgctccg acgcagcaag cttcgtcacc tgcacggaat cgtgatgga cggcggcttc    780 agccaggtct ga                                                       792
```

<210> SEQ ID NO 2
<211> LENGTH: 263
<212> TYPE: PRT
<213> ORGANISM: Novosphingobium aromaticivorans

<400> SEQUENCE: 2

```
Met Pro Leu Glu Met Thr Ile Ala Leu Asn Asn Val Val Ala Val Val
1               5                   10                  15

Thr Gly Ala Ala Gly Gly Ile Gly Arg Glu Leu Val Lys Ala Met Lys
            20                  25                  30

Ala Ala Asn Ala Ile Val Ile Ala Thr Asp Met Ala Pro Ser Ala Asp
        35                  40                  45

Val Glu Gly Ala Asp His Tyr Leu Gln His Asp Val Thr Ser Glu Ala
    50                  55                  60

Gly Trp Lys Ala Val Ala Ala Leu Ala Gln Glu Lys Tyr Gly Arg Val
65                  70                  75                  80

Asp Ala Leu Val His Asn Ala Gly Ile Ser Ile Val Thr Lys Phe Glu
                85                  90                  95

Asp Thr Pro Leu Ser Asp Phe His Arg Val Asn Thr Val Asn Val Asp
            100                 105                 110

Ser Ile Ile Ile Gly Thr Gln Val Leu Leu Pro Leu Leu Lys Glu Gly
        115                 120                 125

Gly Lys Ala Arg Ala Gly Gly Ala Ser Val Val Asn Phe Ser Ser Val
    130                 135                 140

Gly Gly Leu Arg Gly Ala Ala Phe Asn Ala Ala Tyr Cys Thr Ser Lys
145                 150                 155                 160

Ala Ala Val Lys Met Leu Ser Lys Cys Leu Gly Ala Glu Phe Ala Ala
                165                 170                 175

Leu Gly Tyr Asn Ile Arg Val Asn Ser Val His Pro Gly Gly Ile Asp
            180                 185                 190

Thr Pro Met Leu Gly Ser Ile Met Asp Lys Tyr Val Glu Leu Gly Ala
        195                 200                 205

Ala Pro Ser Arg Glu Val Ala Gln Ala Ala Met Glu Met Arg His Pro
    210                 215                 220

Ile Gly Arg Met Gly Arg Pro Ala Glu Met Gly Gly Gly Val Val Tyr
225                 230                 235                 240

Leu Cys Ser Asp Ala Ala Ser Phe Val Thr Cys Thr Glu Phe Val Met
                245                 250                 255

Asp Gly Gly Phe Ser Gln Val
            260
```

<210> SEQ ID NO 3
<211> LENGTH: 792
<212> TYPE: DNA
<213> ORGANISM: Artificial Sequence
<220> FEATURE:
<223> OTHER INFORMATION: Variant of ketoreductase from Novosphingobium
       aromaticivorans

<400> SEQUENCE: 3

```
atgccgcttg aaatgacgat tgctctcaac aatgtggtcg ccgtcgtcac cggcgcggcg    60
```

```
ggaggcatcg gccgcgaact ggtcaaggcg atgaaggccg ccaacgccat cgtcatcgcc    120
accgacatgg cgccctcggc cgatgtcgaa ggcgcggacc attatctcca gcacgacgtg    180
acgagcgagg ccggctggaa ggcggtcgcg gcgctggccc aggaaaagta cgggcgcgtc    240
gatgcgctgg tgcacaacgc gggcatctcg atcgtcacga agttcgaaga cactccgctg    300
tccgatttcc accgcgtgaa cacggtcaac gtcgattcca tcatcatcgg tacgcaggtc    360
ctgctgccgc tgctcaagga aggcggcaag gcgcgcgcag ggggcgcctc ggtggtcaac    420
ttctccagcg tcgcgggtct cgcgggcgcg gcgttcaatg cggcctattg caccagcaag    480
gcggcggtga agatgctctc gaagtgcctc ggcgcggaat cgcggcgct cggctacaac     540 atccgcgtca actccgtgca tccgggcggc atcgataccc cgatgctcgg ctcgatcatg    600
gacaagtacg tcgaactcgg cgctgccccc tcgcgcgagg tggcccaggc cgcgatggaa    660
atgcgccacc cgatcggtcg catgggtcgc cctgccgaaa tgggcggcgg cgtggtctat    720
ctctgctccg acgcagcaag cttcgtcacc tgcacggaat cgtgatgga cggcggcttc     780 agccaggtct ga                                                        792
```

<210> SEQ ID NO 4
<211> LENGTH: 263
<212> TYPE: PRT
<213> ORGANISM: Artificial Sequence
<220> FEATURE:
<223> OTHER INFORMATION: Variant of ketoreductase from Novosphingobium aromaticivorans

<400> SEQUENCE: 4

```
Met Pro Leu Glu Met Thr Ile Ala Leu Asn Asn Val Val Ala Val Val
1               5                   10                  15

Thr Gly Ala Ala Gly Gly Ile Gly Arg Glu Leu Val Lys Ala Met Lys
            20                  25                  30

Ala Ala Asn Ala Ile Val Ile Ala Thr Asp Met Ala Pro Ser Ala Asp
        35                  40                  45

Val Glu Gly Ala Asp His Tyr Leu Gln His Asp Val Thr Ser Glu Ala
    50                  55                  60

Gly Trp Lys Ala Val Ala Ala Leu Ala Gln Glu Lys Tyr Gly Arg Val
65                  70                  75                  80

Asp Ala Leu Val His Asn Ala Gly Ile Ser Ile Val Thr Lys Phe Glu
                85                  90                  95

Asp Thr Pro Leu Ser Asp Phe His Arg Val Asn Thr Val Asn Val Asp
            100                 105                 110

Ser Ile Ile Ile Gly Thr Gln Val Leu Leu Pro Leu Leu Lys Glu Gly
        115                 120                 125

Gly Lys Ala Arg Ala Gly Gly Ala Ser Val Val Asn Phe Ser Ser Val
    130                 135                 140

Ala Gly Leu Arg Gly Ala Ala Phe Asn Ala Ala Tyr Cys Thr Ser Lys
145                 150                 155                 160

Ala Ala Val Lys Met Leu Ser Lys Cys Leu Gly Ala Glu Phe Ala Ala
                165                 170                 175

Leu Gly Tyr Asn Ile Arg Val Asn Ser Val His Pro Gly Gly Ile Asp
            180                 185                 190

Thr Pro Met Leu Gly Ser Ile Met Asp Lys Tyr Val Glu Leu Gly Ala
        195                 200                 205

Ala Pro Ser Arg Glu Val Ala Gln Ala Ala Met Glu Met Arg His Pro
    210                 215                 220
```

Ile Gly Arg Met Gly Arg Pro Ala Glu Met Gly Gly Val Val Tyr
225                 230                 235                 240

Leu Cys Ser Asp Ala Ala Ser Phe Val Thr Cys Thr Glu Phe Val Met
            245                 250                 255

Asp Gly Gly Phe Ser Gln Val
        260

<210> SEQ ID NO 5
<211> LENGTH: 792
<212> TYPE: DNA
<213> ORGANISM: Artificial Sequence
<220> FEATURE:
<223> OTHER INFORMATION: Variant of ketoreductase from Novosphingobium
      aromaticivorans

<400> SEQUENCE: 5
atgccgcttg aaatgacgat tgctctcaac aatgtggtcg ccgtcgtcac cggcgcggcg    60
ggaggcatcg gccgcgaact ggtcaaggcg atgaaggccg ccaacgccat cgtcatcgcc   120
accgacatgg cgccctcggc cgatgtcgaa ggcgcggacc attatctcca gcacgacgtg   180
acgagcgagg ccggctggaa ggcggtcgcg gcactggccc aggaaaagta cgggcgcgtc   240
gatgcgctgg tgcacaacgc gggcatctcg atcgtcacga gttcgaaga cactccgctg   300 tccgatttcc accgcgtgaa cacggtcaac gtcgattcca tcatcatcgg tacgcaggtc   360
ctgctgccgc tgctcaagga aggcggcaag gcgcgcgcag ggggcgcctc ggtggtcaac   420
ttctccagcg tcgcgggtct gcgcggcgcg gcgttcaatg cggcctattg caccagcaag   480
gcggcggtga agatgctctc gaagtgcctc ggcgcggaat cgcggcgct cggctacaac   540 atccgcgtca actccgtgca tccgggcggc atcgataccc cgatgctcgg ctcgctgatg   600
gacaagtacg tcgaactcgg cgctgccccc tcgcgcgagg tggcccaggc cgcgatggaa   660
atgcgccacc cgatcggtcg catgggtcgc cctgccgaaa tgggcggcgg cgtggtctat   720
ctctgctccg acgcagcaag cttcgtcacc tgcacggaat cgtgatgga cggcggcttc   780 agccaggtct ga                                                       792

<210> SEQ ID NO 6
<211> LENGTH: 263
<212> TYPE: PRT
<213> ORGANISM: Artificial Sequence
<220> FEATURE:
<223> OTHER INFORMATION: Variant of ketoreductase from Novosphingobium
      aromaticivorans

<400> SEQUENCE: 6

Met Pro Leu Glu Met Thr Ile Ala Leu Asn Asn Val Val Ala Val Val
1               5                   10                  15

Thr Gly Ala Ala Gly Gly Ile Gly Arg Glu Leu Val Lys Ala Met Lys
            20                  25                  30

Ala Ala Asn Ala Ile Val Ile Ala Thr Asp Met Ala Pro Ser Ala Asp
        35                  40                  45

Val Glu Gly Ala Asp His Tyr Leu Gln His Asp Val Thr Ser Glu Ala
    50                  55                  60

Gly Trp Lys Ala Val Ala Ala Leu Ala Gln Glu Lys Tyr Gly Arg Val
65                  70                  75                  80

Asp Ala Leu Val His Asn Ala Gly Ile Ser Ile Val Thr Lys Phe Glu
                85                  90                  95

Asp Thr Pro Leu Ser Asp Phe His Arg Val Asn Thr Val Asn Val Asp
            100                 105                 110

```
Ser Ile Ile Ile Gly Thr Gln Val Leu Leu Pro Leu Leu Lys Glu Gly
        115                 120                 125

Gly Lys Ala Arg Ala Gly Gly Ala Ser Val Val Asn Phe Ser Ser Val
        130                 135                 140

Ala Gly Leu Arg Gly Ala Ala Phe Asn Ala Ala Tyr Cys Thr Ser Lys
145                 150                 155                 160

Ala Ala Val Lys Met Leu Ser Lys Cys Leu Gly Ala Glu Phe Ala Ala
                165                 170                 175

Leu Gly Tyr Asn Ile Arg Val Asn Ser Val His Pro Gly Gly Ile Asp
            180                 185                 190

Thr Pro Met Leu Gly Ser Leu Met Asp Lys Tyr Val Glu Leu Gly Ala
        195                 200                 205

Ala Pro Ser Arg Glu Val Ala Gln Ala Ala Met Glu Met Arg His Pro
    210                 215                 220

Ile Gly Arg Met Gly Arg Pro Ala Glu Met Gly Gly Val Val Tyr
225                 230                 235                 240

Leu Cys Ser Asp Ala Ala Ser Phe Val Thr Cys Thr Glu Phe Val Met
                245                 250                 255

Asp Gly Gly Phe Ser Gln Val
            260
```

```
<210> SEQ ID NO 7
<211> LENGTH: 792
<212> TYPE: DNA
<213> ORGANISM: Artificial Sequence
<220> FEATURE:
<223> OTHER INFORMATION: Variant of ketoreductase from Novosphingobium
      aromaticivorans

<400> SEQUENCE: 7
atgccgcttg aaatgacgat tgctctcaac aatgtggtcg ccgtcgtcac cggcgcggcg    60
ggaggcatcg ccgcgaact ggtcaaggcg atgaaggccg ccaacgccat cgtcatcgcc    120
accgacatgg cgccctcggc cgatgtcgaa ggcgcggacc attatctcca gcacgacgtg    180
acgagcgagg ccggctggaa ggcggtcgcg gcgctggccc aggaaaagta cgggcgcgtc    240
gatgcgctgg tgcacaacgc gggcatcgtg atcgtcacga agttcgaaga cactccgctg    300
tccgatttcc accgcgtgaa cacggtcaac gtcgattcca tcatcatcgg tacgcaggtc    360
ctgctgccgc tgctcaagga aggcggcaag gcgcgcgcag ggggcgcctc ggtggtcaac    420
ttctccagcg tcgggggtct gcgcggcgcg gcgttcaatg cggcctattg caccagcaag    480
gcggcggtga agatgctctc gaagtgcctc ggcgcggaat tcgcggcgct cggctacaac    540
atccgcgtca actccgtgca tccggggcggc atcgatacccc gatgctcgg ctcgatcatg    600 gacaagtacg tcgaactcgg cgctgccccc tcgcgcgagg tggcccaggc cgcgatggaa    660
atgcgccacc cgatcggtcg catgggtcgc cctgccgaaa tgggcggcgg cgtggtctat    720
ctctgctccg acgcagcaag cttcgtcacc tgcacggaat tcgtgatgga cggcggcttc    780
agccaggtct ga                                                       792

<210> SEQ ID NO 8
<211> LENGTH: 263
<212> TYPE: PRT
<213> ORGANISM: Artificial Sequence
<220> FEATURE:
<223> OTHER INFORMATION: Variant of ketoreductase from Novosphingobium
      aromaticivorans
```

<400> SEQUENCE: 8

Met Pro Leu Glu Met Thr Ile Ala Leu Asn Asn Val Val Ala Val Val
1               5                   10                  15

Thr Gly Ala Ala Gly Gly Ile Gly Arg Glu Leu Val Lys Ala Met Lys
            20                  25                  30

Ala Ala Asn Ala Ile Val Ile Ala Thr Asp Met Ala Pro Ser Ala Asp
        35                  40                  45

Val Glu Gly Ala Asp His Tyr Leu Gln His Asp Val Thr Ser Glu Ala
    50                  55                  60

Gly Trp Lys Ala Val Ala Leu Ala Gln Glu Lys Tyr Gly Arg Val
65              70                  75                  80

Asp Ala Leu Val His Asn Ala Gly Ile Val Ile Val Thr Lys Phe Glu
                85                  90                  95

Asp Thr Pro Leu Ser Asp Phe His Arg Val Asn Thr Val Asn Val Asp
            100                 105                 110

Ser Ile Ile Ile Gly Thr Gln Val Leu Leu Pro Leu Leu Lys Glu Gly
        115                 120                 125

Gly Lys Ala Arg Ala Gly Gly Ala Ser Val Val Asn Phe Ser Ser Val
130                 135                 140

Gly Gly Leu Arg Gly Ala Ala Phe Asn Ala Ala Tyr Cys Thr Ser Lys
145                 150                 155                 160

Ala Ala Val Lys Met Leu Ser Lys Cys Leu Gly Ala Glu Phe Ala Ala
                165                 170                 175

Leu Gly Tyr Asn Ile Arg Val Asn Ser Val His Pro Gly Gly Ile Asp
            180                 185                 190

Thr Pro Met Leu Gly Ser Ile Met Asp Lys Tyr Val Glu Leu Gly Ala
        195                 200                 205

Ala Pro Ser Arg Glu Val Ala Gln Ala Ala Met Glu Met Arg His Pro
    210                 215                 220

Ile Gly Arg Met Gly Arg Pro Ala Glu Met Gly Gly Val Val Tyr
225                 230                 235                 240

Leu Cys Ser Asp Ala Ala Ser Phe Val Thr Cys Thr Glu Phe Val Met
                245                 250                 255

Asp Gly Gly Phe Ser Gln Val
            260

<210> SEQ ID NO 9
<211> LENGTH: 792
<212> TYPE: DNA
<213> ORGANISM: Artificial Sequence
<220> FEATURE:
<223> OTHER INFORMATION: Variant of ketoreductase from Novosphingobium
      aromaticivorans

<400> SEQUENCE: 9
atgccgcttg aaatgacgat tgctctcaac aatgtggtcg ccgtcgtcac cggcgcggcg     60
ggaggcatcg gccgcgaact ggtcaaggcg atgaaggccg ccaacgccat cgtcatcgcc    120
accgacatgg cgccctcggc cgatgtcgaa ggcgcggacc attatctcca gcacgacgtg    180
acgagcgagg ccggctggaa ggcggtcgcg gcgctggccc aggaaaagta cgggcgcgtc    240
gatgcgctgg tgcacaacgc gggcatctcg atcgtcacga agttcgaaga cactccgctg    300
tccgatttcc accgcgtgaa cacggtcaac gtcgattcca tcatcatcgg tacgcaggtc    360
ctgctgccgc tgctcaagga aggcggcaag gcgcgcgcag ggggcgcctc ggtggtcaac    420
ttctccagcg tcggggtctc gcgcggcgcg gcgttgaatg cggcctattg caccagcaag    480

```
gcggcggtga agatgctctc gaagtgcctc ggcgcggaat tcgcggcgct cggctacaac      540
atccgcgtca actccgtgca tccgggcggc atcgataccc cgatgctcgg ctcgatcatg      600
gacaagtacg tcgaactcgg cgctgccccc tcgcgcgagg tggcccaggc cgcgatggaa      660
atgcgccacc cgatcggtcg catgggtcgc cctgccgaaa tgggcggcgg cgtggtctat      720
ctctgctccg acgcagcaag cttcgtcacc tgcacggaat tcgtgatgga cggcggcttc      780
agccaggtct ga                                                         792
```

<210> SEQ ID NO 10
<211> LENGTH: 263
<212> TYPE: PRT
<213> ORGANISM: Artificial Sequence
<220> FEATURE:
<223> OTHER INFORMATION: Variant of ketoreductase from Novosphingobium aromaticivorans

<400> SEQUENCE: 10

```
Met Pro Leu Glu Met Thr Ile Ala Leu Asn Asn Val Val Ala Val Val
1               5                   10                  15

Thr Gly Ala Ala Gly Gly Ile Gly Arg Glu Leu Val Lys Ala Met Lys
            20                  25                  30

Ala Ala Asn Ala Ile Val Ile Ala Thr Asp Met Ala Pro Ser Ala Asp
        35                  40                  45

Val Glu Gly Ala Asp His Tyr Leu Gln His Asp Val Thr Ser Glu Ala
    50                  55                  60

Gly Trp Lys Ala Val Ala Ala Leu Ala Gln Glu Lys Tyr Gly Arg Val
65                  70                  75                  80

Asp Ala Leu Val His Asn Ala Gly Ile Ser Ile Val Thr Lys Phe Glu
                85                  90                  95

Asp Thr Pro Leu Ser Asp Phe His Arg Val Asn Thr Val Asn Val Asp
            100                 105                 110

Ser Ile Ile Ile Gly Thr Gln Val Leu Leu Pro Leu Leu Lys Glu Gly
        115                 120                 125

Gly Lys Ala Arg Ala Gly Gly Ala Ser Val Val Asn Phe Ser Ser Val
    130                 135                 140

Gly Gly Leu Arg Gly Ala Ala Leu Asn Ala Ala Tyr Cys Thr Ser Lys
145                 150                 155                 160

Ala Ala Val Lys Met Leu Ser Lys Cys Leu Gly Ala Glu Phe Ala Ala
                165                 170                 175

Leu Gly Tyr Asn Ile Arg Val Asn Ser Val His Pro Gly Gly Ile Asp
            180                 185                 190

Thr Pro Met Leu Gly Ser Ile Met Asp Lys Tyr Val Glu Leu Gly Ala
        195                 200                 205

Ala Pro Ser Arg Glu Val Ala Gln Ala Ala Met Glu Met Arg His Pro
    210                 215                 220

Ile Gly Arg Met Gly Arg Pro Ala Glu Met Gly Gly Gly Val Val Tyr
225                 230                 235                 240

Leu Cys Ser Asp Ala Ala Ser Phe Val Thr Cys Thr Glu Phe Val Met
                245                 250                 255

Asp Gly Gly Phe Ser Gln Val
            260
```

<210> SEQ ID NO 11
<211> LENGTH: 792
<212> TYPE: DNA

<213> ORGANISM: Artificial Sequence
<220> FEATURE:
<223> OTHER INFORMATION: Variant of ketoreductase from Novosphingobium aromaticivorans

<400> SEQUENCE: 11

```
atgccgcttg aaatgacgat tgctctcaac aatgtggtcg ccgtcgtcac cggcgcggcg    60
ggaggcatcg gccgcgaact ggtcaaggcg atgaaggccg ccaacgccat cgtcatcgcc   120
accgacatgg cgccctcggc cgatgtcgaa ggcgcggacc attatctcca gcacgacgtg   180
acgagcgagg ccggctggaa ggcggtcgcg gcgctggccc aggaaaagta cgggcgcgtc   240
gatgcgctgt tgcacaacgc gggcatctcg atcgtcacga agttcgaaga cactccgctg   300
tccgatttcc accgcgtgaa cacggtcaac gtcgattcca tcatcatcgg tacgcaggtc   360
ctgctgccgc tgctcaagga aggcggcaag gcgcgcgcag ggggcgcctc ggtggtcaac   420
ttctccagcg tcgggggtct cgcgggcgcg gcgttcaatg cggcctattg caccagcaag   480
gcggcggtga agatgctctc gaagtgcctc ggcgcggaat cgcggcgct cggctacaac   540
atccgcgtca actccgtgca tccgggcggc atcgataccc cgatgctggg ctcgatcatg   600
gacaagtacg tcgaactcgg cgctgccccc tcgcgcgagg tggcccaggc cgcgatggaa   660
atgcgccacc cgatcggtcg catgggtcgc cctgccgaaa tgggcggcgg cgtggtctat   720
ctctgctccg acgcagcaag cttcgtcacc tgcacggaat cgtgatgga cggcggcttc   780
agccaggtct ga                                                       792
```

<210> SEQ ID NO 12
<211> LENGTH: 263
<212> TYPE: PRT
<213> ORGANISM: Artificial Sequence
<220> FEATURE:
<223> OTHER INFORMATION: Variant of ketoreductase from Novosphingobium aromaticivorans

<400> SEQUENCE: 12

```
Met Pro Leu Glu Met Thr Ile Ala Leu Asn Asn Val Val Ala Val Val
1               5                   10                  15

Thr Gly Ala Ala Gly Gly Ile Gly Arg Glu Leu Val Lys Ala Met Lys
            20                  25                  30

Ala Ala Asn Ala Ile Val Ile Ala Thr Asp Met Ala Pro Ser Ala Asp
        35                  40                  45

Val Glu Gly Ala Asp His Tyr Leu Gln His Asp Val Thr Ser Glu Ala
    50                  55                  60

Gly Trp Lys Ala Val Ala Ala Leu Ala Gln Glu Lys Tyr Gly Arg Val
65                  70                  75                  80

Asp Ala Leu Val His Asn Ala Gly Ile Ser Ile Val Thr Lys Phe Glu
                85                  90                  95

Asp Thr Pro Leu Ser Asp Phe His Arg Val Asn Thr Val Asn Val Asp
            100                 105                 110

Ser Ile Ile Ile Gly Thr Gln Val Leu Leu Pro Leu Leu Lys Glu Gly
        115                 120                 125

Gly Lys Ala Arg Ala Gly Gly Ala Ser Val Val Asn Phe Ser Ser Val
    130                 135                 140

Gly Gly Leu Arg Gly Ala Ala Phe Asn Ala Ala Tyr Cys Thr Ser Lys
145                 150                 155                 160

Ala Ala Val Lys Met Leu Ser Lys Cys Leu Gly Ala Glu Phe Ala Ala
                165                 170                 175
```

```
Leu Gly Tyr Asn Ile Arg Val Asn Ser Val His Pro Gly Gly Ile Asp
            180                 185                 190

Thr Pro Met Leu Gly Ser Ile Met Asp Lys Tyr Val Glu Leu Gly Ala
            195                 200                 205

Ala Pro Ser Arg Glu Val Ala Gln Ala Ala Met Glu Met Arg His Pro
        210                 215                 220

Ile Gly Arg Met Gly Arg Pro Ala Glu Met Gly Gly Val Val Tyr
225                 230                 235                 240

Leu Cys Ser Asp Ala Ala Ser Phe Val Thr Cys Thr Glu Phe Val Met
                245                 250                 255

Asp Gly Gly Phe Ser Gln Val
            260

<210> SEQ ID NO 13
<211> LENGTH: 792
<212> TYPE: DNA
<213> ORGANISM: Artificial Sequence
<220> FEATURE:
<223> OTHER INFORMATION: Variant of ketoreductase from Novosphingobium
      aromaticivorans

<400> SEQUENCE: 13
atgccgcttg aaatgacgat tgctctcaac aatgtggtcg ccgtcgtcac cggcgcggcg      60
ggaggcatcg gccgcgaact ggtcaaggcg atgaaggccg ccaacgccat cgtcatcgcc     120
accgacatgg cgccctcggc cgatgtcgaa ggcgcggacc attatctcca gcacgacgtg     180
acgagcgagg ccggctggaa ggcggtcgcg gcgctggccc aggaaaagta cgggcgcgtc     240
gatgcgctgg tgcacaacgc gggcatctcg atcgtcacga agttcgaaga cactccgctg     300
tccgatttcc accgcgtgaa cacggtcaac gtcgattcca tcatcatcgg tacgcaggtc     360
ctgctgccgc tgctcaagga aggcggcaag gcgcgcgcag ggggcgcctc ggtggtcaac     420
ttctccagcg tcgggggtct gcgcggcgcg gcgttcaatg cggcctattg caccagcaag     480
gcggcggtga agatgctctc gaagtgcctc ggcgcgaat tcgcggcgct cggctacaac     540
atccgcgtca actccgtgca tccggggcgg atcgataccc cgatgctcgg ctcgatcatg     600
gacaagtacg tcgaactcgg cgctgccccc tcgcgcgagg tggcccaggc cgcgatggaa     660
atgcgccacc cgatcggtcg catgggtcgc cctgccgaaa tgggcggcgg cgtggtctat     720
ctctgctccg acgcagcaag cttcgtcacc tgcacggaat tcgtgatgga cggcggcttc     780
agccaggtct ga                                                         792

<210> SEQ ID NO 14
<211> LENGTH: 263
<212> TYPE: PRT
<213> ORGANISM: Artificial Sequence
<220> FEATURE:
<223> OTHER INFORMATION: Variant of ketoreductase from Novosphingobium
      aromaticivorans

<400> SEQUENCE: 14

Met Pro Leu Glu Met Thr Ile Ala Leu Asn Asn Val Val Ala Val Val
1               5                   10                  15

Thr Gly Ala Ala Gly Gly Ile Gly Arg Glu Leu Val Lys Ala Met Lys
            20                  25                  30

Ala Ala Asn Ala Ile Val Ile Ala Thr Asp Met Ala Pro Ser Ala Asp
        35                  40                  45

Val Glu Gly Ala Asp His Tyr Leu Gln His Asp Val Thr Ser Glu Ala
    50                  55                  60
```

```
Gly Trp Lys Ala Val Ala Ala Leu Ala Gln Glu Lys Tyr Gly Arg Val
 65                  70                  75                  80

Asp Ala Leu Val His Asn Ala Gly Ile Ser Ile Val Thr Lys Phe Glu
                 85                  90                  95

Asp Thr Pro Leu Ser Asp Phe His Arg Val Asn Thr Val Asn Val Asp
            100                 105                 110

Ser Ile Ile Ile Gly Thr Gln Val Leu Leu Pro Leu Leu Lys Glu Gly
        115                 120                 125

Gly Lys Ala Arg Ala Gly Gly Ala Ser Val Val Asn Phe Ser Ser Val
130                 135                 140

Gly Gly Leu Arg Gly Ala Ala Phe Asn Ala Ala Tyr Cys Thr Ser Lys
145                 150                 155                 160

Ala Ala Val Lys Met Leu Ser Lys Cys Leu Gly Ala Glu Phe Ala Ala
                165                 170                 175

Leu Gly Tyr Asn Ile Arg Val Asn Ser Val His Pro Gly Gly Ile Asp
            180                 185                 190

Thr Pro Met Leu Gly Ser Ile Met Asp Lys Tyr Val Glu Leu Gly Ala
        195                 200                 205

Ala Pro Ser Arg Glu Val Ala Gln Ala Ala Met Glu Met Arg His Pro
210                 215                 220

Ile Gly Arg Met Gly Arg Pro Ala Glu Met Gly Gly Val Val Tyr
225                 230                 235                 240

Leu Cys Ser Asp Ala Ala Ser Phe Val Thr Cys Thr Glu Phe Val Met
                245                 250                 255

Asp Gly Gly Phe Ser Gln Val
            260
```

<210> SEQ ID NO 15
<211> LENGTH: 792
<212> TYPE: DNA
<213> ORGANISM: Artificial Sequence
<220> FEATURE:
<223> OTHER INFORMATION: Variant of ketoreductase from Novosphingobium
      aromaticivorans

<400> SEQUENCE: 15

```
atgccgcttg aaatgacgat tgctctcaac aatgtggtcg ccgtcgtcac cggcgcggcg    60
ggaggcatcg ccgcgaact ggtcaaggcg atgaaggccg ccaacgccat cgtcatcgcc   120
accgacatgg cgccctcggc cgatgtcgaa ggcgcggacc attatctcca gcacgacgtg   180
acgagcgagg ccggctggaa ggcggtcgcg gcgctggccc aggaaaagta cgggcgcgtc   240
gatgcgctgg tgcacaacgc gggcatctcg atcgtcacga gttcgaagaa cactccgctg   300
tccgatttcc accgcgtgaa cacggtcaac gtcgattcca tcatcatcgg tacgcaggtc   360
ctgctgccgc tgctcaagga aggcggcaag gcgcgcgcag ggggcgcctc ggtggtcaac   420
ttctccagcg tcgggggtct cgcggcgcg cgttcaatg cggcctattg caccagcaag   480
gcggcggtga agatgctctc gaagtgcctc ggcgcggaat cgcggcgct cggctacaac   540
atccgcgtca actccgtgca tccgggcggc atcgataccc cgatgctcgg ctcgctgatg   600
gacaagtacg tcgaactcgg cgctgccccc tcgcgcgagg tggcccaggc cgcgatggaa   660
atgcgccacc cgatcggtcg catgggtcgc cctgccgaaa tgggcggcgg cgtggtctat   720
ctctgctccg acgcagcaag cttcgtcacc tgcacggaat tcgtgatgga cggcggcttc   780
agccaggtct ga                                                      792
```

<210> SEQ ID NO 16
<211> LENGTH: 263
<212> TYPE: PRT
<213> ORGANISM: Artificial Sequence
<220> FEATURE:
<223> OTHER INFORMATION: Variant of ketoreductase from Novosphingobium aromaticivorans

<400> SEQUENCE: 16

```
Met Pro Leu Glu Met Thr Ile Ala Leu Asn Asn Val Val Ala Val Val
1               5                   10                  15

Thr Gly Ala Ala Gly Gly Ile Gly Arg Glu Leu Val Lys Ala Met Lys
            20                  25                  30

Ala Ala Asn Ala Ile Val Ile Ala Thr Asp Met Ala Pro Ser Ala Asp
        35                  40                  45

Val Glu Gly Ala Asp His Tyr Leu Gln His Asp Val Thr Ser Glu Ala
    50                  55                  60

Gly Trp Lys Ala Val Ala Leu Ala Gln Glu Lys Tyr Gly Arg Val
65                  70                  75                  80

Asp Ala Leu Val His Asn Ala Gly Ile Ser Ile Val Thr Lys Phe Glu
                85                  90                  95

Asp Thr Pro Leu Ser Asp Phe His Arg Val Asn Thr Val Asn Val Asp
            100                 105                 110

Ser Ile Ile Ile Gly Thr Gln Val Leu Leu Pro Leu Leu Lys Glu Gly
        115                 120                 125

Gly Lys Ala Arg Ala Gly Gly Ala Ser Val Val Asn Phe Ser Ser Val
    130                 135                 140

Gly Gly Leu Arg Gly Ala Ala Phe Asn Ala Ala Tyr Cys Thr Ser Lys
145                 150                 155                 160

Ala Ala Val Lys Met Leu Ser Lys Cys Leu Gly Ala Glu Phe Ala Ala
                165                 170                 175

Leu Gly Tyr Asn Ile Arg Val Asn Ser Val His Pro Gly Gly Ile Asp
            180                 185                 190

Thr Pro Met Leu Gly Ser Leu Met Asp Lys Tyr Val Glu Leu Gly Ala
        195                 200                 205

Ala Pro Ser Arg Glu Val Ala Gln Ala Ala Met Glu Met Arg His Pro
    210                 215                 220

Ile Gly Arg Met Gly Arg Pro Ala Glu Met Gly Gly Val Val Tyr
225                 230                 235                 240

Leu Cys Ser Asp Ala Ala Ser Phe Val Thr Cys Thr Glu Phe Val Met
                245                 250                 255

Asp Gly Gly Phe Ser Gln Val
            260
```

<210> SEQ ID NO 17
<211> LENGTH: 792
<212> TYPE: DNA
<213> ORGANISM: Artificial Sequence
<220> FEATURE:
<223> OTHER INFORMATION: Variant of ketoreductase from Novosphingobium aromaticivorans

<400> SEQUENCE: 17

```
atgccgcttg aaatgacgat tgctctcaac aatgtggtcg ccgtcgtcac cggcgcggcg      60
ggaggcatcg gccgcgaact ggtcaaggcg atgaaggccg ccaacgccat cgtcatcgcc     120
accgacatgg cgccctcggc cgatgtcgaa ggcgcggacc attatctcca gcacgacgtg     180
```

```
acgagcgagg ccggctggaa ggcggtcgcg gcgctggccc aggaaaagta cgggcgcgtc    240
gatgcgctgg tgcacaacgc gggcatctcg atcgtcacga agttcgaaga cactccgctg    300
tccgatttcc accgcgtgaa cacggtcaac gtcgattcca tcatcatcgg tacgcaggtc    360
ctgctgccgc tgctcaagga aggcggcaag gcgcgcgcag ggggcgcctc ggtggtcaac    420
ttctccagcg tcggggtct gcgcggcgcg gcgttcggtg cggcctattg caccagcaag    480
gcggcggtga agatgctctc gaagtgcctc ggcgcggaat cgcggcgct cggctacaac    540
atccgcgtca actccgtgca tccgggcggc atcgataccc cgatgctcgg ctcgatcatg    600
gacaagtacg tcgaactcgg cgctgccccc tcgcgcgagg tggcccaggc cgcgatggaa    660
atgcgccacc cgatcggtcg catgggtcgc cctgccgaaa tgggcggcgg cgtggtctat    720
ctctgctccg acgcagcaag cttcgtcacc tgcacggaat tcgtgatgga cggcggcttc    780
agccaggtct ga                                                        792
```

<210> SEQ ID NO 18
<211> LENGTH: 263
<212> TYPE: PRT
<213> ORGANISM: Artificial Sequence
<220> FEATURE:
<223> OTHER INFORMATION: Variant of ketoreductase from Novosphingobium
      aromaticivorans

<400> SEQUENCE: 18

```
Met Pro Leu Glu Met Thr Ile Ala Leu Asn Asn Val Val Ala Val Val
1               5                   10                  15

Thr Gly Ala Ala Gly Gly Ile Gly Arg Glu Leu Val Lys Ala Met Lys
            20                  25                  30

Ala Ala Asn Ala Ile Val Ile Ala Thr Asp Met Ala Pro Ser Ala Asp
        35                  40                  45

Val Glu Gly Ala Asp His Tyr Leu Gln His Asp Val Thr Ser Glu Ala
    50                  55                  60

Gly Trp Lys Ala Val Ala Ala Leu Ala Gln Glu Lys Tyr Gly Arg Val
65                  70                  75                  80

Asp Ala Leu Val His Asn Ala Gly Ile Ser Ile Val Thr Lys Phe Glu
                85                  90                  95

Asp Thr Pro Leu Ser Asp Phe His Arg Val Asn Thr Val Asn Val Asp
            100                 105                 110

Ser Ile Ile Ile Gly Thr Gln Val Leu Leu Pro Leu Leu Lys Glu Gly
        115                 120                 125

Gly Lys Ala Arg Ala Gly Gly Ala Ser Val Val Asn Phe Ser Ser Val
    130                 135                 140

Gly Gly Leu Arg Gly Ala Ala Phe Gly Ala Ala Tyr Cys Thr Ser Lys
145                 150                 155                 160

Ala Ala Val Lys Met Leu Ser Lys Cys Leu Gly Ala Glu Phe Ala Ala
                165                 170                 175

Leu Gly Tyr Asn Ile Arg Val Asn Ser Val His Pro Gly Gly Ile Asp
            180                 185                 190

Thr Pro Met Leu Gly Ser Ile Met Asp Lys Tyr Val Glu Leu Gly Ala
        195                 200                 205

Ala Pro Ser Arg Glu Val Ala Gln Ala Ala Met Glu Met Arg His Pro
    210                 215                 220

Ile Gly Arg Met Gly Arg Pro Ala Glu Met Gly Gly Gly Val Val Tyr
225                 230                 235                 240

Leu Cys Ser Asp Ala Ala Ser Phe Val Thr Cys Thr Glu Phe Val Met
```

```
                    245                 250                 255

Asp Gly Gly Phe Ser Gln Val
            260

<210> SEQ ID NO 19
<211> LENGTH: 792
<212> TYPE: DNA
<213> ORGANISM: Artificial Sequence
<220> FEATURE:
<223> OTHER INFORMATION: Variant of ketoreductase from Novosphingobium
      aromaticivorans

<400> SEQUENCE: 19
atgccgcttg aaatgacgat tgctctcaac aatgtggtcg ccgtcgtcac cggcgcggcg      60
ggaggcatcg gccgcgaact ggtcaaggcg atgaaggccg ccaacgccat cgtcatcgcc     120
accgacatgg cgccctcggc cgatgtcgaa ggcgcggacc attatctcca gcacgacgtg     180
acgagcgagg ccggctggaa ggcggtcgcg gcgctggccc aggaaaagta cgggcgcgtc     240
gatgcgctgg tgcacaacgc gggcatctcg atcgtcacga gttcgaaga cactccgctg      300 tccgatttcc accgcgtgaa cacggtcaac gtcgattcca tcatcatcgg tacgcaggtc     360
ctgctgccgc tgctcaagga aggcggcaag gcgcgcgcag ggggcgcctc ggtggtcaac     420
ttctccagcg tcgggggtct gcgcggcgcg gcgttcgttg cggcctattg caccagcaag     480
gcggcggtga agatgctctc gaagtgcctc ggcgcggaat cgcggcgct cggctacaac      540 atccgcgtca actccgtgca tccgggcggc atcgataccc cgatgctcgg ctcgatcatg     600
gacaagtacg tcgaactcgg cgctgccccc tcgcgcgagg tggcccaggc cgcgatggaa     660
atgcgccacc cgatcggtcg catgggtcgc cctgccgaaa tgggcggcgg cgtggtctat     720
ctctgctccg acgcagcaag cttcgtcacc tgcacggaat cgtgatgga cggcggcttc      780 agccaggtct ga                                                         792

<210> SEQ ID NO 20
<211> LENGTH: 263
<212> TYPE: PRT
<213> ORGANISM: Artificial Sequence
<220> FEATURE:
<223> OTHER INFORMATION: Variant of ketoreductase from Novosphingobium
      aromaticivorans

<400> SEQUENCE: 20

Met Pro Leu Glu Met Thr Ile Ala Leu Asn Asn Val Val Ala Val Val
1               5                   10                  15

Thr Gly Ala Ala Gly Gly Ile Gly Arg Glu Leu Val Lys Ala Met Lys
            20                  25                  30

Ala Ala Asn Ala Ile Val Ile Ala Thr Asp Met Ala Pro Ser Ala Asp
        35                  40                  45

Val Glu Gly Ala Asp His Tyr Leu Gln His Asp Val Thr Ser Glu Ala
    50                  55                  60

Gly Trp Lys Ala Val Ala Ala Leu Ala Gln Glu Lys Tyr Gly Arg Val
65                  70                  75                  80

Asp Ala Leu Val His Asn Ala Gly Ile Ser Ile Val Thr Lys Phe Glu
                85                  90                  95

Asp Thr Pro Leu Ser Asp Phe His Arg Val Asn Thr Val Asn Val Asp
            100                 105                 110

Ser Ile Ile Ile Gly Thr Gln Val Leu Leu Pro Leu Leu Lys Glu Gly
        115                 120                 125
```

```
Gly Lys Ala Arg Ala Gly Gly Ala Ser Val Val Asn Phe Ser Ser Val
    130                 135                 140

Gly Gly Leu Arg Gly Ala Ala Phe Val Ala Ala Tyr Cys Thr Ser Lys
145                 150                 155                 160

Ala Ala Val Lys Met Leu Ser Lys Cys Leu Gly Ala Glu Phe Ala Ala
                165                 170                 175

Leu Gly Tyr Asn Ile Arg Val Asn Ser Val His Pro Gly Gly Ile Asp
            180                 185                 190

Thr Pro Met Leu Gly Ser Ile Met Asp Lys Tyr Val Glu Leu Gly Ala
        195                 200                 205

Ala Pro Ser Arg Glu Val Ala Gln Ala Ala Met Glu Met Arg His Pro
210                 215                 220

Ile Gly Arg Met Gly Arg Pro Ala Glu Met Gly Gly Val Val Tyr
225                 230                 235                 240

Leu Cys Ser Asp Ala Ala Ser Phe Val Thr Cys Thr Glu Phe Val Met
                245                 250                 255

Asp Gly Gly Phe Ser Gln Val
            260
```

```
<210> SEQ ID NO 21
<211> LENGTH: 792
<212> TYPE: DNA
<213> ORGANISM: Artificial Sequence
<220> FEATURE:
<223> OTHER INFORMATION: Variant of ketoreductase from Novosphingobium
      aromaticivorans

<400> SEQUENCE: 21
atgccgcttg aaatgacgat tgctctcaac aatgtggtcg ccgtcgtcac cggcgcggcg      60
ggaggcatcg ccgcgaact  ggtcaaggcg atgaaggccg ccaacgccat cgtcatcgcc     120
accgacatgg cgccctcggc cgatgtcgaa ggcgcggacc attatctcca gcacgacgtg     180
acgagcgagg ccggctggaa ggcggtcgcg gcgctggccc aggaaaagta cgggcgcgtc     240
gatgcgctgg tgcacaacgc gggcatctcg atcgtcacga gttcgaaga  cactccgctg     300 tccgatttcc accgcgtgaa cacggtcaac gtcgattcca tcatcatcgg tacgcaggtc     360
ctgctgccgc tgctcaagga aggcggcaag gcgcgcgcag ggggcgcctc ggtggtcaac     420
ttctccagcg tcgggggtct gcgcggcgcg gcgttccatg cggcctattg caccagcaag     480
gcggcggtga agatgctctc gaagtgcctc ggcgcggaat cgcggcgct  cggctacaac     540 atccgcgtca actccgtgca tccggcggc  atcgataccc cgatgctcgg ctcgatcatg     600
gacaagtacg tcgaactcgg cgctgccccc tcgcgcgagg tggcccaggc cgcgatggaa     660
atgcgccacc cgatcggtcg catgggtcgc cctgccgaaa tgggcggcgg cgtggtctat     720
ctctgctccg acgcagcaag cttcgtcacc tgcacggaat tcgtgatgga cggcggcttc     780
agccaggtct ga                                                         792

<210> SEQ ID NO 22
<211> LENGTH: 263
<212> TYPE: PRT
<213> ORGANISM: Artificial Sequence
<220> FEATURE:
<223> OTHER INFORMATION: Variant of ketoreductase from Novosphingobium
      aromaticivorans

<400> SEQUENCE: 22

Met Pro Leu Glu Met Thr Ile Ala Leu Asn Asn Val Val Ala Val Val
1               5                   10                  15
```

Thr Gly Ala Ala Gly Gly Ile Gly Arg Glu Leu Val Lys Ala Met Lys
            20                  25                  30

Ala Ala Asn Ala Ile Val Ile Ala Thr Asp Met Ala Pro Ser Ala Asp
            35                  40                  45

Val Glu Gly Ala Asp His Tyr Leu Gln His Asp Val Thr Ser Glu Ala
 50                  55                  60

Gly Trp Lys Ala Val Ala Ala Leu Ala Gln Glu Lys Tyr Gly Arg Val
 65                  70                  75                  80

Asp Ala Leu Val His Asn Ala Gly Ile Ser Ile Val Thr Lys Phe Glu
                85                  90                  95

Asp Thr Pro Leu Ser Asp Phe His Arg Val Asn Thr Val Asn Val Asp
            100                 105                 110

Ser Ile Ile Ile Gly Thr Gln Val Leu Leu Pro Leu Leu Lys Glu Gly
            115                 120                 125

Gly Lys Ala Arg Ala Gly Gly Ala Ser Val Val Asn Phe Ser Ser Val
130                 135                 140

Gly Gly Leu Arg Gly Ala Ala Phe His Ala Ala Tyr Cys Thr Ser Lys
145                 150                 155                 160

Ala Ala Val Lys Met Leu Ser Lys Cys Leu Gly Ala Glu Phe Ala Ala
            165                 170                 175

Leu Gly Tyr Asn Ile Arg Val Asn Ser Val His Pro Gly Gly Ile Asp
            180                 185                 190

Thr Pro Met Leu Gly Ser Ile Met Asp Lys Tyr Val Glu Leu Gly Ala
            195                 200                 205

Ala Pro Ser Arg Glu Val Ala Gln Ala Ala Met Glu Met Arg His Pro
            210                 215                 220

Ile Gly Arg Met Gly Arg Pro Ala Glu Met Gly Gly Val Val Tyr
225                 230                 235                 240

Leu Cys Ser Asp Ala Ala Ser Phe Val Thr Cys Thr Glu Phe Val Met
            245                 250                 255

Asp Gly Gly Phe Ser Gln Val
            260

<210> SEQ ID NO 23
<211> LENGTH: 792
<212> TYPE: DNA
<213> ORGANISM: Artificial Sequence
<220> FEATURE:
<223> OTHER INFORMATION: Variant of ketoreductase from Novosphingobium
      aromaticivorans

<400> SEQUENCE: 23
atgccgcttg aaatgacgat tgctctcaac aatgtggtcg ccgtcgtcac cggcgcggcg     60
ggaggcatcg gccgcgaact ggtcaaggcg atgaaggccg ccaacgccat cgtcatcgcc    120
accgacatgg cgccctcggc cgatgtcgaa ggcgcggacc attatctcca gcacgacgtg    180
acgagcgagg ccggctggaa ggcggtcgcg gcgctggccc aggaaaagta cgggcgcgtc    240
gatgcgctgg tgcacaacgc gggcatctcg atcgtcacga agttcgaaga cactccgctg    300
tccgatttcc accgcgtgaa cacggtcaac gtcgattcca tcatcatcgg tacgcaggtc    360
ctgctgccgc tgctcaagga aggcggcaag gcgcgcgcag ggggcgcctc ggtggtcaac    420
ttctccagcg tcgggggtct gcgcggcggt gcgttcaatg cggcctattg caccagcaag    480
gcggcggtga agatgctctc gaagtgcctc ggcgcggaat cgcggcgct cggctacaac    540 atccgcgtca actccgtgca tccgggcggc atcgataccc cgatgctcgg ctcgatcatg    600

```
gacaagtacg tcgaactcgg cgctgccccc tcgcgcgagg tggcccaggc cgcgatggaa      660
atgcgccacc cgatcggtcg catgggtcgc cctgccgaaa tgggcggcgg cgtggtctat      720
ctctgctccg acgcagcaag cttcgtcacc tgcacggaat tcgtgatgga cggcggcttc      780
agccaggtct ga                                                          792
```

<210> SEQ ID NO 24
<211> LENGTH: 263
<212> TYPE: PRT
<213> ORGANISM: Artificial Sequence
<220> FEATURE:
<223> OTHER INFORMATION: Variant of ketoreductase from Novosphingobium aromaticivorans

<400> SEQUENCE: 24

```
Met Pro Leu Glu Met Thr Ile Ala Leu Asn Asn Val Val Ala Val Val
1               5                   10                  15

Thr Gly Ala Ala Gly Gly Ile Gly Arg Glu Leu Val Lys Ala Met Lys
            20                  25                  30

Ala Ala Asn Ala Ile Val Ile Ala Thr Asp Met Ala Pro Ser Ala Asp
        35                  40                  45

Val Glu Gly Ala Asp His Tyr Leu Gln His Asp Val Thr Ser Glu Ala
    50                  55                  60

Gly Trp Lys Ala Val Ala Ala Leu Ala Gln Glu Lys Tyr Gly Arg Val
65                  70                  75                  80

Asp Ala Leu Val His Asn Ala Gly Ile Ser Ile Val Thr Lys Phe Glu
                85                  90                  95

Asp Thr Pro Leu Ser Asp Phe His Arg Val Asn Thr Val Asn Val Asp
            100                 105                 110

Ser Ile Ile Ile Gly Thr Gln Val Leu Leu Pro Leu Leu Lys Glu Gly
        115                 120                 125

Gly Lys Ala Arg Ala Gly Gly Ala Ser Val Val Asn Phe Ser Ser Val
    130                 135                 140

Gly Gly Leu Arg Gly Gly Ala Phe Asn Ala Ala Tyr Cys Thr Ser Lys
145                 150                 155                 160

Ala Ala Val Lys Met Leu Ser Lys Cys Leu Gly Ala Glu Phe Ala Ala
                165                 170                 175

Leu Gly Tyr Asn Ile Arg Val Asn Ser Val His Pro Gly Gly Ile Asp
            180                 185                 190

Thr Pro Met Leu Gly Ser Ile Met Asp Lys Tyr Val Glu Leu Gly Ala
        195                 200                 205

Ala Pro Ser Arg Glu Val Ala Gln Ala Ala Met Glu Met Arg His Pro
    210                 215                 220

Ile Gly Arg Met Gly Arg Pro Ala Glu Met Gly Gly Val Val Val Tyr
225                 230                 235                 240

Leu Cys Ser Asp Ala Ala Ser Phe Val Thr Cys Thr Glu Phe Val Met
                245                 250                 255

Asp Gly Gly Phe Ser Gln Val
            260
```

<210> SEQ ID NO 25
<211> LENGTH: 792
<212> TYPE: DNA
<213> ORGANISM: Artificial Sequence
<220> FEATURE:
<223> OTHER INFORMATION: Variant of ketoreductase from Novosphingobium aromaticivorans

<400> SEQUENCE: 25

```
atgccgcttg aaatgacgat tgctctcaac aatgtggtcg ccgtcgtcac cggcgcggcg      60
ggaggcatcg gccgcgaact ggtcaaggcg atgaaggccg ccaacgccat cgtcatcgcc     120
accgacatgg cgccctcggc cgatgtcgaa ggcgcggacc attatctcca gcacgacgtg     180
acgagcgagg ccggctggaa ggcggtcgcg gcgctggccc aggaaaagta cgggcgcgtc     240
gatgcgctgt gcacaacgc gggcatctcg ctggtcacga agttcgaaga cactccgctg      300
tccgatttcc accgcgtgaa cacggtcaac gtcgattcca tcatcatcgg tacgcaggtc     360
ctgctgccgc tgctcaagga aggcggcaag gcgcgcgcag ggggcgcctc ggtggtcaac     420
ttctccagcg tcgggggtct gcgcggcgcg gcgttcaatg cggcctattg caccagcaag     480
gcggcggtga agatgctctc gaagtgcctc ggcgcggaat cgcggcgct cggctacaac      540
atccgcgtca actccgtgca tccgggcggc atcgataccc cgatgctcgg ctcgatcatg     600
gacaagtacg tcgaactcgg cgctgccccc tcgcgcgagg tggcccaggc cgcgatggaa     660
atgcgccacc cgatcggtcg catgggtcgc cctgccgaaa tgggcggcgg cgtggtctat     720
ctctgctccg acgcagcaag cttcgtcacc tgcacggaat cgtgatgga cggcggcttc      780
agccaggtct ga                                                         792
```

<210> SEQ ID NO 26
<211> LENGTH: 263
<212> TYPE: PRT
<213> ORGANISM: Artificial Sequence
<220> FEATURE:
<223> OTHER INFORMATION: Variant of ketoreductase from Novosphingobium aromaticivorans

<400> SEQUENCE: 26

```
Met Pro Leu Glu Met Thr Ile Ala Leu Asn Asn Val Ala Val Val
1               5                   10                  15

Thr Gly Ala Ala Gly Gly Ile Gly Arg Glu Leu Val Lys Ala Met Lys
            20                  25                  30

Ala Ala Asn Ala Ile Val Ile Ala Thr Asp Met Ala Pro Ser Ala Asp
        35                  40                  45

Val Glu Gly Ala Asp His Tyr Leu Gln His Asp Val Thr Ser Glu Ala
    50                  55                  60

Gly Trp Lys Ala Val Ala Ala Leu Ala Gln Glu Lys Tyr Gly Arg Val
65                  70                  75                  80

Asp Ala Leu Val His Asn Ala Gly Ile Ser Leu Val Thr Lys Phe Glu
                85                  90                  95

Asp Thr Pro Leu Ser Asp Phe His Arg Val Asn Thr Val Asn Val Asp
            100                 105                 110

Ser Ile Ile Ile Gly Thr Gln Val Leu Leu Pro Leu Leu Lys Glu Gly
        115                 120                 125

Gly Lys Ala Arg Ala Gly Gly Ala Ser Val Val Asn Phe Ser Ser Val
    130                 135                 140

Gly Gly Leu Arg Gly Ala Ala Phe Asn Ala Ala Tyr Cys Thr Ser Lys
145                 150                 155                 160

Ala Ala Val Lys Met Leu Ser Lys Cys Leu Gly Ala Glu Phe Ala Ala
                165                 170                 175

Leu Gly Tyr Asn Ile Arg Val Asn Ser Val His Pro Gly Gly Ile Asp
            180                 185                 190

Thr Pro Met Leu Gly Ser Ile Met Asp Lys Tyr Val Glu Leu Gly Ala
```

```
                195                 200                 205
Ala Pro Ser Arg Glu Val Ala Gln Ala Met Glu Met Arg His Pro
    210                 215                 220

Ile Gly Arg Met Gly Arg Pro Ala Glu Met Gly Gly Val Val Tyr
225                 230                 235                 240

Leu Cys Ser Asp Ala Ala Ser Phe Val Thr Cys Thr Glu Phe Val Met
                245                 250                 255

Asp Gly Gly Phe Ser Gln Val
            260
```

<210> SEQ ID NO 27
<211> LENGTH: 792
<212> TYPE: DNA
<213> ORGANISM: Artificial Sequence
<220> FEATURE:
<223> OTHER INFORMATION: Variant of ketoreductase from Novosphingobium
      aromaticivorans

<400> SEQUENCE: 27

```
atgccgcttg aaatgacgat tgctctcaac aatgtggtcg ccgtcgtcac cggcgcggcg      60
ggaggcatcg gccgcgaact ggtcaaggcg atgaaggccg ccaacgccat cgtcatcgcc     120
accgacatgg cgccctcggc cgatgtcgaa ggcgcggacc attatctcca gcacgacgtg     180
acgagcgagg ccggctggaa ggcggtcgcg gcgctggccc aggaaaagta cgggcgcgtc     240
gatgcgctgg tgcacaacgc gggcatctcg tgggtcacga agttcgaaga cactccgctg     300
tccgatttcc accgcgtgaa cacggtcaac gtcgattcca tcatcatcgg tacgcaggtc     360
ctgctgccgc tgctcaagga aggcggcaag gcgcgcgcag ggggcgcctc ggtggtcaac     420
ttctccagcg tcgggggtct cgcggcgcg gcgttcaatg cggcctattg caccagcaag     480
gcggcggtga agatgctctc gaagtgcctc ggcgcggaat cgcggcgct cggctacaac     540
atccgcgtca actccgtgca tccggcggc atcgataccc cgatgctcgg ctcgatcatg     600
gacaagtacg tcgaactcgg cgctgccccc tcgcgcgagg tgcccaggc cgcgatggaa     660
atgcgccacc cgatcggtcg catgggtcgc cctgccgaaa tgggcggcgg cgtggtctat     720
ctctgctccg acgcagcaag cttcgtcacc tgcacggaat tcgtgatgga cggcggcttc     780
agccaggtct ga                                                        792
```

<210> SEQ ID NO 28
<211> LENGTH: 263
<212> TYPE: PRT
<213> ORGANISM: Artificial Sequence
<220> FEATURE:
<223> OTHER INFORMATION: Variant of ketoreductase from Novosphingobium
      aromaticivorans

<400> SEQUENCE: 28

```
Met Pro Leu Glu Met Thr Ile Ala Leu Asn Asn Val Val Ala Val Val
1               5                   10                  15

Thr Gly Ala Ala Gly Gly Ile Gly Arg Glu Leu Val Lys Ala Met Lys
            20                  25                  30

Ala Ala Asn Ala Ile Val Ile Ala Thr Asp Met Ala Pro Ser Ala Asp
        35                  40                  45

Val Glu Gly Ala Asp His Tyr Leu Gln His Asp Val Thr Ser Glu Ala
    50                  55                  60

Gly Trp Lys Ala Val Ala Ala Leu Ala Gln Glu Lys Tyr Gly Arg Val
65                  70                  75                  80
```

```
Asp Ala Leu Val His Asn Ala Gly Ile Ser Trp Val Thr Lys Phe Glu
            85                  90                  95

Asp Thr Pro Leu Ser Asp Phe His Arg Val Asn Thr Val Asn Val Asp
        100                 105                 110

Ser Ile Ile Ile Gly Thr Gln Val Leu Leu Pro Leu Leu Lys Glu Gly
        115                 120                 125

Gly Lys Ala Arg Ala Gly Gly Ala Ser Val Val Asn Phe Ser Ser Val
    130                 135                 140

Gly Gly Leu Arg Gly Ala Ala Phe Asn Ala Ala Tyr Cys Thr Ser Lys
145                 150                 155                 160

Ala Ala Val Lys Met Leu Ser Lys Cys Leu Gly Ala Glu Phe Ala Ala
                165                 170                 175

Leu Gly Tyr Asn Ile Arg Val Asn Ser Val His Pro Gly Gly Ile Asp
            180                 185                 190

Thr Pro Met Leu Gly Ser Ile Met Asp Lys Tyr Val Glu Leu Gly Ala
        195                 200                 205

Ala Pro Ser Arg Glu Val Ala Gln Ala Ala Met Glu Met Arg His Pro
    210                 215                 220

Ile Gly Arg Met Gly Arg Pro Ala Glu Met Gly Gly Val Val Tyr
225                 230                 235                 240

Leu Cys Ser Asp Ala Ala Ser Phe Val Thr Cys Thr Glu Phe Val Met
                245                 250                 255

Asp Gly Gly Phe Ser Gln Val
            260

<210> SEQ ID NO 29
<211> LENGTH: 792
<212> TYPE: DNA
<213> ORGANISM: Artificial Sequence
<220> FEATURE:
<223> OTHER INFORMATION: Variant of ketoreductase from Novosphingobium
      aromaticivorans

<400> SEQUENCE: 29
atgccgcttg aaatgacgat tgctctcaac aatgtggtcg ccgtcgtcac cggcgcggcg      60
ggaggcatcg gccgcgaact ggtcaaggcg atgaaggccg ccaacgccat cgtcatcgcc     120
accgacatgg cgccctcggc cgatgtcgaa ggcgcggacc attatctcca gcacgacgtg     180
acgagcgagg ccggctggaa ggcggtcgcg gcgctggccc aggaaaagta cgggcgcgtc     240
gatgcgctgg tgcacaacgc gggcatctcg cgggtcacga agttcgaaga cactccgctg     300
tccgatttcc accgcgtgaa cacggtcaac gtcgattcca tcatcatcgg tacgcaggtc     360
ctgctgccgc tgctcaagga aggcggcaag gcgcgcgcag ggggcgcctc ggtggtcaac     420
ttctccagcg tcgggggtct gcgcggcgcg gcgttcaatg cggcctattg caccagcaag     480
gcggcggtga agatgctctc gaagtgcctc ggcgcggaat cgcggcgct cggctacaac     540 atccgcgtca actccgtgca tccgggcggc atcgatacccc cgatgctcgg ctcgatcatg     600
gacaagtacg tcgaactcgg cgctgccccc tcgcgcgagg tggcccaggc cgcgatggaa     660
atgcgccacc cgatcggtcg catgggtcgc cctgccgaaa tgggcggcgg cgtggtctat     720
ctctgctccg acgcagcaag cttcgtcacc tgcacggaat tcgtgatgga cggcggcttc     780
agccaggtct ga                                                         792

<210> SEQ ID NO 30
<211> LENGTH: 263
<212> TYPE: PRT
```

<213> ORGANISM: Artificial Sequence
<220> FEATURE:
<223> OTHER INFORMATION: Variant of ketoreductase from Novosphingobium aromaticivorans

<400> SEQUENCE: 30

```
Met Pro Leu Glu Met Thr Ile Ala Leu Asn Asn Val Val Ala Val Val
1               5                   10                  15

Thr Gly Ala Ala Gly Gly Ile Gly Arg Glu Leu Val Lys Ala Met Lys
            20                  25                  30

Ala Ala Asn Ala Ile Val Ile Ala Thr Asp Met Ala Pro Ser Ala Asp
        35                  40                  45

Val Glu Gly Ala Asp His Tyr Leu Gln His Asp Val Thr Ser Glu Ala
    50                  55                  60

Gly Trp Lys Ala Val Ala Ala Leu Ala Gln Glu Lys Tyr Gly Arg Val
65                  70                  75                  80

Asp Ala Leu Val His Asn Ala Gly Ile Ser Arg Val Thr Lys Phe Glu
                85                  90                  95

Asp Thr Pro Leu Ser Asp Phe His Arg Val Asn Thr Val Asn Val Asp
            100                 105                 110

Ser Ile Ile Ile Gly Thr Gln Val Leu Leu Pro Leu Leu Lys Glu Gly
        115                 120                 125

Gly Lys Ala Arg Ala Gly Gly Ala Ser Val Val Asn Phe Ser Ser Val
    130                 135                 140

Gly Gly Leu Arg Gly Ala Ala Phe Asn Ala Ala Tyr Cys Thr Ser Lys
145                 150                 155                 160

Ala Ala Val Lys Met Leu Ser Lys Cys Leu Gly Ala Glu Phe Ala Ala
                165                 170                 175

Leu Gly Tyr Asn Ile Arg Val Asn Ser Val His Pro Gly Gly Ile Asp
            180                 185                 190

Thr Pro Met Leu Gly Ser Ile Met Asp Lys Tyr Val Glu Leu Gly Ala
        195                 200                 205

Ala Pro Ser Arg Glu Val Ala Gln Ala Ala Met Glu Met Arg His Pro
    210                 215                 220

Ile Gly Arg Met Gly Arg Pro Ala Glu Met Gly Gly Val Val Tyr
225                 230                 235                 240

Leu Cys Ser Asp Ala Ala Ser Phe Val Thr Cys Thr Glu Phe Val Met
                245                 250                 255

Asp Gly Gly Phe Ser Gln Val
            260
```

<210> SEQ ID NO 31
<211> LENGTH: 792
<212> TYPE: DNA
<213> ORGANISM: Artificial Sequence
<220> FEATURE:
<223> OTHER INFORMATION: Variant of ketoreductase from Novosphingobium aromaticivorans

<400> SEQUENCE: 31

```
atgccgcttg aaatgacgat tgctctcaac aatgtggtcg ccgtcgtcac cggcgcggcg    60
ggaggcatcg gccgcgaact ggtcaaggcg atgaaggccg ccaacgccat cgtcatcgcc   120
accgacatgg cgccctcggc cgatgtcgaa ggcgcggacc attatctcca gcacgacgtg   180
acgagcgagg ccggctggaa ggcggtcgcg gcgctggccc aggaaaagta cgggcgcgtc   240
gatgcgctgg tgcacaacgc gggcatctcg aaggtcacga gttcgaaga cactccgctg   300
```

```
tccgatttcc accgcgtgaa cacggtcaac gtcgattcca tcatcatcgg tacgcaggtc    360
ctgctgccgc tgctcaagga aggcggcaag gcgcgcgcag ggggcgcctc ggtggtcaac    420
ttctccagcg tcgggggtct gcgcggcgcg gcgttcaatg cggcctattg caccagcaag    480
gcggcggtga agatgctctc gaagtgcctc ggcgcggaat cgcggcgct cggctacaac     540 atccgcgtca actccgtgca tccgggcggc atcgataccc cgatgctcgg ctcgatcatg    600
gacaagtacg tcgaactcgg cgctgccccc tcgcgcgagg tggcccaggc cgcgatggaa    660
atgcgccacc cgatcggtcg catgggtcgc cctgccgaaa tgggcggcgg cgtggtctat    720
ctctgctccg acgcagcaag cttcgtcacc tgcacggaat cgtgatggaa cggcggcttc    780
agccaggtct ga                                                        792
```

<210> SEQ ID NO 32
<211> LENGTH: 263
<212> TYPE: PRT
<213> ORGANISM: Artificial Sequence
<220> FEATURE:
<223> OTHER INFORMATION: Variant of ketoreductase from Novosphingobium aromaticivorans

<400> SEQUENCE: 32

```
Met Pro Leu Glu Met Thr Ile Ala Leu Asn Asn Val Val Ala Val Val
1               5                   10                  15

Thr Gly Ala Ala Gly Gly Ile Gly Arg Glu Leu Val Lys Ala Met Lys
            20                  25                  30

Ala Ala Asn Ala Ile Val Ile Ala Thr Asp Met Ala Pro Ser Ala Asp
        35                  40                  45

Val Glu Gly Ala Asp His Tyr Leu Gln His Val Thr Ser Glu Ala
    50                  55                  60

Gly Trp Lys Ala Val Ala Ala Leu Ala Gln Glu Lys Tyr Gly Arg Val
65                  70                  75                  80

Asp Ala Leu Val His Asn Ala Gly Ile Ser Lys Val Thr Lys Phe Glu
                85                  90                  95

Asp Thr Pro Leu Ser Asp Phe His Arg Val Asn Thr Val Asn Val Asp
            100                 105                 110

Ser Ile Ile Ile Gly Thr Gln Val Leu Leu Pro Leu Leu Lys Glu Gly
        115                 120                 125

Gly Lys Ala Arg Ala Gly Gly Ala Ser Val Val Asn Phe Ser Ser Val
    130                 135                 140

Gly Gly Leu Arg Gly Ala Ala Phe Asn Ala Ala Tyr Cys Thr Ser Lys
145                 150                 155                 160

Ala Ala Val Lys Met Leu Ser Lys Cys Leu Gly Ala Glu Phe Ala Ala
                165                 170                 175

Leu Gly Tyr Asn Ile Arg Val Asn Ser Val His Pro Gly Gly Ile Asp
            180                 185                 190

Thr Pro Met Leu Gly Ser Ile Met Asp Lys Tyr Val Glu Leu Gly Ala
        195                 200                 205

Ala Pro Ser Arg Glu Val Ala Gln Ala Ala Met Glu Met Arg His Pro
    210                 215                 220

Ile Gly Arg Met Gly Arg Pro Ala Glu Met Gly Gly Val Val Tyr
225                 230                 235                 240

Leu Cys Ser Asp Ala Ala Ser Phe Val Thr Cys Thr Glu Phe Val Met
                245                 250                 255

Asp Gly Gly Phe Ser Gln Val
            260
```

<210> SEQ ID NO 33
<211> LENGTH: 792
<212> TYPE: DNA
<213> ORGANISM: Artificial Sequence
<220> FEATURE:
<223> OTHER INFORMATION: Variant of ketoreductase from Novosphingobium aromaticivorans

<400> SEQUENCE: 33

```
atgccgcttg aaatgacgat tgctctcaac aatgtggtcg ccgtcgtcac cggcgcggcg      60
ggaggcatcg gccgcgaact ggtcaaggcg atgaaggccg ccaacgccat cgtcatcgcc     120
accgacatgg cgccctcggc cgatgtcgaa ggcgcggacc attatctcca gcacgacgtg     180
acgagcgagg ccggctggaa ggcggtcgcg gcgctggccc aggaaaagta cgggcgcgtc     240
gatgcgctgg tgcacaacgc gggcatctcg atcgtcacga gttcgaaga cactccgctg      300
tccgatttcc accgcgtgaa cacggtcaac gtcgattcca tcatcatcgg tacgcaggtc     360
ctgctgccgc tgctcaagga aggcggcaag gcgcgcgcag ggggcgcctc ggtggtcaac     420
ttctccagca cgggggggtct gcgcggcgcg gcgttcaatg cggcctattg caccagcaag     480
gcggcggtga agatgctctc gaagtgcctc ggcgcggaat cgcggcgct cggctacaac     540
atccgcgtca actccgtgca tccgggcggc atcgataccc cgatgctcgg ctcgatcatg     600
gacaagtacg tcgaactcgg cgctgccccc tcgcgcgagg tggcccaggc cgcgatggaa     660
atgcgccacc cgatcggtcg catgggtcgc cctgccgaaa tgggcggcgg cgtggtctat     720
ctctgctccg acgcagcaag cttcgtcacc tgcacggaat tcgtgatgga cggcggcttc     780
agccaggtct ga                                                         792
```

<210> SEQ ID NO 34
<211> LENGTH: 263
<212> TYPE: PRT
<213> ORGANISM: Artificial Sequence
<220> FEATURE:
<223> OTHER INFORMATION: Variant of ketoreductase from Novosphingobium aromaticivorans

<400> SEQUENCE: 34

```
Met Pro Leu Glu Met Thr Ile Ala Leu Asn Asn Val Val Ala Val Val
1               5                   10                  15

Thr Gly Ala Ala Gly Gly Ile Gly Arg Glu Leu Val Lys Ala Met Lys
            20                  25                  30

Ala Ala Asn Ala Ile Val Ile Ala Thr Asp Met Ala Pro Ser Ala Asp
        35                  40                  45

Val Glu Gly Ala Asp His Tyr Leu Gln His Asp Val Thr Ser Glu Ala
    50                  55                  60

Gly Trp Lys Ala Val Ala Ala Leu Ala Gln Glu Lys Tyr Gly Arg Val
65                  70                  75                  80

Asp Ala Leu Val His Asn Ala Gly Ile Ser Ile Val Thr Lys Phe Glu
                85                  90                  95

Asp Thr Pro Leu Ser Asp Phe His Arg Val Asn Thr Val Asn Val Asp
            100                 105                 110

Ser Ile Ile Ile Gly Thr Gln Val Leu Leu Pro Leu Leu Lys Glu Gly
        115                 120                 125

Gly Lys Ala Arg Ala Gly Gly Ala Ser Val Val Asn Phe Ser Ser Thr
    130                 135                 140

Gly Gly Leu Arg Gly Ala Ala Phe Asn Ala Ala Tyr Cys Thr Ser Lys
```

```
                145                 150                 155                 160
Ala Ala Val Lys Met Leu Ser Lys Cys Leu Gly Ala Glu Phe Ala Ala
                    165                 170                 175

Leu Gly Tyr Asn Ile Arg Val Asn Ser Val His Pro Gly Gly Ile Asp
                180                 185                 190

Thr Pro Met Leu Gly Ser Ile Met Asp Lys Tyr Val Glu Leu Gly Ala
            195                 200                 205

Ala Pro Ser Arg Glu Val Ala Gln Ala Ala Met Glu Met Arg His Pro
        210                 215                 220

Ile Gly Arg Met Gly Arg Pro Ala Glu Met Gly Gly Val Val Tyr
225                 230                 235                 240

Leu Cys Ser Asp Ala Ala Ser Phe Val Thr Cys Thr Glu Phe Val Met
                245                 250                 255

Asp Gly Gly Phe Ser Gln Val
            260

<210> SEQ ID NO 35
<211> LENGTH: 792
<212> TYPE: DNA
<213> ORGANISM: Artificial Sequence
<220> FEATURE:
<223> OTHER INFORMATION: Variant of ketoreductase from Novosphingobium
      aromaticivorans

<400> SEQUENCE: 35
atgccgcttg aaatgacgat tgctctcaac aatgtggtcg ccgtcgtcac cggcgcggcg       60
ggaggcatcg gccgcgaact ggtcaaggcg atgaaggccg ccaacgccat tgtcatcgcc      120
accgacatgg cgccctcggc cgatgtcgaa ggcgcggacc attatctcca gcacgacgtg      180
acgagcgagg ccggctggaa ggcggtcgcg gcgctggccc aggaaaagta cgggcgcgtc      240
gatgcgctgg tgcacaacgc gggcatctcg atcgtcacga agttcgaaga cactccgctg      300
tccgatttcc accgcgtgaa cacggtcaac gtcgattcca tcatcatcgg tacgcaggtc      360
ctgctgccgc tgctcaagga aggcggcaag gcgcgcgcag ggggcgcctc ggtggtcaac      420
ttctccagcg tcgggggtct gcgcggcggt gcgttcaatg cggcctattg caccagcaag      480
gcggcggtga agatgctctc gaagtgcctc ggcgcggaat cgcggcgct cggctacaac      540
atccgcgtca actccgtgca tccgggcggc atcgataccc cgatgctcgg ctcgatcatg      600
gacaagtacg tcgaactcgg cgctgccccc tcgcgcgagg tggcccaggc cgcgatggaa      660
atgcgccacc cgatcggtcg catgggtcgc cctgccgaaa tgggcggcgg cgtggtctat      720
ctctgctccg acgcagcaag cttcgtcacc tgcacggaat tcgtgatgga cggcggcttc      780
agccaggtct ga                                                          792

<210> SEQ ID NO 36
<211> LENGTH: 263
<212> TYPE: PRT
<213> ORGANISM: Artificial Sequence
<220> FEATURE:
<223> OTHER INFORMATION: Variant of ketoreductase from Novosphingobium
      aromaticivorans

<400> SEQUENCE: 36

Met Pro Leu Glu Met Thr Ile Ala Leu Asn Asn Val Val Ala Val Val
1               5                   10                  15

Thr Gly Ala Ala Gly Gly Ile Gly Arg Glu Leu Val Lys Ala Met Lys
            20                  25                  30
```

```
Ala Ala Asn Ala Ile Val Ile Ala Thr Asp Met Ala Pro Ser Ala Asp
            35                  40                  45

Val Glu Gly Ala Asp His Tyr Leu Gln His Asp Val Thr Ser Glu Ala
 50                  55                  60

Gly Trp Lys Ala Val Ala Leu Ala Gln Glu Lys Tyr Gly Arg Val
 65                  70                  75                  80

Asp Ala Leu Val His Asn Ala Gly Ile Ser Ile Val Thr Lys Phe Glu
                85                  90                  95

Asp Thr Pro Leu Ser Asp Phe His Arg Val Asn Thr Val Asn Val Asp
               100                 105                 110

Ser Ile Ile Ile Gly Thr Gln Val Leu Leu Pro Leu Leu Lys Glu Gly
               115                 120                 125

Gly Lys Ala Arg Ala Gly Gly Ala Ser Val Val Asn Phe Ser Ser Val
130                 135                 140

Gly Gly Leu Arg Gly Gly Ala Phe Asn Ala Ala Tyr Cys Thr Ser Lys
145                 150                 155                 160

Ala Ala Val Lys Met Leu Ser Lys Cys Leu Gly Ala Glu Phe Ala Ala
                165                 170                 175

Leu Gly Tyr Asn Ile Arg Val Asn Ser Val His Pro Gly Gly Ile Asp
                180                 185                 190

Thr Pro Met Leu Gly Ser Ile Met Asp Lys Tyr Val Glu Leu Gly Ala
                195                 200                 205

Ala Pro Ser Arg Glu Val Ala Gln Ala Ala Met Glu Met Arg His Pro
               210                 215                 220

Ile Gly Arg Met Gly Arg Pro Ala Glu Met Gly Gly Val Val Tyr
225                 230                 235                 240

Leu Cys Ser Asp Ala Ala Ser Phe Val Thr Cys Thr Glu Phe Val Met
                245                 250                 255

Asp Gly Gly Phe Ser Gln Val
                260

<210> SEQ ID NO 37
<211> LENGTH: 792
<212> TYPE: DNA
<213> ORGANISM: Artificial Sequence
<220> FEATURE:
<223> OTHER INFORMATION: Variant of ketoreductase from Novosphingobium
      aromaticivorans

<400> SEQUENCE: 37
atgccgcttg aaatgacgat tgctctcaac aatgtggtcg ccgtcgtcac cggcgcggcg      60
ggaggcatcg gccgcgaact ggtcaaggcg atgaaggccg ccaacgccat cgtcatcgcc     120
accgacatgg cgccctcggc cgatgtcgaa ggcgcggacc attatctcca gcacgacgtg     180
acgagcgagg ccggctggaa ggcggtcgcg gcgctggccc aggaaaagta cgggcgcgtc     240
gatgcgctgg tgcacaacgc gggcatctcg atcgtcacga gttcgaaga  cactccgctg     300
tccgatttcc accgcgtgaa cacggtcaac gtcgattcca tcatcatcgg tacgcaggtc     360
ctgctgccgc tgctcaagga aggcggcaag gcgcgcgcag gggcgcctc  ggtggtcaac     420
ttctccagcg tcgggggtct cgcggcgcg  cgttcaatg  cggcctattg caccagcaag     480
gcggcggtga agatgctctc gaagtgcctc ggcgcggaat cggcggcgct cggctacaac     540
atccgcgtca actccgtgca tccgggcgag atcgataccc cgatgctcgg ctcgatcatg     600
gacaagtacg tcgaactcgg cgctgccccc tcgcgcgagg tggcccaggc cgcgatggaa     660
atgcgccacc cgatcggtcg catgggtcgc cctgccgaaa tgggcggcgg cgtggtctat     720
```

```
ctctgctccg acgcagcaag cttcgtcacc tgcacggaat tcgtgatgga cggcggcttc    780
agccaggtct ga                                                        792
```

<210> SEQ ID NO 38
<211> LENGTH: 263
<212> TYPE: PRT
<213> ORGANISM: Artificial Sequence
<220> FEATURE:
<223> OTHER INFORMATION: Variant of ketoreductase from Novosphingobium
      aromaticivorans

<400> SEQUENCE: 38

```
Met Pro Leu Glu Met Thr Ile Ala Leu Asn Asn Val Val Ala Val Val
1               5                   10                  15

Thr Gly Ala Ala Gly Gly Ile Gly Arg Glu Leu Val Lys Ala Met Lys
            20                  25                  30

Ala Ala Asn Ala Ile Val Ile Ala Thr Asp Met Ala Pro Ser Ala Asp
        35                  40                  45

Val Glu Gly Ala Asp His Tyr Leu Gln His Asp Val Thr Ser Glu Ala
    50                  55                  60

Gly Trp Lys Ala Val Ala Ala Leu Ala Gln Glu Lys Tyr Gly Arg Val
65                  70                  75                  80

Asp Ala Leu Val His Asn Ala Gly Ile Ser Ile Val Thr Lys Phe Glu
                85                  90                  95

Asp Thr Pro Leu Ser Asp Phe His Arg Val Asn Thr Val Asn Val Asp
            100                 105                 110

Ser Ile Ile Ile Gly Thr Gln Val Leu Leu Pro Leu Leu Lys Glu Gly
        115                 120                 125

Gly Lys Ala Arg Ala Gly Gly Ala Ser Val Val Asn Phe Ser Ser Val
    130                 135                 140

Gly Gly Leu Arg Gly Ala Ala Phe Asn Ala Ala Tyr Cys Thr Ser Lys
145                 150                 155                 160

Ala Ala Val Lys Met Leu Ser Lys Cys Leu Gly Ala Glu Phe Ala Ala
                165                 170                 175

Leu Gly Tyr Asn Ile Arg Val Asn Ser Val His Pro Gly Glu Ile Asp
            180                 185                 190

Thr Pro Met Leu Gly Ser Ile Met Asp Lys Tyr Val Glu Leu Gly Ala
        195                 200                 205

Ala Pro Ser Arg Glu Val Ala Gln Ala Ala Met Glu Met Arg His Pro
    210                 215                 220

Ile Gly Arg Met Gly Arg Pro Ala Glu Met Gly Gly Val Val Tyr
225                 230                 235                 240

Leu Cys Ser Asp Ala Ala Ser Phe Val Thr Cys Thr Glu Phe Val Met
                245                 250                 255

Asp Gly Gly Phe Ser Gln Val
            260
```

<210> SEQ ID NO 39
<211> LENGTH: 792
<212> TYPE: DNA
<213> ORGANISM: Artificial Sequence
<220> FEATURE:
<223> OTHER INFORMATION: Variant of ketoreductase from Novosphingobium
      aromaticivorans

<400> SEQUENCE: 39

```
atgccgcttg aaatgacgat tgctctcaac aatgtggtcg ccgtcgtcac cggcgcggcg    60
```

-continued

```
ggaggcatcg gccgcgaact ggtcaaggcg atgaaggccg ccaacgccat cgtcatcgcc      120
accgacatgg cgccctcggc cgatgtcgaa ggcgcggacc attatctcca gcacgacgtg      180
acgagcgagg ccggctggaa ggcggtcgcg gcgctggccc aggaaaagta cgggcgcgtc      240
gatgcgctgg tgcacaacgc gggcatctcg atcgtcacga agttcgaaga cactccgctg      300
tccgatttcc accgcgtgaa cacggtcaac gtcgattcca tcatcatcgg tacgcaggtc      360
ctgctgccgc tgctcaagga aggcggcaag gcgcgcgcag ggggcgcctc ggtggtcaac      420
ttctccagcg tcggggtct gcgcggcgcg gcgttcaatg cggcctattg caccagcaag      480
gcggcggtga agatgctctc gaagtgcctc ggcgcggaat cgcggcgct cggctacaac      540 atccgcgtca actccgtgca tccgggcggc atcgataccc cgatgctcgg ctcgatcatg      600
gacaagtacg tcgaactcgg cgctgccccc tcgcgcgagg tggcccaggc cgcgatggaa      660
atgcgccacc cgatcggtcg catgggtcgc cctgccgaaa tgggcggcgg cgtggtctat      720
ctctgctccg acgcagcaag cttcgtcacc tgcacggaat cgtgatggga cggcggcttc      780
agccaggtct ga                                                         792
```

<210> SEQ ID NO 40  
<211> LENGTH: 263  
<212> TYPE: PRT  
<213> ORGANISM: Artificial Sequence  
<220> FEATURE:  
<223> OTHER INFORMATION: Variant of ketoreductase from Novosphingobium aromaticivorans

<400> SEQUENCE: 40

```
Met Pro Leu Glu Met Thr Ile Ala Leu Asn Asn Val Ala Val Val
1               5                   10                  15

Thr Gly Ala Ala Gly Gly Ile Gly Arg Glu Leu Val Lys Ala Met Lys
            20                  25                  30

Ala Ala Asn Ala Ile Val Ile Ala Thr Asp Met Ala Pro Ser Ala Asp
        35                  40                  45

Val Glu Gly Ala Asp His Tyr Leu Gln His Asp Val Thr Ser Glu Ala
    50                  55                  60

Gly Trp Lys Ala Val Ala Ala Leu Ala Gln Glu Lys Tyr Gly Arg Val
65                  70                  75                  80

Asp Ala Leu Val His Asn Ala Gly Ile Ser Ile Val Thr Lys Phe Glu
                85                  90                  95

Asp Thr Pro Leu Ser Asp Phe His Arg Val Asn Thr Val Asn Val Asp
            100                 105                 110

Ser Ile Ile Ile Gly Thr Gln Val Leu Leu Pro Leu Leu Lys Glu Gly
        115                 120                 125

Gly Lys Ala Arg Ala Gly Gly Ala Ser Val Val Asn Phe Ser Ser Val
    130                 135                 140

Gly Gly Leu Arg Gly Ala Ala Phe Asn Ala Ala Tyr Cys Thr Ser Lys
145                 150                 155                 160

Ala Ala Val Lys Met Leu Ser Lys Cys Leu Gly Ala Glu Phe Ala Ala
                165                 170                 175

Leu Gly Tyr Asn Ile Arg Val Asn Ser Val His Pro Gly Gly Ile Asp
            180                 185                 190

Thr Pro Met Leu Gly Ser Ile Met Asp Lys Tyr Val Glu Leu Gly Ala
        195                 200                 205

Ala Pro Ser Arg Glu Val Ala Gln Ala Ala Met Glu Met Arg His Pro
    210                 215                 220
```

Ile Gly Arg Met Gly Arg Pro Ala Glu Met Gly Gly Val Val Tyr
225                 230                 235                 240

Leu Cys Ser Asp Ala Ala Ser Phe Val Thr Cys Thr Glu Phe Val Met
            245                 250                 255

Asp Gly Gly Phe Ser Gln Val
            260

<210> SEQ ID NO 41
<211> LENGTH: 792
<212> TYPE: DNA
<213> ORGANISM: Artificial Sequence
<220> FEATURE:
<223> OTHER INFORMATION: Variant of ketoreductase from Novosphingobium
      aromaticivorans

<400> SEQUENCE: 41

```
atgccgcttg aaatgacgat tgctctcaac aatgtggtcg ccgtcgtcac cggcgcggcg      60
ggaggcatcg gccgcgaact ggtcaaggcg atgaaggccg ccaacgccat cgtcatcgcc     120
accgacatgg cgccctcggc cgatgtcgaa ggcgcggacc attatctcca gcacgacgtg     180
acgagcgagg ccggctggaa ggcggtcgcg gcgctggccc aggaaaagta cgggcgcgtc     240
gatgcgctgg tgcacaacgc gggcatctcg atcgtcacga gttcgaaga cactccgctg      300
tccgatttcc accgcgtgaa cacggtcaac gtcgattcca tcatcatcgg tacgcaggtc     360
ctgctgccgc tgctcaagga aggcggcaag gcgcgcgcag ggggcgcctc ggtggtcaac     420
ttctccagcg tcggggggtct gcgcggcgcg gcgttcaatg cggcctattg caccagcaag     480
gcggcggtga agatgctctc gaagtgcctc ggcgcggaat cgcggcgct cggctacaac     540
atccgcgtca actccgtgca tccggcggc atcgataccc cgatgctcgg caatatcatg     600
gacaagtacg tcgaactcgg cgctgccccc tcgcgcgagg tgcccaggc cgcgatggaa     660
atgcgccacc cgatcggtcg catgggtcgc cctgccgaaa tgggcggcgg cgtggtctat     720
ctctgctccg acgcagcaag cttcgtcacc tgcacggaat tcgtgatgga cggcggcttc     780
agccaggtct ga                                                         792
```

<210> SEQ ID NO 42
<211> LENGTH: 263
<212> TYPE: PRT
<213> ORGANISM: Artificial Sequence
<220> FEATURE:
<223> OTHER INFORMATION: Variant of ketoreductase from Novosphingobium
      aromaticivorans

<400> SEQUENCE: 42

Met Pro Leu Glu Met Thr Ile Ala Leu Asn Asn Val Val Ala Val Val
1               5                   10                  15

Thr Gly Ala Ala Gly Gly Ile Gly Arg Glu Leu Val Lys Ala Met Lys
            20                  25                  30

Ala Ala Asn Ala Ile Val Ile Ala Thr Asp Met Ala Pro Ser Ala Asp
        35                  40                  45

Val Glu Gly Ala Asp His Tyr Leu Gln His Asp Val Thr Ser Glu Ala
    50                  55                  60

Gly Trp Lys Ala Val Ala Leu Ala Gln Glu Lys Tyr Gly Arg Val
65                  70                  75                  80

Asp Ala Leu Val His Asn Ala Gly Ile Ser Ile Val Thr Lys Phe Glu
                85                  90                  95

Asp Thr Pro Leu Ser Asp Phe His Arg Val Asn Thr Val Asn Val Asp

```
                    100                 105                 110
Ser Ile Ile Ile Gly Thr Gln Val Leu Leu Pro Leu Leu Lys Glu Gly
        115                 120                 125

Gly Lys Ala Arg Ala Gly Gly Ala Ser Val Val Asn Phe Ser Ser Val
    130                 135                 140

Gly Gly Leu Arg Gly Ala Ala Phe Asn Ala Ala Tyr Cys Thr Ser Lys
145                 150                 155                 160

Ala Ala Val Lys Met Leu Ser Lys Cys Leu Gly Ala Glu Phe Ala Ala
                165                 170                 175

Leu Gly Tyr Asn Ile Arg Val Asn Ser Val His Pro Gly Gly Ile Asp
            180                 185                 190

Thr Pro Met Leu Gly Asn Ile Met Asp Lys Tyr Val Glu Leu Gly Ala
        195                 200                 205

Ala Pro Ser Arg Glu Val Ala Gln Ala Ala Met Glu Met Arg His Pro
    210                 215                 220

Ile Gly Arg Met Gly Arg Pro Ala Glu Met Gly Gly Val Val Tyr
225                 230                 235                 240

Leu Cys Ser Asp Ala Ala Ser Phe Val Thr Cys Thr Glu Phe Val Met
                245                 250                 255

Asp Gly Gly Phe Ser Gln Val
            260
```

<210> SEQ ID NO 43
<211> LENGTH: 792
<212> TYPE: DNA
<213> ORGANISM: Artificial Sequence
<220> FEATURE:
<223> OTHER INFORMATION: Variant of ketoreductase from Novosphingobium
   aromaticivorans

<400> SEQUENCE: 43

```
atgccgcttg aaatgacgat tgctctcaac aatgtggtcg ccgtcgtcac cggcgcggcg      60
ggaggcatcg gccgcgaact ggtcaaggcg atgaaggccg ccaacgccat cgtcatcgcc     120
accgacatgg cgccctcggc cgatgtcgaa ggcgcggacc attatctcca gcacgacgtg     180
acgagcgagg ccggctggaa ggcggtcgcg gcgctggccc aggaaaagta cgggcgcgtc     240
gatgcgctgg tgcacaacgc gggcatctcg atcgtcacga gttcgaagac cactccgctg     300
tccgatttcc accgcgtgaa cacggtcaac gtcgattcca tcatcatcgg tacgcaggtc     360
ctgctgccgc tgctcaagga aggcggcaag gcgcgcgcag ggggcgcctc ggtggtcaac     420
ttctccagcg tcgggggtct cgcgggcgcg gcgttcaatg cggcctattg caccagcaag     480
gcggcggtga agatgctctc gaagtgcctc ggcgcggaat cgcggcgct cggctacaac     540
atccgcgtca actccgtgca tccgggcggc atcgataccc cgatgctcgg ctcgatcatt     600
gacaagtacg tcgaactcgg cgctgccccc tcgcgcgagg tggcccaggc cgcgatggaa     660
atgcgccacc cgatcggtcg catgggtcgc cctgccgaaa tgggcggcgg cgtggtctat     720
ctctgctccg acgcagcaag cttcgtcacc tgcacggaat tcgtgatgga cggcggcttc     780
agccaggtct ga                                                         792
```

<210> SEQ ID NO 44
<211> LENGTH: 263
<212> TYPE: PRT
<213> ORGANISM: Artificial Sequence
<220> FEATURE:
<223> OTHER INFORMATION: Variant of ketoreductase from Novosphingobium
   aromaticivorans

<400> SEQUENCE: 44

```
Met Pro Leu Glu Met Thr Ile Ala Leu Asn Asn Val Val Ala Val Val
1               5                   10                  15

Thr Gly Ala Ala Gly Gly Ile Gly Arg Glu Leu Val Lys Ala Met Lys
            20                  25                  30

Ala Ala Asn Ala Ile Val Ile Ala Thr Asp Met Ala Pro Ser Ala Asp
        35                  40                  45

Val Glu Gly Ala Asp His Tyr Leu Gln His Asp Val Thr Ser Glu Ala
50                  55                  60

Gly Trp Lys Ala Val Ala Ala Leu Ala Gln Glu Lys Tyr Gly Arg Val
65                  70                  75                  80

Asp Ala Leu Val His Asn Ala Gly Ile Ser Ile Val Thr Lys Phe Glu
                85                  90                  95

Asp Thr Pro Leu Ser Asp Phe His Arg Val Asn Thr Val Asn Val Asp
            100                 105                 110

Ser Ile Ile Ile Gly Thr Gln Val Leu Pro Leu Leu Lys Glu Gly
            115                 120                 125

Gly Lys Ala Arg Ala Gly Gly Ala Ser Val Val Asn Phe Ser Ser Val
    130                 135                 140

Gly Gly Leu Arg Gly Ala Ala Phe Asn Ala Ala Tyr Cys Thr Ser Lys
145                 150                 155                 160

Ala Ala Val Lys Met Leu Ser Lys Cys Leu Gly Ala Glu Phe Ala Ala
                165                 170                 175

Leu Gly Tyr Asn Ile Arg Val Asn Ser Val His Pro Gly Gly Ile Asp
            180                 185                 190

Thr Pro Met Leu Gly Ser Ile Ile Asp Lys Tyr Val Glu Leu Gly Ala
        195                 200                 205

Ala Pro Ser Arg Glu Val Ala Gln Ala Ala Met Glu Met Arg His Pro
    210                 215                 220

Ile Gly Arg Met Gly Arg Pro Ala Glu Met Gly Gly Val Val Tyr
225                 230                 235                 240

Leu Cys Ser Asp Ala Ala Ser Phe Val Thr Cys Thr Glu Phe Val Met
                245                 250                 255

Asp Gly Gly Phe Ser Gln Val
            260
```

<210> SEQ ID NO 45
<211> LENGTH: 792
<212> TYPE: DNA
<213> ORGANISM: Artificial Sequence
<220> FEATURE:
<223> OTHER INFORMATION: Variant of ketoreductase from Novosphingobium aromaticivorans

<400> SEQUENCE: 45

```
atgccgcttg aaatgacgat tgctctcaac aatgtggtcg ccgtcgtcac cggcgcggcg      60
ggaggcatcg gccgcgaact ggtcaaggcg atgaaggccg ccaacgccat cgtcatcgcc     120
accgacatgg cgccctcggc tgatgtcgaa ggcgcggacc attatctcca gcacgacgtg     180
acgagcgagg ccggctggaa ggcggtcgcg gcgctggccc aggaaaagta cgggcgcgtc     240
gatgcgctgg tgcacaacgc gggcatctcg atcgtcacga agttcgaaga cactccgctg     300
tccgatttcc accgcgtgaa cacggtcaac gtcgattcca tcatcatcgg tacgcaggtc     360
ctgctgccgc tgctcaagga aggcggcaag gcgcgcgcag ggggcgcctc ggtggtcaac     420
```

```
ttctccagcg tcgcgggtct gcgcggcgcg gcgttcaatg cggcctattg caccagcaag    480
gcggcggtga agatgctctc gaagtgcctc ggcgcggaat tcgcggcgct cggctacaac    540
atccgcgtca actccgtgca tccgggcggc atcgataccc cgatgctcgg ctcgatcatg    600
gacaagtacg tcgaactcgg cgctgccccc tcgcgcgagg tggcccaggc cgcgatggaa    660
atgcgccacc cgatcggtcg catgggtcgc cctgccgaaa tgggcggcgg cgtggtctat    720
ctctgctccg acgcagcaag cttcgtcacc tgcacggaat cgtgatgga cggcggcttc    780 agccaggtct ga                                                         792
```

<210> SEQ ID NO 46
<211> LENGTH: 263
<212> TYPE: PRT
<213> ORGANISM: Artificial Sequence
<220> FEATURE:
<223> OTHER INFORMATION: Variant of ketoreductase from Novosphingobium aromaticivorans

<400> SEQUENCE: 46

```
Met Pro Leu Glu Met Thr Ile Ala Leu Asn Asn Val Val Ala Val Val
1               5                   10                  15

Thr Gly Ala Ala Gly Gly Ile Gly Arg Glu Leu Val Lys Ala Met Lys
            20                  25                  30

Ala Ala Asn Ala Ile Val Ile Ala Thr Asp Met Ala Pro Ser Ala Asp
        35                  40                  45

Val Glu Gly Ala Asp His Tyr Leu Gln His Asp Val Thr Ser Glu Ala
    50                  55                  60

Gly Trp Lys Ala Val Ala Leu Ala Gln Lys Tyr Gly Arg Val
65                  70                  75                  80

Asp Ala Leu Val His Asn Ala Gly Ile Ser Ile Val Thr Lys Phe Glu
                85                  90                  95

Asp Thr Pro Leu Ser Asp Phe His Arg Val Asn Thr Val Asn Val Asp
            100                 105                 110

Ser Ile Ile Ile Gly Thr Gln Val Leu Leu Pro Leu Leu Lys Glu Gly
        115                 120                 125

Gly Lys Ala Arg Ala Gly Gly Ala Ser Val Val Asn Phe Ser Ser Val
    130                 135                 140

Ala Gly Leu Arg Gly Ala Ala Phe Asn Ala Ala Tyr Cys Thr Ser Lys
145                 150                 155                 160

Ala Ala Val Lys Met Leu Ser Lys Cys Leu Gly Ala Glu Phe Ala Ala
                165                 170                 175

Leu Gly Tyr Asn Ile Arg Val Asn Ser Val His Pro Gly Gly Ile Asp
            180                 185                 190

Thr Pro Met Leu Gly Ser Ile Met Asp Lys Tyr Val Glu Leu Gly Ala
        195                 200                 205

Ala Pro Ser Arg Glu Val Ala Gln Ala Ala Met Glu Met Arg His Pro
    210                 215                 220

Ile Gly Arg Met Gly Arg Pro Ala Glu Met Gly Gly Val Val Tyr
225                 230                 235                 240

Leu Cys Ser Asp Ala Ala Ser Phe Val Thr Cys Thr Glu Phe Val Met
                245                 250                 255

Asp Gly Gly Phe Ser Gln Val
            260
```

<210> SEQ ID NO 47
<211> LENGTH: 792

<212> TYPE: DNA
<213> ORGANISM: Artificial Sequence
<220> FEATURE:
<223> OTHER INFORMATION: Variant of ketoreductase from Novosphingobium aromaticivorans

<400> SEQUENCE: 47

```
atgccgcttg aaatgacgat tgctctcaac aatgtggtcg ccgtcgtcac cggcgcggcg    60
ggaggcatcg gccgcgaact ggtcaaggcg atgaaggccg ccaacgccat cgtcatcgcc   120
accgacatgg cgccctcggc cgatgtcgaa ggcgcggacc attatctcca gcacgacgtg   180
acgagcgagg ccggctggaa ggcggtcgcg gcgctggccc aggaaaagta cgggcgcgtc   240
gatgcgctgg tgcacaacgc gggcatctcg atcgtcacga agttcgaaga cactccgctg   300
tccgatttcc accgcgtgaa cacggtcaac gtcgattcca tcatcatcgg tacgcaggtc   360
ctgctgccgc tgctcaagga aggcggcaag gcgcgcgcag ggggcgcctc ggtggtcaac   420
ttctccagcg tcgcgggtct cgcggcgcg gcgttcaatg cggcctattg caccagcaag   480
gcggcggtga agatgctctc gaagtgcctc ggcgcggaat cgcggcgct cggctacaac   540
atccgcgtca actccgtgca tccgggcggc atcgataccc cgatgctcgg ctcgatcatg   600
gacaagtacg tcgaactcgg cgctgccccc tcgcgcgagg tggcccaggc cgcgatggaa   660
atgcgccacc cgatcggtcg catgggtcgc cctgccgaaa tgggcggcgg cgtggtctat   720
ctctgctccg acgcagcaag cttcgtcacc tgcacggaat cgtgatgga cggcggcttc   780
agccaggtct ga                                                        792
```

<210> SEQ ID NO 48
<211> LENGTH: 263
<212> TYPE: PRT
<213> ORGANISM: Artificial Sequence
<220> FEATURE:
<223> OTHER INFORMATION: Variant of ketoreductase from Novosphingobium aromaticivorans

<400> SEQUENCE: 48

```
Met Pro Leu Glu Met Thr Ile Ala Leu Asn Asn Val Val Ala Val Val
 1               5                  10                  15
Thr Gly Ala Ala Gly Gly Ile Gly Arg Glu Leu Val Lys Ala Met Lys
                20                  25                  30
Ala Ala Asn Ala Ile Val Ile Ala Thr Asp Met Ala Pro Ser Ala Asp
            35                  40                  45
Val Glu Gly Ala Asp His Tyr Leu Gln His Asp Val Thr Ser Glu Ala
        50                  55                  60
Gly Trp Lys Ala Val Ala Ala Leu Ala Gln Glu Lys Tyr Gly Arg Val
 65                  70                  75                  80
Asp Ala Leu Val His Asn Ala Gly Ile Ser Ile Val Thr Lys Phe Glu
                85                  90                  95
Asp Thr Pro Leu Ser Asp Phe His Arg Val Asn Thr Val Asn Val Asp
            100                 105                 110
Ser Ile Ile Ile Gly Thr Gln Val Leu Leu Pro Leu Leu Lys Glu Gly
        115                 120                 125
Gly Lys Ala Arg Ala Gly Gly Ala Ser Val Val Asn Phe Ser Ser Val
    130                 135                 140
Ala Gly Leu Arg Gly Ala Ala Phe Asn Ala Ala Tyr Cys Thr Ser Lys
145                 150                 155                 160
Ala Ala Val Lys Met Leu Ser Lys Cys Leu Gly Ala Glu Phe Ala Ala
                165                 170                 175
```

Leu Gly Tyr Asn Ile Arg Val Asn Ser Val His Pro Gly Gly Ile Asp
            180                 185                 190

Thr Pro Met Leu Gly Ser Ile Met Asp Lys Tyr Val Glu Leu Gly Ala
            195                 200                 205

Ala Pro Ser Arg Glu Val Ala Gln Ala Ala Met Glu Met Arg His Pro
        210                 215                 220

Ile Gly Arg Met Gly Arg Pro Ala Glu Met Gly Gly Val Val Tyr
225                 230                 235                 240

Leu Cys Ser Asp Ala Ala Ser Phe Val Thr Cys Thr Glu Phe Val Met
                245                 250                 255

Asp Gly Gly Phe Ser Gln Val
            260

<210> SEQ ID NO 49
<211> LENGTH: 792
<212> TYPE: DNA
<213> ORGANISM: Artificial Sequence
<220> FEATURE:
<223> OTHER INFORMATION: Variant of ketoreductase from Novosphingobium
      aromaticivorans

<400> SEQUENCE: 49
atgctgcttg aaatgacgat tgctctcaac aatgtggtcg ccgtcgtcac cggcgcggcg      60
ggaggcatcg gccgcgaact ggtcaaggcg atgaaggccg ccaacgccat cgtcatcgcc     120
accgacatgg cgccctcggc cgatgtcaaa ggcgcggacc attatctcca gcacgacgtg     180
acgagcgagg ccggctggaa ggcggtcgcg gcgctggccc aggaaaagta cgggcgcgtc     240
gatgcgctgg tacacaacgc gggcatctcg atcgtcacga agttcgaaga cactccgctg     300
tccgatttcc accgcgtgaa cacggtcaac gtcgattcca tcatcatcgg tacgcaggtc     360
ctgctgccgc tgctcaagga aggcggcaag gcgcgcgcag ggggcgcctc ggtggtcaac     420
ttctccagcg tcgcgggtct gcgcggcgcg gcgttcaatg cggcctattg caccagcaag     480
gcggcggtga agatgctctc gaagtgcctc ggcgcggaat cgcggcgct cggctacaac     540 atccgcgtca actccgtgca tccgggcggc atcgataccc cgatgctcgg ctcgatcatg     600
gacaagtacg tcgaactcgg cgctgccccc tcgcgcgagg tggcccagac cgcgatggaa     660
atgcgccacc cgatcggtcg catgggtcgc cctgccgaaa tgggcggcgg cgtggtctat     720
ctctgctccg acgcagcaag cttcgtcacc tgcacggaat cgtgatgga cggcggcttc     780 agccaggtct ga                                                        792

<210> SEQ ID NO 50
<211> LENGTH: 263
<212> TYPE: PRT
<213> ORGANISM: Artificial Sequence
<220> FEATURE:
<223> OTHER INFORMATION: Variant of ketoreductase from Novosphingobium
      aromaticivorans

<400> SEQUENCE: 50

Met Leu Leu Glu Met Thr Ile Ala Leu Asn Asn Val Val Ala Val Val
1               5                   10                  15

Thr Gly Ala Ala Gly Gly Ile Gly Arg Glu Leu Val Lys Ala Met Lys
            20                  25                  30

Ala Ala Asn Ala Ile Val Ile Ala Thr Asp Met Ala Pro Ser Ala Asp
        35                  40                  45

Val Lys Gly Ala Asp His Tyr Leu Gln His Asp Val Thr Ser Glu Ala

```
                    50                  55                  60
Gly Trp Lys Ala Val Ala Ala Leu Ala Gln Glu Lys Tyr Gly Arg Val
 65                  70                  75                  80

Asp Ala Leu Val His Asn Ala Gly Ile Ser Ile Val Thr Lys Phe Glu
                 85                  90                  95

Asp Thr Pro Leu Ser Asp Phe His Arg Val Asn Thr Val Asn Val Asp
             100                 105                 110

Ser Ile Ile Ile Gly Thr Gln Val Leu Leu Pro Leu Leu Lys Glu Gly
         115                 120                 125

Gly Lys Ala Arg Ala Gly Gly Ala Ser Val Val Asn Phe Ser Ser Val
     130                 135                 140

Ala Gly Leu Arg Gly Ala Ala Phe Asn Ala Ala Tyr Cys Thr Ser Lys
145                 150                 155                 160

Ala Ala Val Lys Met Leu Ser Lys Cys Leu Gly Ala Glu Phe Ala Ala
                165                 170                 175

Leu Gly Tyr Asn Ile Arg Val Asn Ser Val His Pro Gly Gly Ile Asp
            180                 185                 190

Thr Pro Met Leu Gly Ser Ile Met Asp Lys Tyr Val Glu Leu Gly Ala
        195                 200                 205

Ala Pro Ser Arg Glu Val Ala Gln Thr Ala Met Glu Met Arg His Pro
    210                 215                 220

Ile Gly Arg Met Gly Arg Pro Ala Glu Met Gly Gly Val Val Tyr
225                 230                 235                 240

Leu Cys Ser Asp Ala Ala Ser Phe Val Thr Cys Thr Glu Phe Val Met
                245                 250                 255

Asp Gly Gly Phe Ser Gln Val
            260
```

<210> SEQ ID NO 51
<211> LENGTH: 792
<212> TYPE: DNA
<213> ORGANISM: Artificial Sequence
<220> FEATURE:
<223> OTHER INFORMATION: Variant of ketoreductase from Novosphingobium aromaticivorans

<400> SEQUENCE: 51

```
atgccgcttg aaatgacgat tgctctcaac aatgtggtcg ccgtcgtcac cggcgcggcg      60
ggaggcatcg gccgcgaact ggtcaaggcg atgaaggccg ccaacgccat cgtcatcgcc     120
accgacatgg cgccctcggc cgatgtcgaa ggcgcggacc attatctcca gcacgacgtg     180
acgagcgagg ccggctggaa ggcggtcgcg gcgctggccc aggaaaagta cgggcgcgtc     240
gatgcgctgg tgcacaacgc gggcatctcg atcgtcacga gttcgaaga cactccgctg     300
tccgatttcc accgcgtgaa cacggtcaac gtcgattcca tcatcatcgg tacgcaggtc     360
ctgctgccgc tgctcaagga aggcggcaag gcgcgcgcag ggggcgcctc ggtggtcaac     420
ttctccagcg tcgcgggtct gcgcggcgcg gcgttcaatg cggcctattg caccagcaag     480
gcggcggtga agatgctctc gaagtgcctc ggcgcggaat cgcggcgct cggctacaac     540
atccgcgtca actccgtgca tccgggcggc atcgataccc cgatgctcgg ctcgatcatg     600
gacaagtacg tcgaactcgg cgctgccccc tcgcgcgagg tggcccaggc cgcgatggaa     660
atgcgccacc cgatcggtcg catgggtcgc cctgccgaaa tgggcggcgg cgtggtctat     720
ctctgctccg acgcagcaag cttcgtcacc tgcacggaat tcgtgatgga cggcggcttc     780
agccaggtct ga                                                         792
```

<210> SEQ ID NO 52
<211> LENGTH: 263
<212> TYPE: PRT
<213> ORGANISM: Artificial Sequence
<220> FEATURE:
<223> OTHER INFORMATION: Variant of ketoreductase from Novosphingobium aromaticivorans

<400> SEQUENCE: 52

```
Met Pro Leu Glu Met Thr Ile Ala Leu Asn Asn Val Val Ala Val Val
1               5                   10                  15

Thr Gly Ala Ala Gly Gly Ile Gly Arg Glu Leu Val Lys Ala Met Lys
            20                  25                  30

Ala Ala Asn Ala Ile Val Ile Ala Thr Asp Met Ala Pro Ser Ala Asp
        35                  40                  45

Val Glu Gly Ala Asp His Tyr Leu Gln His Asp Val Thr Ser Glu Ala
    50                  55                  60

Gly Trp Lys Ala Val Ala Ala Leu Ala Gln Glu Lys Tyr Gly Arg Val
65                  70                  75                  80

Asp Ala Leu Val His Asn Ala Gly Ile Ser Ile Val Thr Lys Phe Glu
                85                  90                  95

Asp Thr Pro Leu Ser Asp Phe His Arg Val Asn Thr Val Asn Val Asp
            100                 105                 110

Ser Ile Ile Ile Gly Thr Gln Val Leu Leu Pro Leu Leu Lys Glu Gly
        115                 120                 125

Gly Lys Ala Arg Ala Gly Gly Ala Ser Val Val Asn Phe Ser Ser Val
    130                 135                 140

Ala Gly Leu Arg Gly Ala Ala Phe Asn Ala Ala Tyr Cys Thr Ser Lys
145                 150                 155                 160

Ala Ala Val Lys Met Leu Ser Lys Cys Leu Gly Ala Glu Phe Ala Ala
                165                 170                 175

Leu Gly Tyr Asn Ile Arg Val Asn Ser Val His Pro Gly Gly Ile Asp
            180                 185                 190

Thr Pro Met Leu Gly Ser Ile Met Asp Lys Tyr Val Glu Leu Gly Ala
        195                 200                 205

Ala Pro Ser Arg Glu Val Ala Gln Ala Ala Met Glu Met Arg His Pro
    210                 215                 220

Ile Gly Arg Met Gly Arg Pro Ala Glu Met Gly Gly Val Val Tyr
225                 230                 235                 240

Leu Cys Ser Asp Ala Ala Ser Phe Val Thr Cys Thr Glu Phe Val Met
                245                 250                 255

Asp Gly Gly Phe Ser Gln Val
            260
```

<210> SEQ ID NO 53
<211> LENGTH: 792
<212> TYPE: DNA
<213> ORGANISM: Artificial Sequence
<220> FEATURE:
<223> OTHER INFORMATION: Variant of ketoreductase from Novosphingobium aromaticivorans

<400> SEQUENCE: 53

```
atgccgcttg aaatgacgat tgctctcaac aatgtggtcg ccgtcgtcac cggcgcggcg    60
ggaggcatcg gccgcgaact ggtcaaggcg atgaaggccg ccaacgccat cgtcatcgcc   120
accgacatgg cgccctcggc cgatgtcgaa ggcgcggacc attatctcca gcacgacgtg   180
```

```
acgagcgagg ccggctggaa ggcggtcgca gcgctggccc aggaaaagta cgggcgcgtc    240
gatgcgctgg tgcacaacgc gggcatctcg atcgtcacga ggttcgaaga cactccgctg    300
tccgatttcc accgcgtgaa cacggtcaac gtcgattcca tcatcatcgg tacgcaggtc    360
ctgctgccgc tgctcaagga aggcggcaag gcgcgcgcag ggggcgcctc ggtggtcaac    420
ttctccagcg tcgcgggtct gcgcggcgcg gcgttcaatg ctgcctattg caccagcaag    480
gcggcggtga agatgctctc gaagtgcctc ggcgcggaat tcgcggcgct cggctacaac    540
atccgcgtca actccgtgca tccgggcggc atcgataccc cgatgctcgg ctcgaacatg    600
gacaagtacg tcgaactcgg cgctgccccc tcgcgcgagg tggcccaggc cgcgatggaa    660
atgcgccacc cgatcggtcg catgggtcgc cctgccgaaa tgggcggcgg cgtggtctat    720
ctctgctccg acgcagcaag cttcgtcacc tgcacggaat cgtgatggga cggcggcttc    780
agccaggtct ga                                                        792
```

<210> SEQ ID NO 54
<211> LENGTH: 263
<212> TYPE: PRT
<213> ORGANISM: Artificial Sequence
<220> FEATURE:
<223> OTHER INFORMATION: Variant of ketoreductase from Novosphingobium
   aromaticivorans

<400> SEQUENCE: 54

Met Pro Leu Glu Met Thr Ile Ala Leu Asn Asn Val Val Ala Val Val
1               5                   10                  15

Thr Gly Ala Ala Gly Gly Ile Gly Arg Glu Leu Val Lys Ala Met Lys
            20                  25                  30

Ala Ala Asn Ala Ile Val Ile Ala Thr Asp Met Ala Pro Ser Ala Asp
        35                  40                  45

Val Glu Gly Ala Asp His Tyr Leu Gln His Asp Val Thr Ser Glu Ala
    50                  55                  60

Gly Trp Lys Ala Val Ala Ala Leu Ala Gln Glu Lys Tyr Gly Arg Val
65                  70                  75                  80

Asp Ala Leu Val His Asn Ala Gly Ile Ser Ile Val Thr Arg Phe Glu
                85                  90                  95

Asp Thr Pro Leu Ser Asp Phe His Arg Val Asn Thr Val Asn Val Asp
            100                 105                 110

Ser Ile Ile Ile Gly Thr Gln Val Leu Leu Pro Leu Leu Lys Glu Gly
        115                 120                 125

Gly Lys Ala Arg Ala Gly Gly Ala Ser Val Val Asn Phe Ser Ser Val
    130                 135                 140

Ala Gly Leu Arg Gly Ala Ala Phe Asn Ala Ala Tyr Cys Thr Ser Lys
145                 150                 155                 160

Ala Ala Val Lys Met Leu Ser Lys Cys Leu Gly Ala Glu Phe Ala Ala
                165                 170                 175

Leu Gly Tyr Asn Ile Arg Val Asn Ser Val His Pro Gly Gly Ile Asp
            180                 185                 190

Thr Pro Met Leu Gly Ser Asn Met Asp Lys Tyr Val Glu Leu Gly Ala
        195                 200                 205

Ala Pro Ser Arg Glu Val Ala Gln Ala Ala Met Glu Met Arg His Pro
    210                 215                 220

Ile Gly Arg Met Gly Arg Pro Ala Glu Met Gly Gly Gly Val Val Tyr
225                 230                 235                 240

```
Leu Cys Ser Asp Ala Ala Ser Phe Val Thr Cys Thr Glu Phe Val Met
                245                 250                 255

Asp Gly Gly Phe Ser Gln Val
            260
```

<210> SEQ ID NO 55
<211> LENGTH: 792
<212> TYPE: DNA
<213> ORGANISM: Artificial Sequence
<220> FEATURE:
<223> OTHER INFORMATION: Variant of ketoreductase from Novosphingobium
      aromaticivorans

<400> SEQUENCE: 55

```
atgccgcttg aaatgacgat tgctctcaac aatgtggtcg ccgtcgtcac cggcgcggcg      60
ggaggcatcg gccgcgaact ggtcaaggcg atgaaggccg ccaacgccat cgtcatcgcc     120
accgacatgg cgccctcggc cgatgtcgaa ggcgcggacc attatctcca gcacgacgtg     180
acgagcgagg ccggctggaa ggcggtcgcg gcgctggccc aggaaaagta cgggcgcgtc     240
gatgcgctgg tgcacaacgc gggcatctcg atcgtcacga gttcgaaga cactccgctg     300 tccgatttcc accgcgtgaa cacggtcaac gtcgattcca tcatcatcgg tacgcaggtc     360
ctgctgccgc tgctcaagga aggcggcaag gcgcgcgcag ggggcgcctc ggtggtcaac     420
ttctccagcg tcgcgggtct gcgcggcgcg gcgttcaatg cggcctattg caccagcaag     480
gcggcggtga agatgctctc gaagtgcctc ggcgcggaat cgcggcgct cggctacaac     540 atccgcgtca actccgtgca tccggcggc atcgataccc cgatgctcgg ctcgatcatg     600
gacaagtacg tcgaactcgg cgctgccccc tcgcgcgagg tgcccaggc cgcgatggaa     660 atgcgccacc cggtcggtcg catgggtcgc cctgccgaaa tgggcggcgg cgtggtctat     720
ctctgctccg acgcagcaag cttcgtcacc tgcacggaat tcgtgatgga cggcggcttc     780
agccaggtct ga                                                         792
```

<210> SEQ ID NO 56
<211> LENGTH: 263
<212> TYPE: PRT
<213> ORGANISM: Artificial Sequence
<220> FEATURE:
<223> OTHER INFORMATION: Variant of ketoreductase from Novosphingobium
      aromaticivorans

<400> SEQUENCE: 56

```
Met Pro Leu Glu Met Thr Ile Ala Leu Asn Asn Val Val Ala Val Val
1               5                   10                  15

Thr Gly Ala Ala Gly Gly Ile Gly Arg Glu Leu Val Lys Ala Met Lys
            20                  25                  30

Ala Ala Asn Ala Ile Val Ile Ala Thr Asp Met Ala Pro Ser Ala Asp
        35                  40                  45

Val Glu Gly Ala Asp His Tyr Leu Gln His Asp Val Thr Ser Glu Ala
    50                  55                  60

Gly Trp Lys Ala Val Ala Ala Leu Ala Gln Glu Lys Tyr Gly Arg Val
65                  70                  75                  80

Asp Ala Leu Val His Asn Ala Gly Ile Ser Ile Val Thr Lys Phe Glu
                85                  90                  95

Asp Thr Pro Leu Ser Asp Phe His Arg Val Asn Thr Val Asn Val Asp
            100                 105                 110

Ser Ile Ile Ile Gly Thr Gln Val Leu Leu Pro Leu Leu Lys Glu Gly
        115                 120                 125
```

```
Gly Lys Ala Arg Ala Gly Gly Ala Ser Val Val Asn Phe Ser Ser Val
    130                 135                 140
Ala Gly Leu Arg Gly Ala Ala Phe Asn Ala Ala Tyr Cys Thr Ser Lys
145                 150                 155                 160
Ala Ala Val Lys Met Leu Ser Lys Cys Leu Gly Ala Glu Phe Ala Ala
                165                 170                 175
Leu Gly Tyr Asn Ile Arg Val Asn Ser Val His Pro Gly Gly Ile Asp
            180                 185                 190
Thr Pro Met Leu Gly Ser Ile Met Asp Lys Tyr Val Glu Leu Gly Ala
        195                 200                 205
Ala Pro Ser Arg Glu Val Ala Gln Ala Ala Met Glu Met Arg His Pro
    210                 215                 220
Val Gly Arg Met Gly Arg Pro Ala Glu Met Gly Gly Val Val Tyr
225                 230                 235                 240
Leu Cys Ser Asp Ala Ala Ser Phe Val Thr Cys Thr Glu Phe Val Met
                245                 250                 255
Asp Gly Gly Phe Ser Gln Val
            260

<210> SEQ ID NO 57
<211> LENGTH: 792
<212> TYPE: DNA
<213> ORGANISM: Artificial Sequence
<220> FEATURE:
<223> OTHER INFORMATION: Variant of ketoreductase from Novosphingobium
      aromaticivorans

<400> SEQUENCE: 57
atgccgcttg aaatgacgat tgctctcaac aatgtggtcg ccgtcgtcac cggcgcggcg      60
ggaggcatcg gccgcgaact ggtcaaggcg atgaaggccg ccaacgccat cgtcatcgcc     120
accgacatgg cgccctcggc cgatgtcgaa ggcgcggacc attatctcca gcacgacgtg     180
acgagcgagg ccggctggaa ggcggtcgcg gcgctggccc aggaaaagta cgggcgcgtc     240
gatgcgctgg tgcacaacgc gggcatctcg atcgtcacga gttcgaaga cactccgctg     300 tccgatttcc accgcgtgaa cacggtcaac gtcgattcca tcatcatcgg tacgcaggtc     360
ctgctgccgc tgctcaagga aggcggcaag gcgcgcgcag ggggcgcctc ggtggtcaac     420
ttctccagcg tcgcgggtct gcgcggcgcg gcgttcaatg cggcctattg ctccagcaag     480
gcggcggtga agatgctctc gaagtgcctc ggcgcggaat cgcggcgct cggctacaac     540 atccgcgtca actccgtgca tccgggcggc atcgataccc cgatgctagg ctcgatcatg     600
gacaagtacg tcgaactcgg cgctgccccc tcgcgcgagg tggcccaggc cgcgatggaa     660
atgcgccacc cgatcggtcg catgggtcgc cctgccgaaa tgggcggcgg cgtggtctat     720
ctctgctccg gcgcagcaag cttcgtcacc tgcacggaat tcgtgatgga cggcggcttc     780
agccaggtct ga                                                         792

<210> SEQ ID NO 58
<211> LENGTH: 263
<212> TYPE: PRT
<213> ORGANISM: Artificial Sequence
<220> FEATURE:
<223> OTHER INFORMATION: Variant of ketoreductase from Novosphingobium
      aromaticivorans

<400> SEQUENCE: 58

Met Pro Leu Glu Met Thr Ile Ala Leu Asn Asn Val Val Ala Val Val
```

```
                1               5                   10                  15
            Thr Gly Ala Ala Gly Gly Ile Gly Arg Glu Leu Val Lys Ala Met Lys
                            20                  25                  30
            Ala Ala Asn Ala Ile Val Ile Ala Thr Asp Met Ala Pro Ser Ala Asp
                        35                  40                  45
            Val Glu Gly Ala Asp His Tyr Leu Gln His Asp Val Thr Ser Glu Ala
                50                  55                  60
            Gly Trp Lys Ala Val Ala Ala Leu Ala Gln Glu Lys Tyr Gly Arg Val
            65                  70                  75                  80
            Asp Ala Leu Val His Asn Ala Gly Ile Ser Ile Val Thr Lys Phe Glu
                            85                  90                  95
            Asp Thr Pro Leu Ser Asp Phe His Arg Val Asn Thr Val Asn Val Asp
                        100                 105                 110
            Ser Ile Ile Ile Gly Thr Gln Val Leu Leu Pro Leu Leu Lys Glu Gly
                    115                 120                 125
            Gly Lys Ala Arg Ala Gly Gly Ala Ser Val Val Asn Phe Ser Ser Val
                130                 135                 140
            Ala Gly Leu Arg Gly Ala Ala Phe Asn Ala Ala Tyr Cys Ser Ser Lys
            145                 150                 155                 160
            Ala Ala Val Lys Met Leu Ser Lys Cys Leu Gly Ala Glu Phe Ala Ala
                            165                 170                 175
            Leu Gly Tyr Asn Ile Arg Val Asn Ser Val His Pro Gly Gly Ile Asp
                        180                 185                 190
            Thr Pro Met Leu Gly Ser Ile Met Asp Lys Tyr Val Glu Leu Gly Ala
                    195                 200                 205
            Ala Pro Ser Arg Glu Val Ala Gln Ala Ala Met Glu Met Arg His Pro
                210                 215                 220
            Ile Gly Arg Met Gly Arg Pro Ala Glu Met Gly Gly Val Val Tyr
            225                 230                 235                 240
            Leu Cys Ser Gly Ala Ala Ser Phe Val Thr Cys Thr Glu Phe Val Met
                            245                 250                 255
            Asp Gly Gly Phe Ser Gln Val
                        260

<210> SEQ ID NO 59
<211> LENGTH: 792
<212> TYPE: DNA
<213> ORGANISM: Artificial Sequence
<220> FEATURE:
<223> OTHER INFORMATION: Variant of ketoreductase from Novosphingobium
      aromaticivorans

<400> SEQUENCE: 59
atgccgcttg aaatgacgat tgctctcaac aatgtggtcg ccgtcgtcac cggcgcggcg      60
ggaggcatcg gccgcgaact ggtcaaggcg atgaaggccg ccaacgccat cgtcatcgcc     120
accgacatgg cgccctcggc cgatgtcgaa ggcgcggacc attatctcca gcacgacgtg     180
acgagcgagg ccggctggaa ggcggtcgcg gcgctggccc aggaaaagta cgggcgcgtc     240
gatgcgctgg tgcacaacgc gggcatctcg atcgtcacga agttcgaaga cactccgctg     300
tccgatttcc accgcgtgaa cacggtcaac gtcgattcca tcatcatcgg tacgcaggtc     360
ctgctgccgc tgctcaagga aggcggcaag gcgcgcgcag gggcgcctc ggtggtcaac      420 ttctccagcg tcgtgggtct cgcgggcgcg gcgttcaatg cggcctattg caccagcaag     480
gcggcggtga agatgctctc gaagtgcctc ggcgcggaat cgcggcgct cggctacaac     540
```

```
atccgcgtca actccgtgca tccgggcggc atcgataccc cgatgctcgg ctcgatcatg      600
gacaagtacg tcgaactcgg cgctgccccc tcgcgcgagg tggcccaggc cgcgatggaa      660
atgcgccacc cgatcggtcg catgggtcgc cctgccgaaa tgggcggcgg cgtggtctat      720
ctctgctccg acgcagcaag cttcgtcacc tgcacggaat cgtgatggga cggcggcttc      780
agccaggtct ga                                                          792
```

<210> SEQ ID NO 60
<211> LENGTH: 263
<212> TYPE: PRT
<213> ORGANISM: Artificial Sequence
<220> FEATURE:
<223> OTHER INFORMATION: Variant of ketoreductase from Novosphingobium aromaticivorans

<400> SEQUENCE: 60

```
Met Pro Leu Glu Met Thr Ile Ala Leu Asn Asn Val Val Ala Val Val
1               5                   10                  15
Thr Gly Ala Ala Gly Gly Ile Gly Arg Glu Leu Val Lys Ala Met Lys
            20                  25                  30
Ala Ala Asn Ala Ile Val Ile Ala Thr Asp Met Ala Pro Ser Ala Asp
        35                  40                  45
Val Glu Gly Ala Asp His Tyr Leu Gln His Asp Val Thr Ser Glu Ala
    50                  55                  60
Gly Trp Lys Ala Val Ala Ala Leu Ala Gln Glu Lys Tyr Gly Arg Val
65                  70                  75                  80
Asp Ala Leu Val His Asn Ala Gly Ile Ser Ile Val Thr Lys Phe Glu
                85                  90                  95
Asp Thr Pro Leu Ser Asp Phe His Arg Val Asn Thr Val Asn Val Asp
            100                 105                 110
Ser Ile Ile Ile Gly Thr Gln Val Leu Leu Pro Leu Leu Lys Glu Gly
        115                 120                 125
Gly Lys Ala Arg Ala Gly Gly Ala Ser Val Val Asn Phe Ser Ser Val
    130                 135                 140
Val Gly Leu Arg Gly Ala Ala Phe Asn Ala Ala Tyr Cys Thr Ser Lys
145                 150                 155                 160
Ala Ala Val Lys Met Leu Ser Lys Cys Leu Gly Ala Glu Phe Ala Ala
                165                 170                 175
Leu Gly Tyr Asn Ile Arg Val Asn Ser Val His Pro Gly Gly Ile Asp
            180                 185                 190
Thr Pro Met Leu Gly Ser Ile Met Asp Lys Tyr Val Glu Leu Gly Ala
        195                 200                 205
Ala Pro Ser Arg Glu Val Ala Gln Ala Ala Met Glu Met Arg His Pro
    210                 215                 220
Ile Gly Arg Met Gly Arg Pro Ala Glu Met Gly Gly Val Val Tyr
225                 230                 235                 240
Leu Cys Ser Asp Ala Ala Ser Phe Val Thr Cys Thr Glu Phe Val Met
                245                 250                 255
Asp Gly Gly Phe Ser Gln Val
            260
```

<210> SEQ ID NO 61
<211> LENGTH: 792
<212> TYPE: DNA
<213> ORGANISM: Artificial Sequence
<220> FEATURE:
<223> OTHER INFORMATION: Variant of ketoreductase from Novosphingobium -continued aromaticivorans

<400> SEQUENCE: 61

```
atgccgcttg aaatgacgat tgctctcaac aatgtggtcg ccgtcgtcac cggcgcggcg      60
ggaggcatcg gccgcgaact ggtcaaggcg atgaaggccg ccaacgccat cgtcatcgcc     120
accgacatgg cgccctcggc cgatgtcgaa ggcgcggacc attatctcca gcacgacgtg     180
acgagcgagg ccggctggaa ggcggtcgcg cgctggccc aggaaaagta cgggcgcgtc      240
gatgcgctgg tgcacaacgc gggcatctcg atcgtcacga gttcgaaga cactccgctg      300
tccgatttcc accgcgtgaa cacggtcaac gtcgattcca tcatcatcgg tacgcaggtc     360
ctgctgccgc tgctcaagga aggcggcaag gcgcgcgcag ggggcgcctc ggtggtcaac     420
ttctccagcg tcgggggtct gcgcggcgcg gcgttcaatg cggcctattg caccagcaag     480
gcggcggtga agatgctctc gaagtgcctc ggcgcggaat cgcggcgct cggctacaac      540
atccgcgtca actccgtgca tccgggcggc atcgataccc cgatgctcgg ctcgggcatg     600
gacaagtacg tcgaactcgg cgctgccccc tcgcgcgagg tgcccaggc cgcgatggaa      660
atgcgccacc cgatcggtcg catgggtcgc cctgccgaaa tgggcggcgg cgtggtctat     720
ctctgctccg acgcagcaag cttcgtcacc tgcacggaat cgtgatggaa cggcggcttc     780
agccaggtct ga                                                         792
```

<210> SEQ ID NO 62
<211> LENGTH: 263
<212> TYPE: PRT
<213> ORGANISM: Artificial Sequence
<220> FEATURE:
<223> OTHER INFORMATION: Variant of ketoreductase from Novosphingobium aromaticivorans

<400> SEQUENCE: 62

```
Met Pro Leu Glu Met Thr Ile Ala Leu Asn Asn Val Val Ala Val Val
1               5                   10                  15

Thr Gly Ala Ala Gly Gly Ile Gly Arg Glu Leu Val Lys Ala Met Lys
            20                  25                  30

Ala Ala Asn Ala Ile Val Ile Ala Thr Asp Met Ala Pro Ser Ala Asp
        35                  40                  45

Val Glu Gly Ala Asp His Tyr Leu Gln His Asp Val Thr Ser Glu Ala
    50                  55                  60

Gly Trp Lys Ala Val Ala Ala Leu Ala Gln Glu Lys Tyr Gly Arg Val
65                  70                  75                  80

Asp Ala Leu Val His Asn Ala Gly Ile Ser Ile Val Thr Lys Phe Glu
                85                  90                  95

Asp Thr Pro Leu Ser Asp Phe His Arg Val Asn Thr Val Asn Val Asp
            100                 105                 110

Ser Ile Ile Ile Gly Thr Gln Val Leu Leu Pro Leu Leu Lys Glu Gly
        115                 120                 125

Gly Lys Ala Arg Ala Gly Gly Ala Ser Val Val Asn Phe Ser Ser Val
    130                 135                 140

Gly Gly Leu Arg Gly Ala Ala Phe Asn Ala Ala Tyr Cys Thr Ser Lys
145                 150                 155                 160

Ala Ala Val Lys Met Leu Ser Lys Cys Leu Gly Ala Glu Phe Ala Ala
                165                 170                 175

Leu Gly Tyr Asn Ile Arg Val Asn Ser Val His Pro Gly Gly Ile Asp
            180                 185                 190
```

```
Thr Pro Met Leu Gly Ser Gly Met Asp Lys Tyr Val Glu Leu Gly Ala
        195                 200                 205

Ala Pro Ser Arg Glu Val Ala Gln Ala Met Glu Met Arg His Pro
        210                 215                 220

Ile Gly Arg Met Gly Arg Pro Ala Glu Met Gly Gly Val Val Tyr
225                 230                 235                 240

Leu Cys Ser Asp Ala Ala Ser Phe Val Thr Cys Thr Glu Phe Val Met
                245                 250                 255

Asp Gly Gly Phe Ser Gln Val
            260

<210> SEQ ID NO 63
<211> LENGTH: 792
<212> TYPE: DNA
<213> ORGANISM: Artificial Sequence
<220> FEATURE:
<223> OTHER INFORMATION: Variant of ketoreductase from Novosphingobium
      aromaticivorans

<400> SEQUENCE: 63
atgccgcttg aaatgacgat tgctctcaac aatgtggtcg ccgtcgtcac cggcgcggcg      60
ggaggcatcg gccgcgaact ggtcaaggcg atgaaggccg ccaacgccat cgtcatcgcc     120
accgacatgg cgccctcggc cgatgtcgaa ggcgcggacc attatctcca gcacgacgtg     180
acgagcgagg ccggctggaa ggcggtcgcg gcgctggccc aggaaaagta cgggcgcgtc     240
gatgcgctgg tgcacaacgc gggcatctcg atcgtcacga agttcgaaga cactccgctg     300
tccgatttcc accgcgtgaa cacggtcaac gtcgattcca tcatcatcgg tacgcaggtc     360
ctgctgccgc tgctcaagga aggcggcaag gcgcgcgcag ggggcgcctc ggtggtcaac     420
ttctccagct gcgggggtct gcgcggcgcg gcgttcaatg cggcctattg caccagcaag     480
gcggcggtga agatgctctc gaagtgcctc ggcgcggaat cgcggcgct cggctacaac     540 atccgcgtca actccgtgca tccgggcggc atcgataccc cgatgctcgg ctcgatcatg     600
gacaagtacg tcgaactcgg cgctgccccc tcgcgcgagg tggcccaggc cgcgatggaa     660
atgcgccacc cgatcggtcg catgggtcgc cctgccgaaa tgggcggcgg cgtggtctat     720
ctctgctccg acgcagcaag cttcgtcacc tgcacggaat tcgtgatgga cggcggcttc     780
agccaggtct ga                                                         792

<210> SEQ ID NO 64
<211> LENGTH: 263
<212> TYPE: PRT
<213> ORGANISM: Artificial Sequence
<220> FEATURE:
<223> OTHER INFORMATION: Variant of ketoreductase from Novosphingobium
      aromaticivorans

<400> SEQUENCE: 64

Met Pro Leu Glu Met Thr Ile Ala Leu Asn Asn Val Val Ala Val Val
1               5                   10                  15

Thr Gly Ala Ala Gly Gly Ile Gly Arg Glu Leu Val Lys Ala Met Lys
            20                  25                  30

Ala Ala Asn Ala Ile Val Ile Ala Thr Asp Met Ala Pro Ser Ala Asp
        35                  40                  45

Val Glu Gly Ala Asp His Tyr Leu Gln His Asp Val Thr Ser Glu Ala
    50                  55                  60

Gly Trp Lys Ala Val Ala Ala Leu Ala Gln Glu Lys Tyr Gly Arg Val
65                  70                  75                  80
```

```
Asp Ala Leu Val His Asn Ala Gly Ile Ser Ile Val Thr Lys Phe Glu
                85                  90                  95
Asp Thr Pro Leu Ser Asp Phe His Arg Val Asn Thr Val Asn Val Asp
            100                 105                 110
Ser Ile Ile Ile Gly Thr Gln Val Leu Leu Pro Leu Leu Lys Glu Gly
        115                 120                 125
Gly Lys Ala Arg Ala Gly Gly Ala Ser Val Val Asn Phe Ser Ser Cys
130                 135                 140
Gly Gly Leu Arg Gly Ala Ala Phe Asn Ala Ala Tyr Cys Thr Ser Lys
145                 150                 155                 160
Ala Ala Val Lys Met Leu Ser Lys Cys Leu Gly Ala Glu Phe Ala Ala
                165                 170                 175
Leu Gly Tyr Asn Ile Arg Val Asn Ser Val His Pro Gly Gly Ile Asp
            180                 185                 190
Thr Pro Met Leu Gly Ser Ile Met Asp Lys Tyr Val Glu Leu Gly Ala
        195                 200                 205
Ala Pro Ser Arg Glu Val Ala Gln Ala Ala Met Glu Met Arg His Pro
210                 215                 220
Ile Gly Arg Met Gly Arg Pro Ala Glu Met Gly Gly Val Val Tyr
225                 230                 235                 240
Leu Cys Ser Asp Ala Ala Ser Phe Val Thr Cys Thr Glu Phe Val Met
                245                 250                 255
Asp Gly Gly Phe Ser Gln Val
            260

<210> SEQ ID NO 65
<211> LENGTH: 792
<212> TYPE: DNA
<213> ORGANISM: Artificial Sequence
<220> FEATURE:
<223> OTHER INFORMATION: Variant of ketoreductase from Novosphingobium
      aromaticivorans

<400> SEQUENCE: 65
atgccgcttg aaatgacgat tgctctcaac aatgtggtcg ccgtcgtcac cggcgcggcg      60
ggaggcatcg ccgcgaact ggtcaaggcg atgaaggccg ccaacgccat cgtcatcgcc     120
accgacatgg cgccctcggc cgatgtcgaa ggcgcggacc attatctcca gcacgacgtg     180
acgagcgagg ccggctggaa ggcggtcgcg cgctggccc aggaaaagta cgggcgcgtc      240
gatgcgctgg tgcacaacgc gggcatctcg atcgtcacga gttcgaaga cactccgctg      300 tccgatttcc accgcgtgaa cacggtcaac gtcgattcca tcatcatcgg tacgcaggtc     360
ctgctgccgc tgctcaagga aggcggcaag gcgcgcgcag ggggcgcctc ggtggtcaac     420
ttctccagcg tcggggtct gcgcggctcg gcgttcaatg cggcctattg caccagcaag     480
gcggcggtga agatgctctc gaagtgcctc ggcgcggaat cgcggcgct cggctacaac     540 atccgcgtca actccgtgca tccgggcggc atcgataccc cgatgctcgg ctcgatcatg     600
gacaagtacg tcgaactcgg cgctgccccc tcgcgcgagg tggcccaggc cgcgatggaa     660
atgcgccacc cgatcggtcg catgggtcgc cctgccgaaa tgggcggcgg cgtggtctat     720
ctctgctccg acgcagcaag cttcgtcacc tgcacggaat tcgtgatgga cggcggcttc     780
agccaggtct ga                                                        792

<210> SEQ ID NO 66
<211> LENGTH: 263
```

<212> TYPE: PRT
<213> ORGANISM: Artificial Sequence
<220> FEATURE:
<223> OTHER INFORMATION: Variant of ketoreductase from Novosphingobium
      aromaticivorans

<400> SEQUENCE: 66

Met Pro Leu Glu Met Thr Ile Ala Leu Asn Asn Val Val Ala Val Val
1               5                   10                  15

Thr Gly Ala Ala Gly Gly Ile Gly Arg Glu Leu Val Lys Ala Met Lys
            20                  25                  30

Ala Ala Asn Ala Ile Val Ile Ala Thr Asp Met Ala Pro Ser Ala Asp
        35                  40                  45

Val Glu Gly Ala Asp His Tyr Leu Gln His Asp Val Thr Ser Glu Ala
    50                  55                  60

Gly Trp Lys Ala Val Ala Ala Leu Ala Gln Glu Lys Tyr Gly Arg Val
65                  70                  75                  80

Asp Ala Leu Val His Asn Ala Gly Ile Ser Ile Val Thr Lys Phe Glu
                85                  90                  95

Asp Thr Pro Leu Ser Asp Phe His Arg Val Asn Thr Val Asn Val Asp
            100                 105                 110

Ser Ile Ile Ile Gly Thr Gln Val Leu Leu Pro Leu Leu Lys Glu Gly
        115                 120                 125

Gly Lys Ala Arg Ala Gly Gly Ala Ser Val Val Asn Phe Ser Ser Val
130                 135                 140

Gly Gly Leu Arg Gly Ser Ala Phe Asn Ala Ala Tyr Cys Thr Ser Lys
145                 150                 155                 160

Ala Ala Val Lys Met Leu Ser Lys Cys Leu Gly Ala Glu Phe Ala Ala
                165                 170                 175

Leu Gly Tyr Asn Ile Arg Val Asn Ser Val His Pro Gly Gly Ile Asp
            180                 185                 190

Thr Pro Met Leu Gly Ser Ile Met Asp Lys Tyr Val Glu Leu Gly Ala
        195                 200                 205

Ala Pro Ser Arg Glu Val Ala Gln Ala Ala Met Glu Met Arg His Pro
    210                 215                 220

Ile Gly Arg Met Gly Arg Pro Ala Glu Met Gly Gly Val Val Tyr
225                 230                 235                 240

Leu Cys Ser Asp Ala Ala Ser Phe Val Thr Cys Thr Glu Phe Val Met
                245                 250                 255

Asp Gly Gly Phe Ser Gln Val
            260

<210> SEQ ID NO 67
<211> LENGTH: 792
<212> TYPE: DNA
<213> ORGANISM: Artificial Sequence
<220> FEATURE:
<223> OTHER INFORMATION: Variant of ketoreductase from Novosphingobium
      aromaticivorans

<400> SEQUENCE: 67
atgccgcttg aaatgacgat tgctctcaac aatgtggtcg ccgtcgtcac cggcgcggcg      60
ggaggcatcg gccgcgaact ggtcaaggcg atgaaggccg ccaacgccat cgtcatcgcc     120
accgacatgg cgccctcggc cgatgtcgaa ggcgcggacc attatctcca gcacgacgtg     180
acgagcgagg ccggctggaa ggcggtcgcg gcgctggccc aggaaaagta cgggcgcgtc     240
gatgcgctgg tgcacaacgc gggcatctcg atcgtcacga agttcgaaga cactccgctg     300

```
tccgatttcc accgcgtgaa cacggtcaac gtcgattcca tcatcatcgg tacgcaggtc    360
ctgctgccgc tgctcaagga aggcggcaag gcgcgcgcag ggggcgcctc ggtggtcaac    420
ttctccagcg tcgggggtct gcgcggcatc gcgttcaatg cggcctattg caccagcaag    480
gcggcggtga agatgctctc gaagtgcctc ggcgcggaat cgcggcgct cggctacaac     540 atccgcgtca actccgtgca tccgggcggc atcgataccc cgatgctcgg ctcgatcatg    600
gacaagtacg tcgaactcgg cgctgccccc tcgcgcgagg tggcccaggc cgcgatggaa    660
atgcgccacc cgatcggtcg catgggtcgc cctgccgaaa tgggcggcgg cgtggtctat    720
ctctgctccg acgcagcaag cttcgtcacc tgcacggaat cgtgatgga cggcggcttc     780 agccaggtct ga                                                        792
```

<210> SEQ ID NO 68
<211> LENGTH: 263
<212> TYPE: PRT
<213> ORGANISM: Artificial Sequence
<220> FEATURE:
<223> OTHER INFORMATION: Variant of ketoreductase from Novosphingobium
    aromaticivorans

<400> SEQUENCE: 68

```
Met Pro Leu Glu Met Thr Ile Ala Leu Asn Asn Val Ala Val Val
1               5                   10                  15

Thr Gly Ala Ala Gly Gly Ile Gly Arg Glu Leu Val Lys Ala Met Lys
            20                  25                  30

Ala Ala Asn Ala Ile Val Ile Ala Thr Asp Met Ala Pro Ser Ala Asp
        35                  40                  45

Val Glu Gly Ala Asp His Tyr Leu Gln His Asp Val Thr Ser Glu Ala
    50                  55                  60

Gly Trp Lys Ala Val Ala Ala Leu Ala Gln Glu Lys Tyr Gly Arg Val
65                  70                  75                  80

Asp Ala Leu Val His Asn Ala Gly Ile Ser Ile Val Thr Lys Phe Glu
                85                  90                  95

Asp Thr Pro Leu Ser Asp Phe His Arg Val Asn Thr Val Asn Val Asp
            100                 105                 110

Ser Ile Ile Ile Gly Thr Gln Val Leu Leu Pro Leu Leu Lys Glu Gly
        115                 120                 125

Gly Lys Ala Arg Ala Gly Gly Ala Ser Val Val Asn Phe Ser Ser Val
    130                 135                 140

Gly Gly Leu Arg Gly Ile Ala Phe Asn Ala Ala Tyr Cys Thr Ser Lys
145                 150                 155                 160

Ala Ala Val Lys Met Leu Ser Lys Cys Leu Gly Ala Glu Phe Ala Ala
                165                 170                 175

Leu Gly Tyr Asn Ile Arg Val Asn Ser Val His Pro Gly Gly Ile Asp
            180                 185                 190

Thr Pro Met Leu Gly Ser Ile Met Asp Lys Tyr Val Glu Leu Gly Ala
        195                 200                 205

Ala Pro Ser Arg Glu Val Ala Gln Ala Ala Met Glu Met Arg His Pro
    210                 215                 220

Ile Gly Arg Met Gly Arg Pro Ala Glu Met Gly Gly Gly Val Val Tyr
225                 230                 235                 240

Leu Cys Ser Asp Ala Ala Ser Phe Val Thr Cys Thr Glu Phe Val Met
                245                 250                 255

Asp Gly Gly Phe Ser Gln Val
```

<210> SEQ ID NO 69
<211> LENGTH: 792
<212> TYPE: DNA
<213> ORGANISM: Artificial Sequence
<220> FEATURE:
<223> OTHER INFORMATION: Variant of ketoreductase from Novosphingobium aromaticivorans

<400> SEQUENCE: 69

```
atgccgcttg aaatgacgat tgctctcaac aatgtggtcg ccgtcgtcac cggcgcggcg      60
ggaggcatcg gccgcgaact ggtcaaggcg atgaaggccg ccaacgccat cgtcatcgcc     120
accgacatgg cgccctcggc cgatgtcgaa ggcgcggacc attatctcca gcacgacgtg     180
acgagcgagg ccggctggaa ggcggtcgcg gcgctggccc aggaaaagta cgggcgcgtc     240
gatgcgctgg tgcacaacgc gggcatctcg atcgtcacga agttcgaaga cactccgctg     300
tccgatttcc accgcgtgaa cacggtcaac gtcgattcca tcatcatcgg tacgcaggtc     360
ctgctgccgc tgctcaagga aggcggcaag gcgcgcgcag ggggcgcctc ggtggtcaac     420
ttctccagcg tcgggggtct gcgcggctgg gcgttcaatg cggcctattg caccagcaag     480
gcggcggtga agatgctctc gaagtgcctc ggcgcggaat cgcggcgct cggctacaac      540
atccgcgtca actccgtgca tccgggcggc atcgataccc cgatgctcgg ctcgatcatg     600
gacaagtacg tcgaactcgg cgctgccccc tcgcgcgagg tggcccaggc cgcgatggaa     660
atgcgccacc cgatcggtcg catgggtcgc cctgccgaaa tgggcggcgg cgtggtctat     720
ctctgctccg acgcagcaag cttcgtcacc tgcacggaat tcgtgatgga cggcggcttc     780
agccaggtct ga                                                         792
```

<210> SEQ ID NO 70
<211> LENGTH: 263
<212> TYPE: PRT
<213> ORGANISM: Artificial Sequence
<220> FEATURE:
<223> OTHER INFORMATION: Variant of ketoreductase from Novosphingobium aromaticivorans

<400> SEQUENCE: 70

```
Met Pro Leu Glu Met Thr Ile Ala Leu Asn Asn Val Val Ala Val Val
1               5                   10                  15

Thr Gly Ala Ala Gly Gly Ile Gly Arg Glu Leu Val Lys Ala Met Lys
            20                  25                  30

Ala Ala Asn Ala Ile Val Ile Ala Thr Asp Met Ala Pro Ser Ala Asp
        35                  40                  45

Val Glu Gly Ala Asp His Tyr Leu Gln His Asp Val Thr Ser Glu Ala
    50                  55                  60

Gly Trp Lys Ala Val Ala Ala Leu Ala Gln Glu Lys Tyr Gly Arg Val
65                  70                  75                  80

Asp Ala Leu Val His Asn Ala Gly Ile Ser Ile Val Thr Lys Phe Glu
                85                  90                  95

Asp Thr Pro Leu Ser Asp Phe His Arg Val Asn Thr Val Asn Val Asp
            100                 105                 110

Ser Ile Ile Ile Gly Thr Gln Val Leu Leu Pro Leu Leu Lys Glu Gly
        115                 120                 125

Gly Lys Ala Arg Ala Gly Gly Ala Ser Val Val Asn Phe Ser Ser Val
    130                 135                 140
```

Gly Gly Leu Arg Gly Trp Ala Phe Asn Ala Ala Tyr Cys Thr Ser Lys
145                 150                 155                 160

Ala Ala Val Lys Met Leu Ser Lys Cys Leu Gly Ala Glu Phe Ala Ala
            165                 170                 175

Leu Gly Tyr Asn Ile Arg Val Asn Ser Val His Pro Gly Gly Ile Asp
            180                 185                 190

Thr Pro Met Leu Gly Ser Ile Met Asp Lys Tyr Val Glu Leu Gly Ala
            195                 200                 205

Ala Pro Ser Arg Glu Val Ala Gln Ala Ala Met Glu Met Arg His Pro
        210                 215                 220

Ile Gly Arg Met Gly Arg Pro Ala Glu Met Gly Gly Val Val Tyr
225                 230                 235                 240

Leu Cys Ser Asp Ala Ala Ser Phe Val Thr Cys Thr Glu Phe Val Met
                245                 250                 255

Asp Gly Gly Phe Ser Gln Val
            260

<210> SEQ ID NO 71
<211> LENGTH: 792
<212> TYPE: DNA
<213> ORGANISM: Artificial Sequence
<220> FEATURE:
<223> OTHER INFORMATION: Variant of ketoreductase from Novosphingobium
      aromaticivorans

<400> SEQUENCE: 71
atgccgcttg aaatgacgat tgctctcaac aatgtggtcg ccgtcgtcac cggcgcggcg      60
ggaggcatcg gccgcgaact ggtcaaggcg atgaaggccg ccaacgccat cgtcatcgcc     120
accgacatgg cgccctcggc cgatgtcgaa ggcgcggacc attatctcca gcacgacgtg     180
acgagcgagg ccggctggaa ggcggtcgcg gcgctggccc aggaaaagta cgggcgcgtc     240
gatgcgctgg tgcacaacgc gggcatctcg atcgtcacga agttcgaaga cactccgctg     300
tccgatttcc accgcgtgaa cacggtcaac gtcgattcca tcatcatcgg tacgcaggtc     360
ctgctgccgc tgctcaagga aggcggcaag gcgcgcgcag ggggcgcctc ggtggtcaac     420
ttctccagcg tcgggggtct cgcgcggcgcg gcgttcaatg cggcctattg caccagcaag     480
gcggcggtga agatgctctc gaagtgcctc ggcgcggaat cgcggcgct cggctacaac     540 atccgcgtca actccgtgca tccgggcccc atcgataccc cgatgctcgg ctcgatcatg     600
gacaagtacg tcgaactcgg cgctgccccc tcgcgcgagg tggcccaggc cgcgatggaa     660
atgcgccacc cgatcggtcg catgggtcgc cctgccgaaa tgggcggcgg cgtggtctat     720
ctctgctccg acgcagcaag cttcgtcacc tgcacggaat tcgtgatgga cggcggcttc     780
agccaggtct ga                                                         792

<210> SEQ ID NO 72
<211> LENGTH: 263
<212> TYPE: PRT
<213> ORGANISM: Artificial Sequence
<220> FEATURE:
<223> OTHER INFORMATION: Variant of ketoreductase from Novosphingobium
      aromaticivorans

<400> SEQUENCE: 72

Met Pro Leu Glu Met Thr Ile Ala Leu Asn Asn Val Val Ala Val Val
1               5                   10                  15

Thr Gly Ala Ala Gly Gly Ile Gly Arg Glu Leu Val Lys Ala Met Lys
            20                  25                  30

-continued

```
Ala Ala Asn Ala Ile Val Ile Ala Thr Asp Met Ala Pro Ser Ala Asp
         35                  40                  45

Val Glu Gly Ala Asp His Tyr Leu Gln His Asp Val Thr Ser Glu Ala
 50                  55                  60

Gly Trp Lys Ala Val Ala Ala Leu Ala Gln Glu Lys Tyr Gly Arg Val
 65                  70                  75                  80

Asp Ala Leu Val His Asn Ala Gly Ile Ser Ile Val Thr Lys Phe Glu
                 85                  90                  95

Asp Thr Pro Leu Ser Asp Phe His Arg Val Asn Thr Val Asn Val Asp
            100                 105                 110

Ser Ile Ile Ile Gly Thr Gln Val Leu Leu Pro Leu Leu Lys Glu Gly
        115                 120                 125

Gly Lys Ala Arg Ala Gly Gly Ala Ser Val Val Asn Phe Ser Ser Val
130                 135                 140

Gly Gly Leu Arg Gly Ala Ala Phe Asn Ala Ala Tyr Cys Thr Ser Lys
145                 150                 155                 160

Ala Ala Val Lys Met Leu Ser Lys Cys Leu Gly Ala Glu Phe Ala Ala
                165                 170                 175

Leu Gly Tyr Asn Ile Arg Val Asn Ser Val His Pro Gly Pro Ile Asp
            180                 185                 190

Thr Pro Met Leu Gly Ser Ile Met Asp Lys Tyr Val Glu Leu Gly Ala
        195                 200                 205

Ala Pro Ser Arg Glu Val Ala Gln Ala Ala Met Glu Met Arg His Pro
    210                 215                 220

Ile Gly Arg Met Gly Arg Pro Ala Glu Met Gly Gly Val Val Tyr
225                 230                 235                 240

Leu Cys Ser Asp Ala Ala Ser Phe Val Thr Cys Thr Glu Phe Val Met
                245                 250                 255

Asp Gly Gly Phe Ser Gln Val
            260
```

<210> SEQ ID NO 73
<211> LENGTH: 792
<212> TYPE: DNA
<213> ORGANISM: Artificial Sequence
<220> FEATURE:
<223> OTHER INFORMATION: Variant of ketoreductase from Novosphingobium aromaticivorans

<400> SEQUENCE: 73

```
atgccgcttg aaatgacgat tgctctcaac aatgtggtcg ccgtcgtcac cggcgcggcg      60
ggaggcatcg ccgcgaact ggtcaaggcg atgaaggccg ccaacgccat cgtcatcgcc     120
accgacatgg cgccctcggc cgatgtcgaa ggcgcggacc attatctcca gcacgacgtg     180
acgagcgagg ccggctggaa ggcggtcgcg gcgctggccc aggaaaagta cgggcgcgtc     240
gatgcgctgt tgcacaacgc gggcatctcg atcgtcacga agttcgaaga cactccgctg     300
tccgatttcc accgcgtgaa cacggtcaac gtcgattcca tcatcatcgg tacgcaggtc     360
ctgctgccgc tgctcaagga aggcggcaag gcgcgcgcag ggggcgcctc ggtggtcaac     420
ttctccagcg tcgggggtct tgcgcggcgcg gcgttcaatg cggcctattg caccagcaag     480
gcggcggtga agatgctctc gaagtgcctc ggcgcggaat cgcggcgct cggctacaac     540 atccgcgtca actccgtgca tccgggccag atcgataccc cgatgctcgg ctcgatcatg     600
gacaagtacg tcgaactcgg cgctgccccc tcgcgcgagg tggcccaggc cgcgatggaa     660
```

```
atgcgccacc cgatcggtcg catgggtcgc cctgccgaaa tgggcggcgg cgtggtctat    720
ctctgctccg acgcagcaag cttcgtcacc tgcacggaat tcgtgatgga cggcggcttc    780
agccaggtct ga                                                        792
```

<210> SEQ ID NO 74
<211> LENGTH: 263
<212> TYPE: PRT
<213> ORGANISM: Artificial Sequence
<220> FEATURE:
<223> OTHER INFORMATION: Variant of ketoreductase from Novosphingobium aromaticivorans

<400> SEQUENCE: 74

```
Met Pro Leu Glu Met Thr Ile Ala Leu Asn Asn Val Ala Val Val
1               5                   10                  15

Thr Gly Ala Ala Gly Gly Ile Gly Arg Glu Leu Val Lys Ala Met Lys
                20                  25                  30

Ala Ala Asn Ala Ile Val Ile Ala Thr Asp Met Ala Pro Ser Ala Asp
            35                  40                  45

Val Glu Gly Ala Asp His Tyr Leu Gln His Asp Val Thr Ser Glu Ala
        50                  55                  60

Gly Trp Lys Ala Val Ala Ala Leu Ala Gln Glu Lys Tyr Gly Arg Val
65                  70                  75                  80

Asp Ala Leu Val His Asn Ala Gly Ile Ser Ile Val Thr Lys Phe Glu
                85                  90                  95

Asp Thr Pro Leu Ser Asp Phe His Arg Val Asn Thr Val Asn Val Asp
            100                 105                 110

Ser Ile Ile Ile Gly Thr Gln Val Leu Leu Pro Leu Leu Lys Glu Gly
        115                 120                 125

Gly Lys Ala Arg Ala Gly Gly Ala Ser Val Val Asn Phe Ser Ser Val
    130                 135                 140

Gly Gly Leu Arg Gly Ala Ala Phe Asn Ala Ala Tyr Cys Thr Ser Lys
145                 150                 155                 160

Ala Ala Val Lys Met Leu Ser Lys Cys Leu Gly Ala Glu Phe Ala Ala
                165                 170                 175

Leu Gly Tyr Asn Ile Arg Val Asn Ser Val His Pro Gly Gln Ile Asp
            180                 185                 190

Thr Pro Met Leu Gly Ser Ile Met Asp Lys Tyr Val Glu Leu Gly Ala
        195                 200                 205

Ala Pro Ser Arg Glu Val Ala Gln Ala Ala Met Glu Met Arg His Pro
    210                 215                 220

Ile Gly Arg Met Gly Arg Pro Ala Glu Met Gly Gly Val Val Tyr
225                 230                 235                 240

Leu Cys Ser Asp Ala Ala Ser Phe Val Thr Cys Thr Glu Phe Val Met
                245                 250                 255

Asp Gly Gly Phe Ser Gln Val
            260
```

<210> SEQ ID NO 75
<211> LENGTH: 792
<212> TYPE: DNA
<213> ORGANISM: Artificial Sequence
<220> FEATURE:
<223> OTHER INFORMATION: Variant of ketoreductase from Novosphingobium aromaticivorans

<400> SEQUENCE: 75

```
atgccgcttg aaatgacgat tgctctcaac aatgtggtcg ccgtcgtcac cggcgcggcg      60
ggaggcatcg gccgcgaact ggtcaaggcg atgaaggccg ccaacgccat cgtcatcgcc     120
accgacatgg cgccctcggc cgatgtcgaa ggcgcggacc attatctcca gcacgacgtg     180
acgagcgagg ccggctggaa ggcggtcgcg gcgctggccc aggaaaagta cgggcgcgtc     240
gatgcgctgg tgcacaacgc gggcatctcg atcgtcacga agttcgaaga cactccgctg     300
tccgatttcc accgcgtgaa cacggtcaac gtcgattcca tcatcatcgg tacgcaggtc     360
ctgctgccgc tgctcaagga aggcggcaag gcgcgcgcag ggggcgcctc ggtggtcaac     420
ttctccagcg tcgggggtct gcgcggcgcg gcgttcaatg cggcctattg caccagcaag     480
gcggcggtga agatgctctc gaagtgcctc ggcgcggaat cgcggcgct cggctacaac      540
atccgcgtca actccgtgca tccgggcgtc atcgataccc cgatgctcgg ctcgatcatg     600
gacaagtacg tcgaactcgg cgctgccccc tcgcgcgagg tggcccaggc cgcgatggaa     660
atgcgccacc cgatcggtcg catgggtcgc cctgccgaaa tgggcggcgg cgtggtctat     720
ctctgctccg acgcagcaag cttcgtcacc tgcacggaat tcgtgatgga cggcggcttc     780
agccaggtct ga                                                         792
```

<210> SEQ ID NO 76
<211> LENGTH: 263
<212> TYPE: PRT
<213> ORGANISM: Artificial Sequence
<220> FEATURE:
<223> OTHER INFORMATION: Variant of ketoreductase from Novosphingobium aromaticivorans

<400> SEQUENCE: 76

```
Met Pro Leu Glu Met Thr Ile Ala Leu Asn Asn Val Val Ala Val
1               5                   10                  15

Thr Gly Ala Ala Gly Gly Ile Gly Arg Glu Leu Val Lys Ala Met Lys
            20                  25                  30

Ala Ala Asn Ala Ile Val Ile Ala Thr Asp Met Ala Pro Ser Ala Asp
        35                  40                  45

Val Glu Gly Ala Asp His Tyr Leu Gln His Asp Val Thr Ser Glu Ala
    50                  55                  60

Gly Trp Lys Ala Val Ala Ala Leu Ala Gln Glu Lys Tyr Gly Arg Val
65                  70                  75                  80

Asp Ala Leu Val His Asn Ala Gly Ile Ser Ile Val Thr Lys Phe Glu
                85                  90                  95

Asp Thr Pro Leu Ser Asp Phe His Arg Val Asn Thr Val Asn Val Asp
            100                 105                 110

Ser Ile Ile Ile Gly Thr Gln Val Leu Leu Pro Leu Leu Lys Glu Gly
        115                 120                 125

Gly Lys Ala Arg Ala Gly Gly Ala Ser Val Val Asn Phe Ser Ser Val
    130                 135                 140

Gly Gly Leu Arg Gly Ala Ala Phe Asn Ala Ala Tyr Cys Thr Ser Lys
145                 150                 155                 160

Ala Ala Val Lys Met Leu Ser Lys Cys Leu Gly Ala Glu Phe Ala Ala
                165                 170                 175

Leu Gly Tyr Asn Ile Arg Val Asn Ser Val His Pro Gly Val Ile Asp
            180                 185                 190

Thr Pro Met Leu Gly Ser Ile Met Asp Lys Tyr Val Glu Leu Gly Ala
        195                 200                 205

Ala Pro Ser Arg Glu Val Ala Gln Ala Ala Met Glu Met Arg His Pro
```

```
                210               215                 220
Ile Gly Arg Met Gly Arg Pro Ala Glu Met Gly Gly Val Val Tyr
225                 230                 235                 240

Leu Cys Ser Asp Ala Ala Ser Phe Val Thr Cys Thr Glu Phe Val Met
                245                 250                 255

Asp Gly Gly Phe Ser Gln Val
            260

<210> SEQ ID NO 77
<211> LENGTH: 792
<212> TYPE: DNA
<213> ORGANISM: Artificial Sequence
<220> FEATURE:
<223> OTHER INFORMATION: Variant of ketoreductase from Novosphingobium
      aromaticivorans

<400> SEQUENCE: 77
atgccgcttg aaatgacgat tgctctcaac aatgtggtcg ccgtcgtcac cggcgcggcg      60
ggaggcatcg gccgcgaact ggtcaaggcg atgaaggccg ccaacgccat cgtcatcgcc     120
accgacatgg cgccctcggc cgatgtcgaa ggcgcggacc attatctcca gcacgacgtg     180
acgagcgagg ccggctggaa ggcggtcgcg gcgctggccc aggaaaagta cgggcgcgtc     240
gatgcgctgg tgcacaacgc gggcatctcg atcgtcacga agttcgaaga cactccgctg     300
tccgatttcc accgcgtgaa cacggtcaac gtcgattcca tcatcatcgg tacgcaggtc     360
ctgctgccgc tgctcaagga aggcggcaag gcgcgcgcag ggggcgcctc ggtggtcaac     420
ttctccagcg tcgggggtct gcgcggcgcg gcgttcaatg cggcctattg caccagcaag     480
gcggcggtga agatgctctc gaagtgcctc ggcgcggaat cgcggcgct cggctacaac     540 atccgcgtca actccgtgca tccgggcggc atcgataccc cgatgctcgg ctcgatcatg     600
gacaagtact cgaactcgg cgctgccccc tcgcgcgagg tgcccaggc cgcgatggaa      660 atgccgccacc cgatcggtcg catgggtcgc cctgccgaaa tgggcggcgg cgtggtctat     720
ctctgctccg acgcagcaag cttcgtcacc tgcacggaat tcgtgatgga cggcggcttc     780
agccaggtct ga                                                          792

<210> SEQ ID NO 78
<211> LENGTH: 263
<212> TYPE: PRT
<213> ORGANISM: Artificial Sequence
<220> FEATURE:
<223> OTHER INFORMATION: Variant of ketoreductase from Novosphingobium
      aromaticivorans

<400> SEQUENCE: 78

Met Pro Leu Glu Met Thr Ile Ala Leu Asn Asn Val Val Ala Val Val
1               5                   10                  15

Thr Gly Ala Ala Gly Gly Ile Gly Arg Glu Leu Val Lys Ala Met Lys
            20                  25                  30

Ala Ala Asn Ala Ile Val Ile Ala Thr Asp Met Ala Pro Ser Ala Asp
        35                  40                  45

Val Glu Gly Ala Asp His Tyr Leu Gln His Asp Val Thr Ser Glu Ala
    50                  55                  60

Gly Trp Lys Ala Val Ala Ala Leu Ala Gln Glu Lys Tyr Gly Arg Val
65                  70                  75                  80

Asp Ala Leu Val His Asn Ala Gly Ile Ser Ile Val Thr Lys Phe Glu
                85                  90                  95
```

Asp Thr Pro Leu Ser Asp Phe His Arg Val Asn Thr Val Asn Val Asp
        100                 105                 110

Ser Ile Ile Ile Gly Thr Gln Val Leu Leu Pro Leu Leu Lys Glu Gly
        115                 120                 125

Gly Lys Ala Arg Ala Gly Gly Ala Ser Val Val Asn Phe Ser Ser Val
        130                 135                 140

Gly Gly Leu Arg Gly Ala Ala Phe Asn Ala Ala Tyr Cys Thr Ser Lys
145                 150                 155                 160

Ala Ala Val Lys Met Leu Ser Lys Cys Leu Gly Ala Glu Phe Ala Ala
                165                 170                 175

Leu Gly Tyr Asn Ile Arg Val Asn Ser Val His Pro Gly Gly Ile Asp
                180                 185                 190

Thr Pro Met Leu Gly Ser Ile Met Asp Lys Tyr Phe Glu Leu Gly Ala
        195                 200                 205

Ala Pro Ser Arg Glu Val Ala Gln Ala Ala Met Glu Met Arg His Pro
        210                 215                 220

Ile Gly Arg Met Gly Arg Pro Ala Glu Met Gly Gly Val Val Tyr
225                 230                 235                 240

Leu Cys Ser Asp Ala Ala Ser Phe Val Thr Cys Thr Glu Phe Val Met
                245                 250                 255

Asp Gly Gly Phe Ser Gln Val
        260

<210> SEQ ID NO 79
<211> LENGTH: 792
<212> TYPE: DNA
<213> ORGANISM: Artificial Sequence
<220> FEATURE:
<223> OTHER INFORMATION: Variant of ketoreductase from Novosphingobium
      aromaticivorans

<400> SEQUENCE: 79
atgccgcttg aaatgacgat tgctctcaac aatgtggtcg ccgtcgtcac cggcgcggcg      60
ggaggcatcg gccgcgaact ggtcaaggcg atgaaggccg ccaacgccat cgtcatcgcc     120
accgacatgg cgccctcggc cgatgtcgaa ggcgcggacc attatctcca gcacgacgtg     180
acgagcgagg ccggctggaa ggcggtcgcg cgctggccc aggaaaagta cgggcgcgtc     240
gatgcgctgt gcacaacgc gggcatctcg atcgtcacga gttcgaaga cactccgctg     300 tccgatttcc accgcgtgaa cacggtcaac gtcgattcca tcatcatcgg tacgcaggtc     360
ctgctgccgc tgctcaagga aggcggcaag gcgcgcgcag ggggcgcctc ggtggtcaac     420
ttctccagcg tcgggggtct cgcgcggcgcg gcgttcaatg cggcctattg caccagcaag     480
gcggcggtga agatgctctc gaagtgcctc ggcgcggaat cgcggcgct cggctacaac     540 atccgcgtca actccgtgca tccgggcggc atcgataccc cgatgctcgg ctcgatcatt     600
gacaagtacg tcgaactcgg cgctgccccc tcgcgcgagg tggcccaggc cgcgatggaa     660
atgcgccacc cgatcggtcg catgggtcgc cctgccgaaa tgggcggcgg cgtggtctat     720
ctctgctccg acgcagcaag cttcgtcacc tgcacggaat cgtgatgga cggcggcttc     780 agccaggtct ga                                                         792

<210> SEQ ID NO 80
<211> LENGTH: 263
<212> TYPE: PRT
<213> ORGANISM: Artificial Sequence
<220> FEATURE:
<223> OTHER INFORMATION: Variant of ketoreductase from Novosphingobium aromaticivorans

<400> SEQUENCE: 80

```
Met Pro Leu Glu Met Thr Ile Ala Leu Asn Asn Val Val Ala Val Val
1               5                   10                  15
Thr Gly Ala Ala Gly Gly Ile Gly Arg Glu Leu Val Lys Ala Met Lys
                20                  25                  30
Ala Ala Asn Ala Ile Val Ile Ala Thr Asp Met Ala Pro Ser Ala Asp
            35                  40                  45
Val Glu Gly Ala Asp His Tyr Leu Gln His Asp Val Thr Ser Glu Ala
        50                  55                  60
Gly Trp Lys Ala Val Ala Ala Leu Ala Gln Glu Lys Tyr Gly Arg Val
65                  70                  75                  80
Asp Ala Leu Val His Asn Ala Gly Ile Ser Ile Val Thr Lys Phe Glu
                85                  90                  95
Asp Thr Pro Leu Ser Asp Phe His Arg Val Asn Thr Val Asn Val Asp
                100                 105                 110
Ser Ile Ile Ile Gly Thr Gln Val Leu Leu Pro Leu Leu Lys Glu Gly
            115                 120                 125
Gly Lys Ala Arg Ala Gly Gly Ala Ser Val Val Asn Phe Ser Ser Val
130                 135                 140
Gly Gly Leu Arg Gly Ala Ala Phe Asn Ala Ala Tyr Cys Thr Ser Lys
145                 150                 155                 160
Ala Ala Val Lys Met Leu Ser Lys Cys Leu Gly Ala Glu Phe Ala Ala
                165                 170                 175
Leu Gly Tyr Asn Ile Arg Val Asn Ser Val His Pro Gly Gly Ile Asp
            180                 185                 190
Thr Pro Met Leu Gly Ser Ile Ile Asp Lys Tyr Val Glu Leu Gly Ala
            195                 200                 205
Ala Pro Ser Arg Glu Val Ala Gln Ala Ala Met Glu Met Arg His Pro
210                 215                 220
Ile Gly Arg Met Gly Arg Pro Ala Glu Met Gly Gly Val Val Tyr
225                 230                 235                 240
Leu Cys Ser Asp Ala Ala Ser Phe Val Thr Cys Thr Glu Phe Val Met
            245                 250                 255
Asp Gly Gly Phe Ser Gln Val
            260
```

KETOREDUCTASE-MEDIATED STEREOSELECTIVE ROUTE TO ALPHA CHLOROALCOHOLS

The present application is a Divisional of U.S. patent application Ser. No. 13/378,618, filed Apr. 10, 2012, now U.S. Pat. No. 8,796,002, which claims priority to PCT/US2010/039511, filed Jun. 22, 2010, which claims priority to U.S. Prov. Appln. Ser No. 61/219,162, filed Jun. 22, 2009, and U.S. Prov. Appln. Ser. No. 61/303,057, filed Feb. 10, 2010, all of which are incorporated by reference in their entireties, for all purposes.

1. TECHNICAL FIELD

The present disclosure relates to engineered polypeptides and uses thereof for the preparation of α-chloroalcohols from α-chloroketones.

2. REFERENCE TO SEQUENCE LISTING, TABLE OR COMPUTER PROGRAM

The Sequence Listing concurrently submitted electronically under 37 C.F.R. §1.821 via EFS-Web in a computer readable form (CRF) as file name CX2-012WO1_ST25.txt is herein incorporated by reference. The electronic copy of the Sequence Listing was created on Jun. 22, 2010, with a file size of 143 kilobytes.

3. BACKGROUND

The stereoselective reduction of an α-halo-ketone to its corresponding chiral halo-alcohol is a transformation found in many useful synthetic routes. For example, a synthetic route to the antiviral compound, atazanavir, involves the reduction of a Boc-chloro-ketone derived from L-phenylalanine to the corresponding chiral Boc-(S)-chloro-alcohol. Standard chemical techniques for carrying out this transformation result in diastereomeric mixtures of the desired intermediate that require further resolution, increasing cost and lowering efficiency in the production of atazanavir. Accordingly, processes and compositions capable of more efficient stereoselective reductions of α-halo-ketones to chiral halo-alcohols would be desirable.

Certain enzymes belonging to the ketoreductase (KRED) or carbonyl reductase class (EC1.1.1.184) have been found to be useful for the stereoselective conversion of pro-stereoisomeric aldehyde or ketone substrates to the corresponding chiral alcohol products. KREDs typically convert a ketone or aldehyde substrate to the corresponding alcohol product, but may also catalyze the reverse reaction, oxidation of an alcohol substrate to the corresponding ketone/aldehyde product. The reduction of ketones and aldehydes and the oxidation of alcohols by enzymes such as KRED requires a co-factor, most commonly reduced nicotinamide adenine dinucleotide (NADH) or reduced nicotinamide adenine dinucleotide phosphate (NADPH), and nicotinamide adenine dinucleotide (NAD) or nicotinamide adenine dinucleotide phosphate (NADP) for the oxidation reaction. NADH and NADPH serve as electron donors, while NAD and NADP serve as electron acceptors.

KREDs are increasingly being used for the stereoselective conversion of ketones and aldehydes to chiral alcohols compounds used in the production of key pharmaceutical compounds. Examples using KREDs to generate useful chemical compounds include asymmetric reduction of 4-chloroacetoacetate esters (Zhou, J. Am. Chem. Soc. 1983 105:5925-5926; Santaniello, J. Chem. Res. (S) 1984:132-133; U.S. Pat. No. 5,559,030; U.S. Pat. No. 5,700,670 and U.S. Pat. No. 5,891,685), reduction of dioxocarboxylic acids (e.g., U.S. Pat. No. 6,399,339), reduction of tert-butyl (S) chloro-5-hydroxy-3-oxohexanoate (e.g., U.S. Pat. No. 6,645,746 and WO 01/40450), reduction of pyrrolotriazine-based compounds (e.g., U.S. application No. 2006/0286646); reduction of substituted acetophenones (e.g., U.S. Pat. No. 6,800,477); and reduction of ketothiolanes (WO 2005/054491). In another approach, as demonstrated herein, the ketoreduction can be carried out in the presence of an alcohol, such as isopropanol, to provide a substrate for the reverse reaction (alcohol dehydrogenation). In this manner, the NADH/NADPH consumed in the ketoreduction reaction is regenerated by the reverse, oxidative reaction.

U.S. Pat. No. 7,083,973 discloses a stereoselective process for the preparation of (3S,2R)-1-halo-2-hydroxy-3-(protected)amino-4-substituted butanes by the reduction of the corresponding keto group containing compounds using certain species of *Rhodococcus* and *Brevibacterium*. The '973 patent discloses that only selected species of *Rhodococcus* and *Brevibacterium* catalyze the reduction to form the desired (3S,2R)-1-halo-2-hydroxy-3-(protected)amino-4-substituted butanes in high quantitative and enantiomeric yield. The '973 patent discloses that 10 mL of cell extract from 150 g of *Rhodococcus erythropolis* ATCC 4277 cells loaded with 10 mg of (1S)-[N-(1-benzyl-2-oxo-3-chloro)propyl]carbamic acid t-butyl ester substrate, glucose dehydrogenase (35 units), 0.7 mM NAD$^+$ and 200 mg of glucose (reaction carried out at pH 6.0, 150 RPM agitation and 30° C.) results in (1S,2R)-[N-(1-benzyl-2-hydroxy-3-chloro)propyl]carbamic acid t-butyl ester product in 95% yield with >98% diastereomeric purity.

Accordingly, isolated KRED polypeptides capable of stereoselective conversion of α-halo-ketones to chiral halo-alcohols in high-yield and high diastereomeric purity would be desirable. Also, improved processes for using KRED polypeptides to carry out large-scale preparation of chiral halo-alcohols would be desirable.

4. SUMMARY

The present disclosure provides ketoreductase polypeptides capable of stereoselectively converting an α-halo-ketone to a chiral halo-alcohol, and methods for using these polypeptides in synthetic processes for making chemical compounds such as intermediates in the production of active pharmaceutical ingredients, such as the antiretroviral drug, atazanavir.

In certain embodiments, the disclosure provides ketoreductase polypeptides capable of converting N-protected (S)-3-amino-1-chloro-4-phenylbutan-2-one compounds of Formula (I) (in which $R^1$ is a protecting group) to the corresponding stereoisomeric alcohol N-protected (2R,3S)-3-amino-1-chloro-4-phenylbutan-2-ol product of Formula (II), as depicted in Scheme 1 below:

Scheme 1

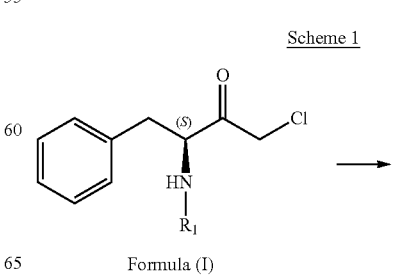

Formula (I)

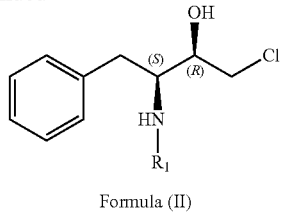

Formula (II)

In particular embodiments, the present disclosure provides ketoreductase polypeptides capable of converting chloroketone compound (1) ((S)-tert-butyl 4-chloro-3-oxo-1-phenylbutan-2-ylcarbamate) to the corresponding alcohol, compound (2) (tert-butyl(2S,3R)-4-chloro-3-hydroxy-1-phenylbutan-2-ylcarbamate), as depicted in Scheme 2 below:

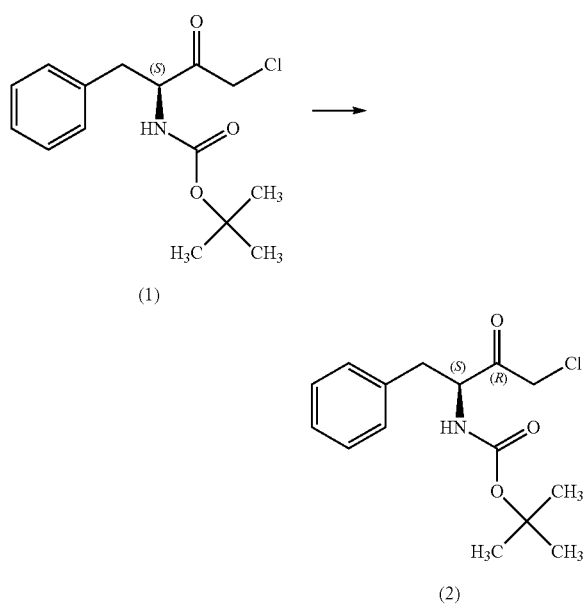

In certain embodiments, the present disclosure provides ketoreductase polypeptides capable of converting a reaction mixture comprising an initial concentration of at least 10 g/L compound (1) to compound (2) with a conversion rate of at least 70% in 24 hours. In certain embodiments, the concentration of polypeptide capable of carrying out this conversion is 5 g/L, 2 g/L, 1 g/L, or less. In certain embodiments, the polypeptides are capable of a conversion rate of at least 80%, 85%, 90%, 95%, 98%, 99% or more in 24 hours, or even less time. In certain embodiments, the polypeptides are capable of converting compound (1) to compound (2) in a diastereomeric excess of greater than about 95%, greater than about 97%, or greater than about 99%. In certain embodiments, the polypeptides are capable of the above conversion rates with a reaction mixture comprising an initial concentration of compound (1) of at least 20 g/L, 40 g/L, 60 g/L, 80 g/L, 100 g/L, 150 g/L, 200 g/L, or even more.

In certain embodiments, the present disclosure provides a method for converting a compound of Formula (I) to a compound of Formula (III) (see Scheme 3), wherein $R^1$ is as described above, comprising converting the compound of Formula (I) to a compound of Formula (II) using a ketoreductase of the present disclosure and then contacting the compound of Formula (II) with base to provide the compound of Formula (III).

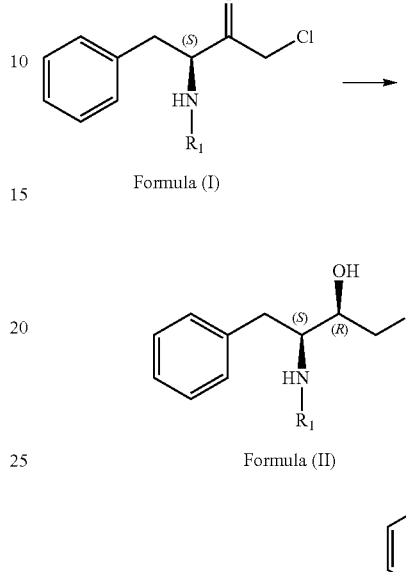

In certain embodiments, the method further comprises extracting the reaction mixture comprising the compound of Formula (II) into an organic solvent extract and contacting the extract with base. In certain embodiments, the method further comprises exchanging the organic solvent extract with a crystallization solvent and crystallizing the compound of Formula (III). In certain embodiments, the step of contacting the compound of Formula (II) with base is carried out without first purifying and/or isolating the compound of Formula (II).

In a specific embodiment, therefore, the present disclosure provides a method for converting compound (1) to compound (3) (tert-butyl(S)-1-((R)-oxiran-2-yl)-2-phenylethylcarbamate) comprising converting compound (1) to compound (2) using a ketoreductase of the present disclosure and then contacting compound (2) with base to provide compound (3) (see Scheme 4).

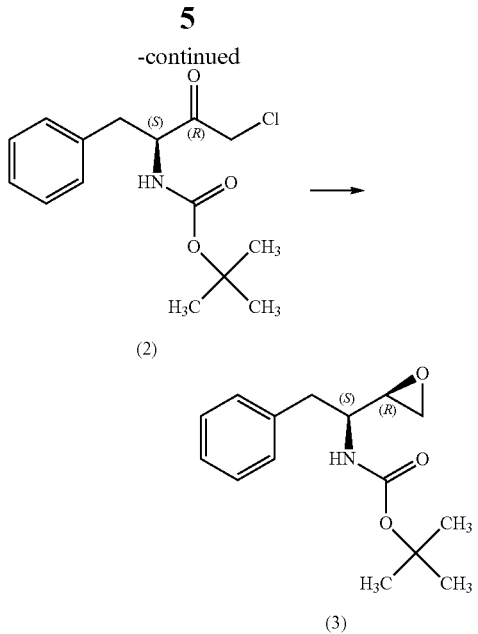

In certain embodiments, the method further comprises extracting the reaction mixture comprising the compound (2) into an organic solvent extract and contacting the extract with base. In certain embodiments, the method further comprises exchanging the organic solvent extract with a crystallization solvent and crystallizing the compound (3). In certain embodiments, the step of contacting the compound (2) with base is carried out without first purifying and/or isolating compound (2).

In some embodiments, the method for reducing or converting the substrate, N-protected (S)-3-amino-1-chloro-4-phenylbutan-2-one (e.g. compound (1)) to its corresponding stereoisomeric alcohol product, N-protected (2R,3S)-3-amino-1-chloro-4-phenylbutan-2-ol (e.g., compound (2)), comprises contacting or incubating the substrate with at least one of the ketoreductase polypeptides disclosed herein under reaction conditions suitable for reducing or converting the substrate to the product.

In some embodiments of the above methods, the substrate is reduced to the product in greater than about 95%, greater than about 97%, or greater than about 99% diastereomeric excess, wherein the ketoreductase polypeptide comprises a sequence that corresponds to SEQ ID NO: 4, 6, 8, 10, 12, 14, 16, 18, 20, 22, 24, 26, 28, 30, 32, 34, 36, 38, 40, 42, 44, 46, 48, 50, 52, 54, 56 and 58.

In certain embodiments of the above methods, at least about 95% of the substrate is converted to the product in less than about 24 hours when carried out with greater than about 100 g/L of substrate and less than about 5 g/L of the polypeptide. In certain embodiments, the polypeptide capable of carrying out the method comprises an amino acid sequence corresponding to SEQ ID NO: 6, 50, 52, and 56. In some embodiments of the above methods, at least about 95% of the substrate is converted to the product in less than about 30 hours when carried out with greater than about 150 g/L of substrate and less than about 1 g/L of the polypeptide, wherein the polypeptide comprises an amino acid sequence corresponding to SEQ ID NO: 6, 50, 52, and 56.

In one aspect, the ketoreductase polypeptides described herein have amino acid sequences with one or more amino acid differences as compared to a wild-type ketoreductase or as compared to an engineered ketoreductase. The one or more amino acid differences result in at least one improved property of the enzyme for a defined substrate. Generally, the ketoreductase polypeptides described herein are engineered ketoreductase polypeptides having one or more improved properties as compared to the naturally-occurring wild-type ketoreductase enzymes obtained from *Novosphingobium aromaticivorans* ("*N. aromaticivorans*"; SEQ ID NO:2). Improvements in an enzyme property of the engineered ketoreductase polypeptides include increases in enzyme activity, stereoselectivity, sterospecificity, thermostability, solvent stability, tolerance to increased levels of substrate, and tolerance to increased levels product.

In some embodiments, the ketoreductase polypeptides of the invention are improved as compared to SEQ ID NO:2 with respect to their rate of enzymatic activity, i.e., the conversion rate for reducing N-protected (S)-3-amino-1-chloro-4-phenylbutan-2-one ("the substrate") (e.g. compound (1) where the protecting group is a BOC moiety) to N-protected (2R, 3S)-3-amino-1-chloro-4-phenylbutan-2-ol ("the product") (e.g., compound (2)). In some embodiments, the engineered ketoreductase polypeptides are capable of converting the substrate to the product at a conversion rate that is at least at least 1.1-times, 1.2-times, 1.3-times, 1.5-times, 2-times, 3-times, or more than 3-times the rate exhibited by the enzyme of SEQ ID NO: 2 under comparable assay conditions.

In some embodiments, such ketoreductase polypeptides are also capable of converting the N-protected (S)-3-amino-1-chloro-4-phenylbutan-2-one ("the substrate") (e.g., compound (1) where the protecting group is a BOC moiety) to N-protected (2R,3S)-3-amino-1-chloro-4-phenylbutan-2-ol ("the product") (e.g. compound (2)), with a percent diastereomeric excess of at least about 95%. In some embodiments, such ketoreductase polypeptides are also capable of converting the substrate to the product with a percent diastereomeric excess of at least about 97%. In some embodiments, such ketoreductase polypeptides are also capable of converting the substrate to the product with a percent diastereomeric excess of at least about 99%. Exemplary polypeptides with such properties include, but are not limited to, polypeptides which comprising amino acid sequences corresponding to SEQ ID NO: 4, 6, 8, 10, 12, 14, 16, 18, 20, 22, 24, 26, 28, 30, 32, 34, 36, 38, 40, 42, 44, 46, 48, 50, 52, 54, 56 and 58.

In some embodiments, the ketoreductase polypeptide is capable of converting N-protected (S)-3-amino-1-chloro-4-phenylbutan-2-one ("the substrate") (e.g. compound (1)) where the protecting group is a BOC moiety) to N-protected (2R,3S)-3-amino-1-chloro-4-phenylbutan-2-ol ("the product") (e.g. compound (2)), with a percent diastereomeric excess of at least about 99% and at a conversion rate that is at least about 1.2 times or more improved over the polypeptide of SEQ ID NO:2. Exemplary polypeptides with such properties include, but are not limited to, polypeptides which comprise an amino acid sequence corresponding to SEQ ID NO: 4, 6, 14, 16, 18, 22, 24, 26, 28, 30, 32, 34, 36, 38, 40, 50, 52, 54, and 56.

In some embodiments, the ketoreductase polypeptide is capable of converting N-protected (S)-3-amino-1-chloro-4-phenylbutan-2-one ("the substrate") (e.g., compound (1) where the protecting group is a BOC moiety) to N-protected (2R,3S)-3-amino-1-chloro-4-phenylbutan-2-ol ("the product") (e.g. compound (2)), with a percent diastereomeric excess of at least about 99% and at a conversion rate that is at least about 1.5 times or more improved over the polypeptide of SEQ ID NO:2. Exemplary polypeptides with such properties include, but are not limited to, polypeptides which comprise an amino acid sequence corresponding to SEQ ID NO: 6, 18, 22, 30, 38, 40, 50, 52, 54, and 56.

In some embodiments, the ketoreductase polypeptide is capable of converting N-protected (S)-3-amino-1-chloro-4-phenylbutan-2-one ("the substrate") (e.g. compound (1) where the protecting group is a BOC moiety) to N-protected (2R,3S)-3-amino-1-chloro-4-phenylbutan-2-ol ("the product") (e.g. compound (2)), with a percent diastereomeric excess of at least about 99% and at a conversion rate that is more than 3 times improved over the polypeptide of SEQ ID NO:2. Exemplary polypeptides with such properties include, but are not limited to, polypeptides which comprise an amino acid sequence corresponding to SEQ ID NO: 6, 50, 52, and 56.

In some embodiments, the ketoreductase polypeptide is capable of converting at least about 95% of the substrate to the product in less than about 24 hours when carried out with greater than about 100 g/L of substrate and less than about 5 g/L of the polypeptide. Exemplary polypeptides that have this capability include, but are not limited to, polypeptides which comprise amino acid sequences corresponding to SEQ ID NO: 6, 50, 52, and 56.

In some embodiments, the ketoreductase polypeptide is highly stereoselective, wherein the polypeptide can reduce the substrate to the product in greater than about 99%, 99.1%, 99.2%, 99.3%, 99.4%, 99.5%, 99.6%, 99.7%, 99.8% or 99.9% diastereomeric excess. Exemplary ketoreductase polypeptides with high stereoselectivity include, but are not limited to, the polypeptides comprising the amino acid sequences corresponding to SEQ ID NO: 4, 6, 8, 10, 12, 14, 16, 18, 20, 22, 24, 26, 28, 30, 32, 34, 36, 38, 40, 42, 44, 46, 48, 50, 52, 54, 56 and 58.

In some embodiments, the ketoreductase polypeptide has the improved property of increased activity with a secondary alcohol for cofactor regeneration. In some embodiments, the ketoreductase polypeptide oxidizes isopropanol (IPA) to acetone with an activity at least 2-fold, 2.5-fold, 5-fold, 10-fold, 15-fold, or even greater, relative to the reference polypeptide of SEQ ID NO: 2. Exemplary ketoreductase polypeptides exhibiting the improved property of increased activity with IPA include, but are not limited to, the polypeptides comprising the amino acid sequence corresponding to SEQ ID NO: 6, 56, 60, 62, 64, 66, 68, 70, 72, 74, 76, 78, and 80.

In certain embodiments, a ketoreductase polypeptide of the present disclosure is at least about 70%, 71%, 72%, 73%, 74%, 75%, 76%, 77%, 78%, 79%, 80%, 81%, 82%, 83%, 84%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to the reference sequence of SEQ ID NO:2, and has, at the position corresponding to the indicated position of SEQ ID NO:2, at least one of the following amino acid differences: the amino acid at position 2 is an aliphatic or nonpolar amino acid selected from among alanine, leucine, valine, isoleucine, glycine and methionine; the amino acid at position 28 is an aliphatic or nonpolar amino acid selected from among alanine, leucine, valine, isoleucine, glycine and methionine; the amino acid at position 34 is a polar amino acid selected from among asparagine, glutamine, serine, and threonine; the amino acid at position 47 is an aliphatic or nonpolar amino acid selected from among alanine, leucine, valine, isoleucine, glycine and methionine; the amino acid at position 50 is a basic amino acid selected from lysine and arginine; the amino acid at position 81 is a polar amino acid selected from among asparagine, glutamine, serine, and threonine; the amino acid at position 90 is an aliphatic or nonpolar amino acid selected from among alanine, leucine, valine, isoleucine, glycine and methionine; the amino acid at position 91 is either an aliphatic or nonpolar amino acid selected from among alanine, leucine, valine, isoleucine, glycine and methionine, or the amino acid at position 91 is an aromatic amino acid selected from among tyrosine, tryptophan, and phenylalanine, or the amino acid at position 91 basic amino acid selected from among lysine and arginine; the amino acid at position 94 is the basic amino acid, arginine; the amino acid at position 112 is an aromatic amino acid selected from among tyrosine, tryptophan, and phenylalanine; the amino acid at position 117 is an acidic amino acid selected from among aspartic acid and glutamic acid; the amino acid at position 143 is a basic amino acid selected from among lysine and arginine; the amino acid at position 144 is either a cysteine, or the amino acid at position 144 is a polar amino acid selected from among asparagine, glutamine, serine, and threonine; the amino acid at position 145 is either a nonpolar amino acid selected from among alanine, leucine, valine, isoleucine, and methionine or an aliphatic amino acid selected from among alanine, leucine, valine, isoleucine; the amino acid at position 148 is a constrained amino acid selected from among proline and histidine; the amino acid at position 150 is either a nonpolar or aliphatic amino acid selected from among leucine, valine, isoleucine, glycine and methionine, or the amino acid at position 150 is a polar amino acid selected from among asparagine, glutamine, serine, and threonine, or the amino acid at position 150 is an aromatic amino acid selected from among tyrosine, tryptophan, and phenylalanine; the amino acid at position 152 is a nonpolar or aliphatic amino acid selected from among alanine, leucine, valine, isoleucine, glycine and methionine; the amino acid at position 153 is either a nonpolar or aliphatic amino acid selected from among alanine, leucine, valine, isoleucine, glycine and methionine, or a constrained amino acid selected from among histidine and proline; the amino acid at position 158 is a polar amino acid selected from among asparagine, glutamine, and serine; the amino acid at position 190 is either a nonpolar or an aliphatic amino acid selected from among alanine, valine, leucine, isoleucine, glycine, and methionine, or the amino acid at position 190 is a polar amino acid selected from among asparagine, glutamine, and serine, or the amino acid at position 190 is a proline; the amino acid at position 198 is a polar amino acid selected from among asparagine, glutamine, and threonine; the amino acid at position 199 is either an aliphatic or nonpolar amino acid selected from among alanine, leucine, valine, glycine, and methionine, or a polar amino acid selected from among asparagine, glutamine, serine, and threonine; the amino acid at position 200 is a nonpolar amino acid selected from among alanine, leucine, valine, isoleucine, and glycine; the amino acid at position 204 is an aromatic amino acid selected from among tyrosine, tryptophan, and phenylalanine; the amino acid at position 217 is a polar amino acid selected from among asparagine, glutamine, serine and threonine; the amino acid at position 225 is a nonpolar amino acid selected from among valine, leucine, glycine, and methionine; the amino acid at position 231 is an aromatic amino acid selected from among tyrosine, tryptophan, and phenylalanine; the amino acid at position 232 is a nonpolar amino acid selected from among leucine, isoleucine, valine, glycine, and methionine; the amino acid at position 233 is a polar amino acid selected from among asparagine, glutamine, serine, and threonine; the amino acid at position 244 is a nonpolar amino acid selected from among alanine, leucine, isoleucine, valine, glycine, and methionine; the amino acid at position 260 is an aromatic amino acid selected from among tyrosine and tryptophan; and the amino acid at position 261 is a polar amino acid selected from among asparagine, glutamine, and threonine.

In certain embodiments, a ketoreductase polypeptide of the present disclosure is at least about 70%, 71%, 72%, 73%, 74%, 75%, 76%, 77%, 78%, 79%, 80%, 81%, 82%, 83%, 84%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to the reference sequence of SEQ ID NO:2, and has, as compared to SEQ ID NO:2, at least one amino acid substitution selected from the group consisting of: P2L; V28A; A34S; A47V; E50K; D81N; S90V; I91L; I91W; I91R; I91K; K94R; D112Y; G117D; S143R; V144C; V144T; G145A; G145V; R148H; A150G; A150I; A150S; A150W; F152L; N153G; N153V; N153H; T158S; G190A; G190P; G190Q; G190V; S198N; I199G; I199L; I199M; I199N; M200I; V204F; A217T; I225V; P231F; A232V; E233Q; D244G; F260Y; S261N; and mixtures thereof.

In some embodiments, an improved ketoreductase polypeptide of the disclosure is based on the sequence of SEQ ID NO:2 and comprises an amino acid sequence that is at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to the reference sequence of SEQ ID NO:2, and further comprises at least one amino acid substitution selected from the group consisting of: the proline residue at position 2 is replaced with leucine; the valine residue at position 28 is replaced with alanine; the alanine residue at position 34 is replaced with serine; the alanine residue at position 47 is replaced with valine; the glutamic acid residue at position 50 is replaced with lysine; the aspartic acid residue at position 81 is replaced with asparagine; the serine residue at position 90 is replaced with valine; the isoleucine residue at position 91 is replaced with an amino acid selected from among leucine, tryptophan, arginine, and lysine; the lysine residue at position 94 is replaced with arginine; the aspartic acid residue at position 112 is replaced with tyrosine; the glycine residue at position 117 is replaced with aspartic acid; the serine residue at position 143 is replaced with arginine; the valine residue at position 144 is replaced with an amino acid selected from among cysteine and threonine; the glycine residue at position 145 is replaced with an amino acid selected from among alanine and valine; the arginine residue at position 148 is replaced with histidine; the alanine residue at position 150 is replaced with an amino acid selected from among glycine, isoleucine, serine, and tryptophan; the phenylalanine residue at position 152 is replaced with leucine; the asparagine residue at position 153 is replaced with an amino acid selected from among glycine, valine, and histidine; the threonine residue at position 158 is replaced with serine; the glycine residue at position 190 is replaced with an amino acid selected from among alanine, proline, glutamine, and valine; the serine residue at position 198 is replaced with asparagine; the isoleucine residue at position 199 is replaced with an amino acid selected from among glycine, methionine, leucine, and asparagine; the methionine residue at position 200 is replaced with isoleucine; the valine residue at position 204 is replaced with phenylalanine; the alanine residue at position 217 is replaced with threonine; the isoleucine residue at position 225 is replaced with valine; the proline residue at position 231 is replaced with phenylalanine; the alanine residue at position 232 is replaced with valine; the glutamic acid residue at position 233 is replaced with glutamine; the aspartic acid residue at position 244 is replaced with glycine; the phenylalanine residue at position 260 is replaced with tyrosine; and the serine residue at position 261 is replaced with asparagine.

In some embodiments, the ketoreductase polypeptides can have, in addition to the above, one or more modifications (i.e., residue differences) as compared to the reference amino acid sequence or as compared to any of SEQ ID NO:4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, or 80. These modifications can be amino acid insertions, deletions, substitutions, or any combination of such changes. In some embodiments, the amino acid sequence differences can comprise non-conservative, conservative, as well as a combination of non-conservative and conservative amino acid substitutions. In some embodiments, these ketoreductase polypeptides can have optionally from about 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 mutations at other amino acid residues. In some embodiments, the number of modifications can be 1, 2, 3, 4, 5, 6, 7, 8, 9, 10, 11, 12, 14, 15, 16, 18, 20, 22, 24, 26, 30, 35 or about 40 other amino acid residues.

In some embodiments, an improved ketoreductase comprises an amino acid sequence that is at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to the amino acid sequence corresponding to SEQ ID NO: 2, wherein the improved ketoreductase polypeptide amino acid sequence includes any one set of the specified amino acid substitution combinations presented in Tables 2 or 3. In some embodiments, these ketoreductase polypeptides can have mutations at other amino acid residues.

In another aspect, the present disclosure provides polynucleotides encoding the ketoreductase polypeptides described herein, and polynucleotides that hybridize to such polynucleotides under highly stringent conditions. The polynucleotide can include promoters and other regulatory elements useful for expression of the encoded engineered ketoreductase, and can utilize codons optimized for specific desired expression systems.

In some embodiments, the disclosure provides polynucleotides encoding ketoreductase polypeptides having at least the following amino acid sequence as compared to the amino acid sequence of SEQ ID NO:2, and further comprising at least one amino acid substitution selected from the group consisting of: the proline residue at position 2 is replaced with leucine; the valine residue at position 28 is replaced with alanine; the alanine residue at position 34 is replaced with serine; the alanine residue at position 47 is replaced with valine; the glutamic acid residue at position 50 is replaced with lysine; the aspartic acid residue at position 81 is replaced with asparagine; the serine residue at position 90 is replaced with valine; the isoleucine residue at position 91 is replaced with an amino acid selected from among leucine, tryptophan, arginine, and lysine; the lysine residue at position 94 is replaced with arginine; the aspartic acid residue at position 112 is replaced with tyrosine; the glycine residue at position 117 is replaced with aspartic acid; the serine residue at position 143 is replaced with arginine; the valine residue at position 144 is replaced with an amino acid selected from among cysteine and threonine; the glycine residue at position 145 is replaced with an amino acid selected from among alanine and valine; the arginine residue at position 148 is replaced with histidine; the alanine residue at position 150 is replaced with an amino acid selected from among glycine, isoleucine, serine, and tryptophan; the phenylalanine residue at position 152 is replaced with leucine; the asparagine residue at position 153 is replaced with an amino acid selected from among glycine, valine, and histidine; the threonine residue at position 158 is replaced with serine; the glycine residue at position 190 is replaced with an amino acid selected from among alanine, proline, glutamine, and valine; the serine residue at position 198 is replaced with asparagine; the isoleucine residue at position 199 is replaced with an amino acid selected from among glycine, methionine, leucine, and asparagine; the methionine residue at position 200 is replaced with isoleucine; the valine residue at position 204 is replaced with phenylalanine; the alanine residue at position 217 is replaced with threonine; the isoleucine residue at position 225 is replaced with valine; the proline residue at position 231 is replaced with phenylalanine; the alanine residue at position 232 is replaced with valine; the glutamic acid residue at position 233 is replaced with glutamine; the aspartic acid residue at position 244 is replaced with glycine; the phenylalanine residue at position 260 is replaced with tyrosine; and the serine residue at position 261 is replaced with asparagine. Exemplary polynucleotides include, but are not limited to, a polynucleotide sequence of SEQ ID NO: 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, and 79.

In some embodiments, the present disclosure provides host cells comprising the polynucleotides encoding the ketoreductase polypeptides as described herein and/or expression vectors comprising these polynucleotides. The host cells may be N. aromaticivorans or they may be a different organism, and as E. coli. The host cells can be used for the expression and isolation of the engineered ketoreductase enzymes described herein, or, alternatively, they can be used directly for the conversion of the substrate to the stereoisomeric product. Accordingly, in some embodiments, the engineered ketoreductase polypeptides disclosed herein can be prepared by standard methods comprising culturing a host cell containing an expression vector comprising a polynucleotide encoding the polypeptide and isolating the polypeptide from the host cell.

Whether carrying out the method with whole cells, cell extracts or purified ketoreductase enzymes, a single ketoreductase enzyme may be used or, alternatively, mixtures of two or more ketoreductase enzymes may be used.

5. DETAILED DESCRIPTION

Other than in the operating examples, or where otherwise indicated, all numbers expressing quantities of ingredients, reaction conditions, and so forth used in the specification and claims are to be understood as being modified in all instances by the term "about."

In this disclosure, the use of the singular includes the plural (and vice versa) unless specifically stated otherwise. Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

It is to be understood that both the foregoing general description, including the drawings, and the following detailed description are exemplary and explanatory only and are not restrictive of this disclosure.

The section headings used herein are for organizational purposes only and not to be construed as limiting the subject matter described.

The present disclosure is directed to biocatalytic processes in which α-chloroketones are contacted with a ketoreductase enzyme and thereby concerted to the corresponding α-chloro alcohol. The present disclosure therefore provides ketoreductase enzymes capable of converting N-protected (S)-3-amino-1-chloro-4-phenylbutan-2-one ("the substrate") (e.g. compound (1) where the protecting group is a BOC moiety) to the corresponding stereoisomeric alcohol product N-protected (2R,3S)-3-amino-1-chloro-4-phenylbutan-2-ol ("the product") (e.g. compound (2)). The present disclosure further comprises a method for converting that alcohol product, an N-protected (2R,3S)-3-amino-1-chloro-4-phenylbutan-2-ol (e.g. compound (2)), to the corresponding stereoisomeric epoxide, N-protected (S)-1-((R)-oxiran-2-yl)-2-phenylethylcarbamate), e.g. compound (3) (tert-butyl(S)-1-((R)-oxiran-2-yl)-2-phenylethylcarbamate; where the protecting group is a BOC moiety).

5.1. Definitions

As used herein, the following terms are intended to have the following meanings:

The term "protecting group" refers to a group of atoms that when attached to a reactive functional group in a molecule, mask, reduce or prevent the reactivity of the functional group. Typically, a protecting group may be selectively removed as desired during the course of a synthesis.

"Nitrogen protecting group" (or "N-protecting group") means a substituent commonly employed to block or protect a nitrogen functionality while reacting other functional groups on a compound. Examples of such nitrogen-protecting groups include the formyl group, the trityl group, the methoxytrityl group, the tosyl group, the phthalimido group, the acetyl group, the trichloroacetyl group, the chloroacetyl, bromoacetyl, and iodoacetyl groups, benzyloxycarbonyl (Cbz), 9-fluorenylmethoxycarbonyl (FMOC), 2-trimethylsilylethoxycarbonyl (Teoc), 1-methyl-1-(4-biphenylyl)ethoxycarbonyl (Bpoc), t-butoxycarbonyl (BOC), allyloxycarbonyl (Alloc), trihaloacetyl, benzyl, benzoyl, and nitrophenylacetyl and the like. Further examples of protecting groups useful with the embodiments of the present disclosure can be found in P. G. M. Wuts and T. W. Greene, "Greene's Protective Groups in Organic Synthesis—Fourth Edition," John Wiley and Sons, New York, N.Y., 2007, Chapter 7 ("Greene").

"Stereoisomer," "stereoisomeric form," and the like are general terms for all isomers of individual molecules that differ only in the orientation of their atoms in space. In includes enantiomers and isomers of compounds with more than one chiral center that are not mirror images of one another ("diastereomers").

"Chiral center" refers to a carbon atom to which four different groups are attached.

"Enantiomer" or "enantiomeric" refers to a molecule that is nonsuperimposable on its mirror image and hence optically active where the enantiomer rotates the plane of polarized light in one direction and its mirror image rotates the plane of polarized light in the opposite direction.

"Enantiomeric excess," "(ee)," "diastereomeric excess," "(de)," means that one enantiomer or diastereomer is present more than the other in a chemical substance. This difference is defined as the absolute difference between the mole fractions of each enantiomer: ee=|(F+)−(F−)|, where (F+)+(F−)= 1. Thus, (ee) and (de) can expressed as a percent enantiomeric or diastereomeric excess.

The term "racemic" refers to a mixture of equal molar amounts of two enantiomers of a compound, which mixture is optically inactive.

As used herein, a composition is "enriched" in a particular chiral compound, enantiomer, or diastereomer will typically comprise at least about 60%, 70%, 80%, 90%, or even more of that particular chiral compound, enantiomer, or diastereomer. The amount of enrichment can be determined using conventional analytical methods routinely used by those of ordinary skill in the art, including but not limited to, NMR spectroscopy in the presence of chiral shift reagents, gas chromatographic analysis using chiral columns, and high pressure liquid chromatographic analysis using chiral columns. In some embodiments a single chiral compound, enantiomer, or diastereomer will be substantially free of other corresponding chiral compound, enantiomer, or diastereomers. By "substantially free" is meant that the composition comprises less than about 10% of the specified undesired chiral compound, enantiomer, or diastereomer as established using conventional analytical methods routinely used by those of ordinary skill in the art, such as the methods noted above. In some embodiments, the amount of undesired chiral compound, enantiomer, or diastereomer may be less than about 10%, for example, less than about 9%, 8%, 7%, 6%, 5%, 4%, 3%, 2%, 1% or even less. Chirally enantiomerically, or diastereomerically enriched compositions that contain at least about 95% of a specified chiral compound, enantiomer, or diastereomer are referred to herein as "substantially chirally pure," "substantially enantiomerically pure" and "substantially diastereomerically pure," respectively. Compositions that contain at least about 99% of a specified chiral compound, enantiomer, or diastereomer are referred to herein as "chirally pure," "enantiomerically pure," and "diastereomerically pure," respectively.

"Ketoreductase" and "KRED" are used interchangeably herein to refer to a polypeptide having an enzymatic capability of reducing a carbonyl group to its corresponding alcohol. In specific embodiments, the ketoreductase polypeptides of the invention are capable of stereoselectively reducing (1) ((S)-tert-butyl 4-chloro-3-oxo-1-phenylbutan-2-ylcarbamate) to the corresponding alcohol, compound (2) (tert-butyl (2S,3R)-4-chloro-3-hydroxy-1-phenylbutan-2-ylcarbamate). The polypeptide typically utilizes a cofactor reduced nicotinamide adenine dinucleotide (NADH) or reduced nicotinamide adenine dinucleotide phosphate (NADPH) as the reducing agent. Ketoreductases as used herein include naturally occurring (wild type) ketoreductases as well as non-naturally occurring engineered polypeptides generated by human manipulation.

"Engineered ketoreductase polypeptide" as used herein refers to an ketoreductase polypeptide having a variant sequence generated by human manipulation (e.g., a sequence generated by directed evolution of a naturally occurring parent enzyme or directed evolution of a variant previously derived from a naturally occurring enzyme).

"Naturally-occurring" or "wild-type" refers to the form found in nature. For example, a naturally occurring or wild-type polypeptide or polynucleotide sequence is a sequence present in an organism that can be isolated from a source in nature and which has not been intentionally modified by human manipulation.

"Protein," "polypeptide," and "peptide" are used interchangeably herein to denote a polymer of at least two amino acids covalently linked by an amide bond, regardless of length or post-translational modification (e.g., glycosylation, phosphorylation, lipidation, myristilation, ubiquitination, etc.). Included within this definition are D- and L-amino acids, and mixtures of D- and L-amino acids.

"Polynucleotides" or "oligonucleotides" refer to nucleobase polymers or oligomers in which the nucleobases are connected by sugar phosphate linkages (sugar-phosphate backbone). Nucleobase or base include naturally occurring and synthetic heterocyclic moieties commonly known to those who utilize nucleic acid or polynucleotide technology or utilize polyamide or peptide nucleic acid technology to thereby generate polymers that can hybridize to polynucleotides in a sequence-specific manner. Non-limiting examples of nucleobases include: adenine, cytosine, guanine, thymine, uracil, 5-propynyl-uracil, 2-thio-5-propynyl-uracil, 5-methylcytosine, pseudoisocytosine, 2-thiouracil and 2-thiothymine, 2-aminopurine, N9-(2-amino-6-chloropurine), N9-(2,6-diaminopurine), hypoxanthine, N9-(7-deaza-guanine), N9-(7-deaza-8-aza-guanine) and N8-(7-deaza-8-aza-adenine). Exemplary poly- and oligonucleotides include polymers of 2' deoxyribonucleotides (DNA) and polymers of ribonucleotides (RNA). A polynucleotide may be composed entirely of ribonucleotides, entirely of 2' deoxyribonucleotides or combinations thereof.

"Coding sequence" refers to that portion of a polynucleotide (e.g., a gene) that encodes an amino acid sequence of a polypeptide (e.g., a protein).

"Percentage of sequence identity," "percent identity," and "percent identical" are used herein to refer to comparisons between polynucleotide sequences or polypeptide sequences, and are determined by comparing two optimally aligned sequences over a comparison window, wherein the portion of the polynucleotide or polypeptide sequence in the comparison window may comprise additions or deletions (i.e., gaps) as compared to the reference sequence for optimal alignment of the two sequences. The percentage is calculated by determining the number of positions at which either the identical nucleic acid base or amino acid residue occurs in both sequences or a nucleic acid base or amino acid residue is aligned with a gap to yield the number of matched positions, dividing the number of matched positions by the total number of positions in the window of comparison and multiplying the result by 100 to yield the percentage of sequence identity. Determination of optimal alignment and percent sequence identity is performed using the BLAST and BLAST 2.0 algorithms (see e.g., Altschul et al., 1990, J. Mol. Biol. 215: 403-410 and Altschul et al., 1977, Nucleic Acids Res. 3389-3402). Software for performing BLAST analyses is publicly available through the National Center for Biotechnology Information website.

Briefly, the BLAST analyses involve first identifying high scoring sequence pairs (HSPs) by identifying short words of length W in the query sequence, which either match or satisfy some positive-valued threshold score T when aligned with a word of the same length in a database sequence. T is referred to as, the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff and Henikoff, 1989, Proc Natl Acad Sci USA 89:10915).

Other algorithms are available that function similarly to BLAST in providing percent identity for two sequences. Optimal alignment of sequences for comparison can be conducted, e.g., by the local homology algorithm of Smith and Waterman, 1981, Adv. Appl. Math. 2:482, by the homology alignment algorithm of Needleman and Wunsch, 1970, J. Mol. Biol. 48:443, by the search for similarity method of Pearson and Lipman, 1988, Proc. Natl. Acad. Sci. USA 85:2444, by computerized implementations of these algorithms (GAP, BESTFIT, FASTA, and TFASTA in the GCG Wisconsin Software Package), or by visual inspection (see generally, Current Protocols in Molecular Biology, F. M. Ausubel et al., eds., Current Protocols, a joint venture between Greene Publishing Associates, Inc. and John Wiley & Sons, Inc., (1995 Supplement) (Ausubel)). Additionally, determination of sequence alignment and percent sequence identity can employ the BESTFIT or GAP programs in the GCG Wisconsin Software package (Accelrys, Madison Wis.), using default parameters provided.

"Reference sequence" refers to a defined sequence to which an altered sequence is compared. A reference sequence may be a subset of a larger sequence, for example, a segment of a full-length gene or polypeptide sequence. Generally, a reference sequence is at least 20 nucleotide or amino acid residues in length, at least 25 residues in length, at least 50 residues in length, or the full length of the nucleic acid or polypeptide. Since two polynucleotides or polypeptides may each (1) comprise a sequence (i.e., a portion of the complete sequence) that is similar between the two sequences, and (2) may further comprise a sequence that is divergent between the two sequences, sequence comparisons between two (or more) polynucleotides or polypeptide are typically performed by comparing sequences of the two polynucleotides over a comparison window to identify and compare local regions of sequence similarity.

The term "reference sequence" is not intended to be limited to wild-type sequences, and can include engineered or altered sequences. For example, in some embodiments, a "reference sequence" can be a previously engineered or altered amino acid sequence. For instance, a "reference sequence based on SEQ ID NO: 2 having a glycine residue at position X315" refers to a reference sequence corresponding to SEQ ID NO:2 with a glycine residue at X315 (whereas the un-altered version of SEQ ID NO:2 has glutamate at X315).

"Comparison window" refers to a conceptual segment of at least about 20 contiguous nucleotide positions or amino acids residues wherein a sequence may be compared to a reference sequence of at least 20 contiguous nucleotides or amino acids and wherein the portion of the sequence in the comparison window may comprise additions or deletions (i.e., gaps) of 20 percent or less as compared to the reference sequence (which does not comprise additions or deletions) for optimal alignment of the two sequences. The comparison window can be longer than 20 contiguous residues, and includes, optionally 30, 40, 50, 100, or longer windows.

"Substantial identity" refers to a polynucleotide or polypeptide sequence that has at least 80 percent sequence identity, at least 85 percent sequence identity, at least 89 percent sequence identity, at least 95 percent sequence identity, and even at least 99 percent sequence identity as compared to a reference sequence over a comparison window of at least 20 residue positions, frequently over a window of at least 30-50 residues, wherein the percentage of sequence identity is calculated by comparing the reference sequence to a sequence that includes deletions or additions which total 20 percent or less of the reference sequence over the window of comparison. In specific embodiments applied to polypeptides, the term "substantial identity" means that two polypeptide sequences, when optimally aligned, such as by the programs GAP or BESTFIT using default gap weights, share at least 80 percent sequence identity, preferably at least 89 percent sequence identity, at least 95 percent sequence identity or more (e.g., 99 percent sequence identity). Preferably, residue positions which are not identical differ by conservative amino acid substitutions.

"Corresponding to," "reference to," or "relative to" when used in the context of the numbering of a given amino acid or polynucleotide sequence refers to the numbering of the residues of a specified reference sequence when the given amino acid or polynucleotide sequence is compared to the reference sequence. In other words, the residue number or residue position of a given polymer is designated with respect to the reference sequence rather than by the actual numerical position of the residue within the given amino acid or polynucleotide sequence. For example, a given amino acid sequence, such as that of an engineered ketoreductase, can be aligned to a reference sequence by introducing gaps to optimize residue matches between the two sequences. In these cases, although the gaps are present, the numbering of the residue in the given amino acid or polynucleotide sequence is made with respect to the reference sequence to which it has been aligned.

"Derived from" as used herein in the context of engineered enzymes identifies the originating enzyme, and/or the gene encoding such enzyme, upon which the engineering was based. For example, the engineered ketoreductase enzyme having variant polypeptide sequence SEQ ID NO: 6 was obtained by artificially mutating, over multiple generations the polynucleotide encoding the wild-type ketoreductase enzyme of SEQ ID NO:2. Thus, this engineered ketoreductase enzyme is "derived from" the wild-type ketoreductase of SEQ ID NO: 2.

"Stereoselectivity" or "stereospecificity" refer to the preferential formation in a chemical or enzymatic reaction of one stereoisomer over another. Stereoselectivity can be partial, where the formation of one stereoisomer is favored over the other, or it may be complete where only one stereoisomer is formed. When the stereoisomers are enantiomers, the stereoselectivity is referred to as enantioselectivity, the fraction (typically reported as a percentage) of one enantiomer in the sum of both. It is commonly alternatively reported in the art (typically as a percentage) as the enantiomeric excess (e.e.) calculated therefrom according to the formula [major enantiomer−minor enantiomer]/[major enantiomer+minor enantiomer]. Where the stereoisomers are diastereoisomers, the stereoselectivity sometimes is referred to as diastereoselectivity, the fraction (typically reported as a percentage) of one diastereomer in a mixture of two diastereomers, commonly alternatively reported as the diastereomeric excess (d.e.). Enantiomeric excess and diastereomeric excess are types of stereomeric excess.

"Highly stereoselective" as used herein refers to a ketoreductase polypeptide that is capable of converting or reducing a substrate to the corresponding product (e.g., compound (1) to compound (2)) with at least about 99% stereomeric excess.

"Improved enzyme property" refers to any enzyme property made better or more desirable for a particular purpose as compared to that property found in a reference enzyme. For the engineered ketoreductase polypeptides described herein, the comparison is generally made to the wild-type ketoreductase enzyme, although in some embodiments, the reference ketoreductase can be another improved engineered ketoreductase. Enzyme properties for which improvement is desirable include, but are not limited to, enzymatic activity (which can be expressed in terms of percent conversion of the substrate in a period of time), thermal stability, pH stability or activity profile, cofactor requirements, refractoriness to inhibitors (e.g., product inhibition), stereospecificity, and stereoselectivity (including enantioselectivity).

"Increased enzymatic activity" or "increased activity" or "increased conversion rate" refers to an improved property of an engineered enzyme, which can be represented by an increase in specific activity (e.g., product produced/time/weight protein) or an increase in conversion rate of the substrate to the product (e.g., percent conversion of starting amount of substrate to product in a specified time period using a specified amount of transaminase) as compared to a reference enzyme. Exemplary methods to determine enzyme activity and conversion rate are provided in the Examples. Any property relating to enzyme activity may be affected, including the classical enzyme properties of $K_m$, $V_{max}$ or $k_{cat}$, changes of which can lead to increased enzymatic activity. Improvements in enzyme activity can be from about 100% improved over the enzymatic activity of the corresponding wild-type ketoreductase enzyme, to as much as 200%, 500%, 1000%, or more over the enzymatic activity of the naturally occurring ketoreductase or another engineered ketoreductase from which the ketoreductase polypeptides were derived. In specific embodiments, the engineered ketoreductase enzyme exhibits improved enzymatic activity in the range of a 100% to 200%, 200% to 1000% or more than a 1500% improvement over that of the parent, wild-type or other reference ketoreductase enzyme. It is understood by the skilled artisan that the activity of any enzyme is diffusion limited such that the catalytic turnover rate cannot exceed the diffusion rate of the substrate, including any required cofactors. The theoretical maximum of the diffusion limit, or $k_{cat}/K_m$, is generally about $10^8$ to $10^9$ ($M^{-1} s^{-1}$). Hence, any improvements in the enzyme activity of the ketoreductase will have an upper limit related to the diffusion rate of the substrates acted on by the ketoreductase enzyme. Ketoreductase activity can be measured by any one of standard assays used for measuring ketoreductase, such as the assay described in Example 7. Comparisons of enzyme activities or conversion rates are made using a defined preparation of enzyme, a defined assay under a set condition, and one or more defined substrates, as further described in detail herein. Generally, when lysates are compared, the numbers of cells and/or the amount of protein assayed are determined as well as use of identical expression systems and identical host cells to minimize variations in amount of enzyme produced by the host cells and present in the lysates.

"Conversion" refers to the enzymatic transformation of a substrate to the corresponding product. "Percent conversion" refers to the percent of the substrate that is converted to the product within a period of time under specified conditions. Thus, for example, the "activity" or "conversion rate" of a ketoreductase polypeptide can be expressed as "percent conversion" of the substrate to the product.

"Thermostable" or "thermal stable" are used interchangeably to refer to a polypeptide that is resistant to inactivation when exposed to a set of temperature conditions (e.g., 40-80° C.) for a period of time (e.g., 0.5-24 hrs) compared to the untreated enzyme, thus retaining a certain level of residual activity (more than 60% to 80% for example) after exposure to elevated temperatures.

"Solvent stable" refers to a polypeptide that maintains similar activity (more than e.g., 60% to 80%) after exposure to varying concentrations (e.g., 5-99%) of solvent, (e.g., isopropyl alcohol, dimethylsulfoxide, tetrahydrofuran, 2-methyltetrahydrofuran, acetone, toluene, butylacetate, methyl tert-butylether, acetonitrile, etc.) for a period of time (e.g., 0.5-24 hrs) compared to the untreated enzyme.

"pH stable" refers to a polypeptide that maintains similar activity (more than e.g. 60% to 80%) after exposure to high or low pH (e.g. 8 to 12 or 4.5-6) for a period of time (e.g. 0.5-24 hrs) compared to the untreated enzyme.

"Thermo- and solvent stable" refers to a polypeptide that is both thermostable and solvent stable.

"Amino acid" or "residue" as used in context of the polypeptides disclosed herein refers to the specific monomer at a sequence position (e.g., E315 indicates that the "amino acid" or "residue" at position 315 of SEQ ID NO: 2 is a glutamate).

"Hydrophilic Amino Acid or Residue" refers to an amino acid or residue having a side chain exhibiting a hydrophobicity of less than zero according to the normalized consensus hydrophobicity scale of Eisenberg et al., 1984, J. Mol. Biol. 179:125-142. Genetically encoded hydrophilic amino acids include L-Thr (T), L-Ser (S), L-His (H), L-Glu (E), L-Asn (N), L-Gln (Q), L-Asp (D), L-Lys (K) and L-Arg (R).

"Acidic Amino Acid or Residue" refers to a hydrophilic amino acid or residue having a side chain exhibiting a pK value of less than about 6 when the amino acid is included in a peptide or polypeptide. Acidic amino acids typically have negatively charged side chains at physiological pH due to loss of a hydrogen ion. Genetically encoded acidic amino acids include L-Glu (E) and L-Asp (D).

"Basic Amino Acid or Residue" refers to a hydrophilic amino acid or residue having a side chain exhibiting a pK value of greater than about 6 when the amino acid is included in a peptide or polypeptide. Basic amino acids typically have positively charged side chains at physiological pH due to association with hydronium ion. Genetically encoded basic amino acids include L-Arg (R) and L-Lys (K).

"Polar Amino Acid or Residue" refers to a hydrophilic amino acid or residue having a side chain that is uncharged at physiological pH, but which has at least one bond in which the pair of electrons shared in common by two atoms is held more closely by one of the atoms. Genetically encoded polar amino acids include L-Asn (N), L-Gln (Q), L-Ser (S) and L-Thr (T).

"Hydrophobic Amino Acid or Residue" refers to an amino acid or residue having a side chain exhibiting a hydrophobicity of greater than zero according to the normalized consensus hydrophobicity scale of Eisenberg et al., 1984, J. Mol. Biol. 179:125-142. Genetically encoded hydrophobic amino acids include L-Pro (P), L-Ile (I), L-Phe (F), L-Val (V), L-Leu (L), L-Trp (W), L-Met (M), L-Ala (A) and L-Tyr (Y).

"Aromatic Amino Acid or Residue" refers to a hydrophilic or hydrophobic amino acid or residue having a side chain that includes at least one aromatic or heteroaromatic ring. Genetically encoded aromatic amino acids include L-Phe (F), L-Tyr (Y) and L-Trp (W). Although owing to the pKa of its heteroaromatic nitrogen atom L His (H) it is sometimes classified as a basic residue, or as an aromatic residue as its side chain includes a heteroaromatic ring, herein histidine is classified as a hydrophilic residue or as a "constrained residue" (see below).

"Constrained amino acid or residue" refers to an amino acid or residue that has a constrained geometry. Herein, constrained residues include L-pro (P) and L-his (H). Histidine has a constrained geometry because it has a relatively small imidazole ring. Proline has a constrained geometry because it also has a five membered ring.

"Non-polar Amino Acid or Residue" refers to a hydrophobic amino acid or residue having a side chain that is uncharged at physiological pH and which has bonds in which the pair of electrons shared in common by two atoms is generally held equally by each of the two atoms (i.e., the side chain is not polar). Genetically encoded non-polar amino acids include L-Gly (G), L-Leu (L), L-Val (V), L-Ile (I), L-Met (M) and L-Ala (A).

"Aliphatic Amino Acid or Residue" refers to a hydrophobic amino acid or residue having an aliphatic hydrocarbon side chain. Genetically encoded aliphatic amino acids include L-Ala (A), L-Val (V), L-Leu (L) and L-Ile (I).

"Cysteine". The amino acid L-Cys (C) is unusual in that it can form disulfide bridges with other L-Cys (C) amino acids or other sulfanyl- or sulfhydryl-containing amino acids. The "cysteine-like residues" include cysteine and other amino acids that contain sulfhydryl moieties that are available for formation of disulfide bridges. The ability of L-Cys (C) (and other amino acids with SH containing side chains) to exist in a peptide in either the reduced free SH or oxidized disulfide-bridged form affects whether L-Cys (C) contributes net hydrophobic or hydrophilic character to a peptide. While L-Cys (C) exhibits a hydrophobicity of 0.29 according to the normalized consensus scale of Eisenberg (Eisenberg et al., 1984, supra), it is to be understood that for purposes of the present disclosure L-Cys (C) is categorized into its own unique group.

"Small Amino Acid or Residue" refers to an amino acid or residue having a side chain that is composed of a total three or fewer carbon and/or heteroatoms (excluding the α-carbon and hydrogens). The small amino acids or residues may be further categorized as aliphatic, non-polar, polar or acidic small amino acids or residues, in accordance with the above definitions. Genetically-encoded small amino acids include L-Ala (A), L-Val (V), L-Cys (C), L-Asn (N), L-Ser (S), L-Thr (T) and L-Asp (D).

"Hydroxyl-containing Amino Acid or Residue" refers to an amino acid containing a hydroxyl (—OH) moiety. Genetically-encoded hydroxyl-containing amino acids include L-Ser (S), L-Thr (T) and L-Tyr (Y).

"Amino acid difference" or "residue difference" refers to a change in the residue at a specified position of a polypeptide sequence when compared to a reference sequence. For example, a residue difference at position 1199, where the reference sequence has a isoleucine, refers to a change of the residue at position 199 to any residue other than isoleucine. As disclosed herein, an engineered ketoreductase enzyme can include one or more residue differences relative to a reference sequence, where multiple residue differences typically are indicated by a list of the specified positions where changes are made relative to the reference sequence (e.g., "one or more residue differences as compared to SEQ ID NO: 2 at the following residue positions: 2, 28, 34, 47, 50, 81, 90, 91, 94, 112, 117, 143, 144, 145, 150, 152, 153, 158, 190, 198, 199, 200, 204, 217, 225, 231, 232, 233, 244, 260, and 261.")

A "conservative" amino acid substitution (or mutation) refers to the substitution of a residue with a residue having a similar side chain, and thus typically involves substitution of the amino acid in the polypeptide with amino acids within the same or similar defined class of amino acids. However, as used herein, in some embodiments, conservative mutations do not include substitutions from a hydrophilic to hydrophilic, hydrophobic to hydrophobic, hydroxyl-containing to hydroxyl-containing, or small to small residue, if the conservative mutation can instead be a substitution from an aliphatic to an aliphatic, non-polar to non-polar, polar to polar, acidic to acidic, basic to basic, aromatic to aromatic, or constrained to constrained residue. Further, as used herein, A, V, L, or I can be conservatively mutated to either another aliphatic residue or to another non-polar residue. Table 1 below shows exemplary conservative substitutions.

TABLE 1

Conservative Substitutions

| Residue | Possible Conservative Mutations |
| --- | --- |
| A, L, V, I | Other aliphatic (A, L, V, I) |
|  | Other non-polar (A, L, V, I, G, M) |
| G, M | Other non-polar (A, L, V, I, G, M) |
| D, E | Other acidic (D, E) |
| K, R | Other basic (K, R) |
| P, H | Other constrained (P, H) |
| N, Q, S, T | Other polar (N, Q, S, T) |
| Y, W, F | Other aromatic (Y, W, F) |
| C | None |

"Non-conservative substitution" refers to substitution or mutation of an amino acid in the polypeptide with an amino acid with significantly differing side chain properties. Non-conservative substitutions may use amino acids between, rather than within, the defined groups listed above. In one embodiment, a non-conservative mutation affects (a) the structure of the peptide backbone in the area of the substitution (e.g., proline for glycine) (b) the charge or hydrophobicity, or (c) the bulk of the side chain.

"Deletion" refers to modification to the polypeptide by removal of one or more amino acids from the reference polypeptide. Deletions can comprise removal of 1 or more amino acids, 2 or more amino acids, 3 or more amino acids, 4 or more amino acids, 5 or more amino acids, 6 or more amino acids, 7 or more amino acids, 8 or more amino acids, 10 or more amino acids, 12 or more amino acids, 15 or more amino acids, or 20 or more amino acids, up to 10% of the total number of amino acids, or up to 20% of the total number of amino acids making up the reference enzyme while retaining enzymatic activity and/or retaining the improved properties of an engineered ketoreductase enzyme. Deletions can be directed to the internal portions and/or terminal portions of the polypeptide. In various embodiments, the deletion can comprise a continuous segment or can be discontinuous.

"Insertion" refers to modification to the polypeptide by addition of one or more amino acids from the reference polypeptide. In some embodiments, the improved engineered ketoreductase enzymes comprise insertions of one or more amino acids to the naturally occurring ketoreductase polypeptide as well as insertions of one or more amino acids to other engineered ketoreductase polypeptides. Insertions can be in the internal portions of the polypeptide, or to the carboxy or amino terminus Insertions as used herein include fusion proteins as is known in the art. The insertion can be a contiguous segment of amino acids or separated by one or more of the amino acids in the naturally occurring polypeptide.

"Fragment" as used herein refers to a polypeptide that has an amino-terminal and/or carboxy-terminal deletion, but where the remaining amino acid sequence is identical to the corresponding positions in the sequence. Fragments can be at least 14 amino acids long, at least 20 amino acids long, at least 50 amino acids long or longer, and up to 70%, 80%, 90%, 95%, 98%, and 99% of a full-length ketoreductase polypeptide.

"Isolated polypeptide" refers to a polypeptide which is substantially separated from other contaminants that naturally accompany it, e.g., protein, lipids, and polynucleotides.

The term embraces polypeptides which have been removed or purified from their naturally-occurring environment or expression system (e.g., host cell or in vitro synthesis). The improved ketoreductase enzymes may be present within a cell, present in the cellular medium, or prepared in various forms, such as lysates or isolated preparations. As such, in some embodiments, the improved ketoreductase enzyme can be an isolated polypeptide.

"Substantially pure polypeptide" refers to a composition in which the polypeptide species is the predominant species present (i.e., on a molar or weight basis it is more abundant than any other individual macromolecular species in the composition), and is generally a substantially purified composition when the object species comprises at least about 50 percent of the macromolecular species present by mole or % weight. Generally, a substantially pure ketoreductase composition will comprise about 60% or more, about 70% or more, about 80% or more, about 90% or more, about 95% or more, and about 98% or more of all macromolecular species by mole or % weight present in the composition. In some embodiments, the object species is purified to essential homogeneity (i.e., contaminant species cannot be detected in the composition by conventional detection methods) wherein the composition consists essentially of a single macromolecular species. Solvent species, small molecules (<500 Daltons), and elemental ion species are not considered macromolecular species. In some embodiments, the isolated improved ketoreductases polypeptide is a substantially pure polypeptide composition.

"Stringent hybridization" is used herein to refer to conditions under which nucleic acid hybrids are stable. As known to those of skill in the art, the stability of hybrids is reflected in the melting temperature (Tm) of the hybrids. In general, the stability of a hybrid is a function of ion strength, temperature, G/C content, and the presence of chaotropic agents. The Tm values for polynucleotides can be calculated using known methods for predicting melting temperatures (see, e.g., Baldino et al., Methods Enzymology 168:761-777; Bolton et al., 1962, Proc. Natl. Acad. Sci. USA 48:1390; Bresslauer et al., 1986, Proc. Natl. Acad. Sci USA 83:8893-8897; Freier et al., 1986, Proc. Natl. Acad. Sci USA 83:9373-9377; Kierzek et al., Biochemistry 25:7840-7846; Rychlik et al., 1990, Nucleic Acids Res 18:6409-6412 (erratum, 1991, Nucleic Acids Res 19:698); Sambrook et al., supra); Suggs et al., 1981, In Developmental Biology Using Purified Genes (Brown et al., eds.), pp. 683-693, Academic Press; and Wetmur, 1991, Crit Rev Biochem Mol Biol 26:227-259. All publications incorporate herein by reference). In some embodiments, the polynucleotide encodes the polypeptide disclosed herein and hybridizes under defined conditions, such as moderately stringent or highly stringent conditions, to the complement of a sequence encoding an engineered ketoreductase enzyme of the present disclosure.

"Hybridization stringency" relates to such washing conditions of nucleic acids. Generally, hybridization reactions are performed under conditions of lower stringency, followed by washes of varying but higher stringency. The term "moderately stringent hybridization" refers to conditions that permit target-DNA to bind a complementary nucleic acid that has about 60% identity, preferably about 75% identity, about 85% identity to the target DNA; with greater than about 90% identity to target-polynucleotide. Exemplary moderately stringent conditions are conditions equivalent to hybridization in 50% formamide, 5×Denhart's solution, 5×SSPE, 0.2% SDS at 42° C., followed by washing in 0.2×SSPE, 0.2% SDS, at 42° C. "High stringency hybridization" refers generally to conditions that are about 10° C. or less from the thermal melting temperature Tm as determined under the solution condition for a defined polynucleotide sequence. In some embodiments, a high stringency condition refers to conditions that permit hybridization of only those nucleic acid sequences that form stable hybrids in 0.018M NaCl at 65° C. (i.e., if a hybrid is not stable in 0.018M NaCl at 65° C., it will not be stable under high stringency conditions, as contemplated herein). High stringency conditions can be provided, for example, by hybridization in conditions equivalent to 50% formamide, 5×Denhart's solution, 5×SSPE, 0.2% SDS at 42° C., followed by washing in 0.1×SSPE, and 0.1% SDS at 65° C. Other high stringency hybridization conditions, as well as moderately stringent conditions, are described in the references cited above.

"Recombinant" when used with reference to, e.g., a cell, nucleic acid, or polypeptide, refers to a material, or a material corresponding to the natural or native form of the material, that has been modified in a manner that would not otherwise exist in nature, or is identical thereto but produced or derived from synthetic materials and/or by manipulation using recombinant techniques. Non-limiting examples include, among others, recombinant cells expressing genes that are not found within the native (non-recombinant) form of the cell or express native genes that are otherwise expressed at a different level.

"Heterologous" polynucleotide refers to any polynucleotide that is introduced into a host cell by laboratory techniques, and includes polynucleotides that are removed from a host cell, subjected to laboratory manipulation, and then reintroduced into a host cell.

"Codon optimized" refers to changes in the codons of the polynucleotide encoding a protein to those preferentially used in a particular organism such that the encoded protein is efficiently expressed in the organism of interest. Although the genetic code is degenerate in that most amino acids are represented by several codons, called "synonyms" or "synonymous" codons, it is well known that codon usage by particular organisms is nonrandom and biased towards particular codon triplets. This codon usage bias may be higher in reference to a given gene, genes of common function or ancestral origin, highly expressed proteins versus low copy number proteins, and the aggregate protein coding regions of an organism's genome. In some embodiments, the polynucleotides encoding the ketoreductases enzymes may be codon optimized for optimal production from the host organism selected for expression.

"Preferred, optimal, high codon usage bias codons" refers interchangeably to codons that are used at higher frequency in the protein coding regions than other codons that code for the same amino acid. The preferred codons may be determined in relation to codon usage in a single gene, a set of genes of common function or origin, highly expressed genes, the codon frequency in the aggregate protein coding regions of the whole organism, codon frequency in the aggregate protein coding regions of related organisms, or combinations thereof. Codons whose frequency increases with the level of gene expression are typically optimal codons for expression. A variety of methods are known for determining the codon frequency (e.g., codon usage, relative synonymous codon usage) and codon preference in specific organisms, including multivariat analysis, for example, using cluster analysis or correspondence analysis, and the effective number of codons used in a gene (see GCG CodonPreference, Genetics Computer Group Wisconsin Package; CodonW, John Peden, University of Nottingham; McInerney, J. O, 1998, Bioinformatics 14:372-73; Stenico et al., 1994, Nucleic Acids Res. 222437-46; Wright, F., 1990, Gene 87:23-29). Codon usage tables are available for a growing list of organisms (see for example, Wada et al., 1992, Nucleic Acids Res. 20:2111-2118; Nakamura et al., 2000, Nucl. Acids Res. 28:292; Duret, et al., supra; Henaut and Danchin, "*Escherichia coli* and *Salmonella,*" 1996, Neidhardt, et al. Eds., ASM Press, Washington D.C., p. 2047-2066. The data source for obtaining codon usage may rely on any available nucleotide sequence capable of coding for a protein. These data sets include nucleic acid sequences actually known to encode expressed proteins (e.g., complete protein coding sequences-CDS), expressed sequence tags (ESTS), or predicted coding regions of genomic sequences (see for example, Mount, D., Bioinformatics: Sequence and Genome Analysis, Chapter 8, Cold Spring Harbor Laboratory Press, Cold Spring Harbor, N.Y., 2001; Uberbacher, E. C., 1996, Methods Enzymol. 266:259-281; Tiwari et al., 1997, Comput. Appl. Biosci. 13:263-270).

"Control sequence" is defined herein to include all components, which are necessary or advantageous for the expression of a polypeptide of the present disclosure. Each control sequence may be native or foreign to the nucleic acid sequence encoding the polypeptide. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleic acid sequence encoding a polypeptide.

"Operably linked" is defined herein as a configuration in which a control sequence is appropriately placed at a position relative to the coding sequence of the DNA sequence such that the control sequence directs the expression of a polynucleotide and/or polypeptide.

"Promoter sequence" is a nucleic acid sequence that is recognized by a host cell for expression of the coding region. The control sequence may comprise an appropriate promoter sequence. The promoter sequence contains transcriptional control sequences, which mediate the expression of the polypeptide. The promoter may be any nucleic acid sequence which shows transcriptional activity in the host cell of choice including mutant, truncated, and hybrid promoters, and may be obtained from genes encoding extracellular or intracellular polypeptides either homologous or heterologous to the host cell.

"Cofactor regeneration system" refers to a set of reactants that participate in a reaction that reduces the oxidized form of the cofactor (e.g., NADP+ to NADPH). Cofactors oxidized by the ketoreductase-catalyzed reduction of the keto substrate are regenerated in reduced form by the cofactor regeneration system. Cofactor regeneration systems comprise a stoichiometric reductant that is a source of reducing hydrogen equivalents and is capable of reducing the oxidized form of the cofactor. The cofactor regeneration system may further comprise a catalyst, for example an enzyme catalyst, that catalyzes the reduction of the oxidized form of the cofactor by the reductant. Cofactor regeneration systems to regenerate NADH or NADPH from NAD+ or NADP+, respectively, are known in the art and may be used in the methods described herein.

5.2. Ketoreductase Polypeptides and Uses Thereof

The present disclosure provides engineered ketoreductase ("KRED") polypeptides that are enzymes capable of stereospecifically reducing N-protected (S)-3-amino-1-chloro-4-phenylbutan-2-one ("the substrate") (e.g. compound (1) where the protecting group is a BOC moiety) to the corresponding stereoisomeric alcohol product N-protected (2R, 3S)-3-amino-1-chloro-4-phenylbutan-2-ol ("the product") (e.g. compound (2)), as depicted in Scheme 1, above). In certain embodiments the substrate N-protected (S)-3-amino-1-chloro-4-phenylbutan-2-one ("the substrate") that is converted to the stereoisomeric alcohol product N-protected (2R, 3S)-3-amino-1-chloro-4-phenylbutan-2-ol product (e.g. compound (2)) is present within the biocatalytic reduction reaction as part of a racemic mixture, or as a substantially chirally pure compound, or as a chirally pure compound. The engineered ketoreductase ("KRED") enzymes of the present disclosure are those having an improved property when compared with a naturally-occurring, wild-type KRED enzyme obtained from *Novosphingobium aromaticivorans* (SEQ ID NO:2). Enzyme properties for which improvement is desirable include, but are not limited to, enzymatic activity, thermal stability, pH activity profile, cofactor requirements, refractoriness to inhibitors (e.g., product inhibition), sterospecificity, stereoselectivity, and solvent stability. The improvements can relate to a single enzyme property, such as enzymatic activity, or a combination of different enzyme properties, such as enzymatic activity and stereospecificity.

As noted above, the engineered ketoreductase with improved enzyme property is described with reference to *Novosphingobium aromaticivorans* (SEQ ID NO:2). The amino acid residue position is determined in these ketoreductases beginning from the initiating methionine (M) residue (i.e., M represents residue position 1), although it will be understood by the skilled artisan that this initiating methionine residue may be removed by biological processing machinery, such as in a host cell or in vitro translation system, to generate a mature protein lacking the initiating methionine residue. The amino acid residue position at which a particular amino acid or amino acid change is present in an amino acid sequence is sometimes describe herein in terms "Xn", or "residue n", where n refers to the residue position. A substitution mutation, which is a replacement of an amino acid residue in a residue corresponding to a residue of a reference sequence, for example the naturally occurring ketoreductase of SEQ ID NO:2, with a different amino acid residue is denoted as follows "X (number) Z," where X is the amino acid found in the wild type enzyme of *N. aromaticivorans* (SEQ ID NO:2) at position "number" and Z is the amino acid found at position "number" of the "mutant" enzyme, i.e. that in which amino acid Z has been substituted for amino acid X. In such instances, the single letter codes are used to represent the amino acid; e.g. G145A refers to an instance in which the "wild type" amino acid glycine at position 145 of SEQ ID NO: 2 has been replaced with the amino acid alanine.

Herein, mutations are sometimes described as a mutation of a residue "to a" type of amino acid. For example, SEQ ID NO: 2, residue 199 (isoleucine (I)) can be mutated "to a" polar residue. But the use of the phrase "to a" does not exclude mutations from one amino acid of a class to another amino acid of the same class. For example, residue 199 can be mutated from isoleucine "to an" asparagine.

A polynucleotide sequence encoding a naturally occurring ketoreductase of *Novosphingobium aromaticivorans* (also referred to as "ADH" or "alcohol dehydrogenase") can be obtained from the 780 bp region from base 160464 to 161243 complete sequence of *Novosphingobium aromaticivorans* DSM 12444 plasmid pNL2 (sequence) provided in GenBank accession no. CP000677.1. The corresponding polypeptide sequence encoded by this polynucleotide is provided by GenBank accession no. gi|145322460|gb|ABP64403.1| [145322460]. This polypeptide is four amino acids shorter than SEQ ID NO: 2 due to a different choice of initiation codon (i.e., the GenBank polypeptide sequence initiates with the Met corresponding to position 5 of SEQ ID NO: 2). The present disclosure is intended to include ketoreductase polypeptides wherein the polypeptide is a fragment of SEQ ID NO: 2, wherein the fragment amino acid sequence starts at the Met at position 5 of SEQ ID NO: 2 and ends at position 263 of SEQ ID NO: 2. Accordingly, in any of the embodiments of the engineered ketoreductase polypeptides disclosed herein, wherein the polypeptide comprises amino acid differences relative to SEQ ID NO: 2, the disclosure also provides a fragment of an engineered ketoreductase polypeptide, wherein the fragment amino acid sequence starts at the Met at position 5 of SEQ ID NO: 2 and ends at position 263 of SEQ ID NO: 2, and the amino acid differences are at the same amino acids as in the corresponding full-length engineered polypeptide relative to SEQ ID NO:2.

In some embodiments, the ketoreductase polypeptides herein can have a number of modifications relative to the reference sequence (*Novosphingobium aromaticivorans* of SEQ ID NO: 2) wherein the modifications result in an improved ketoreductase enzyme property. In such embodiments, the number of modifications to the amino acid sequence can comprise one or more amino acids, 2 or more amino acids, 3 or more amino acids, 4 or more amino acids, 5 or more amino acids, 6 or more amino acids, 8 or more amino acids, 9 or more amino acids, 10 or more amino acids, 15 or more amino acids, or 20 or more amino acids, up to 10% of the total number of amino acids, up to 10% of the total number of amino acids, up to 20% of the total number of amino acids, or up to 30% of the total number of amino acids of the reference enzyme sequence. In some embodiments, the number of modifications to the naturally occurring polypeptide or an engineered polypeptide that produces an improved ketoreductase property may comprise from about 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 modifications of the reference sequence. The modifications can comprise insertions, deletions, substitutions, or combinations thereof.

In some embodiments, the modifications comprise amino acid substitutions to the reference sequence, i.e., the *Novosphingobium aromaticivorans* KRED sequence of SEQ ID NO: 2. Substitutions that can produce an improved ketoreductase property may be at one or more amino acids, 2 or more amino acids, 3 or more amino acids, 4 or more amino acids, 5 or more amino acids, 6 or more amino acids, 7 or more amino acids, 8 or more amino acids, 9 or more amino acids, 10 or more amino acids, 15 or more amino acids, or 20 or more amino acids, up to 10% of the total number of amino acids, up to 15% of the total number of amino acids, up to 20% of the total number of amino acids, or up to 30% of the total number of amino acids of the reference enzyme sequence. In some embodiments, the number of substitutions to the naturally occurring polypeptide or an engineered polypeptide that produces an improved ketoreductase property can comprise from about 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 amino acid substitutions of the reference sequence.

In some embodiments, the improved property of the ketoreductase polypeptide is with respect to an increase of its stereospecificity. For example, in some embodiments, the improved property is the ability of the enzyme to differentiate the two enantiomers of N-protected 3-amino-1-chloro-4-phenylbutan-2-one (e.g., a racemic mixture of the (3S) and the (3R) enantiomers according to Formula (IV)), and convert substantially only the (3S) enantiomer to the corresponding stereoisomeric N-protected (2R,3S)-3-amino-1-chloro-4-phenylbutan-2-ol product of Formula (II) (e.g. compound (2)), as depicted, e.g. in Scheme 5, below.

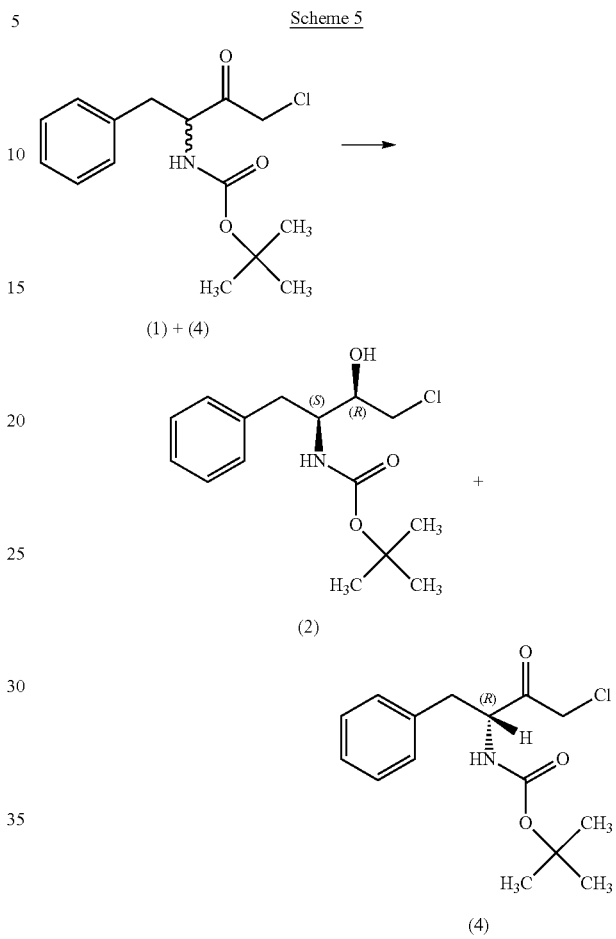

This improvement in stereospecificity of the ketoreductase polypeptide can be expressed as an improvement in the "E value" for the reaction with the ketoreductase.

In some embodiments, the improved property of the ketoreductase polypeptide is with respect to an increase in its ability to convert or reduce a greater percentage of the substrate to the product. In some embodiments, the improved property of the ketoreductase polypeptide is with respect to an increase in its rate of conversion of the substrate to the product. This improvement in enzymatic activity can be manifested by the ability to use less of the improved polypeptide as compared to the wild-type or other reference sequence(s) to reduce or convert the same amount of product. In some embodiments, the improved property of the ketoreductase polypeptide is with respect to its stability or thermostability. In some embodiments, the ketoreductase polypeptide has more than one improved property, such as a combination of stereospecificity, enzyme activity, and thermostability.

In some embodiments, the ketoreductase polypeptide is capable of stereospecifically converting the (3S)-enantiomer of N-protected 3-amino-1-chloro-4-phenylbutan-2-one to give the corresponding N-protected (2R,3S)-3-amino-1-chloro-4-phenylbutan-2-ol product with a percent diastereomeric excess of at least about 25%, 50%, 70%, 71%, 72%, 73%, 74%, 75%, 76%, 77%, 78%, 79%, 80%, 81%, 82%, 83%, 84%, 85%, 87%, 88%, 89%, 90%, 91%, 92%, 93%, 94%, 95%, 96%, 97%, 98%, 99%, 99.9%, or 99.99%.

In some embodiments, the ketoreductase polypeptide is capable of stereospecifically converting the substrate to the product in greater than about 90% diastereomeric excess. Exemplary polypeptides with such stereospecificity include, but are not limited to, the polypeptides comprising the amino acid sequences corresponding to SEQ ID NO:4, 6, 8, 10, 12, 14, 16, 18, 20, 22, 24, 26, 28, 30, 32, 34, 36, 38, 40, 42, 44, 46, 48, 50, 52, 54, 56, and 58.

In some embodiments, the ketoreductase polypeptide is capable of stereospecifically converting the substrate to the product in greater than about 95% diastereomeric excess. Exemplary polypeptides with such stereospecificity include, but are not limited to, the polypeptides comprising the amino acid sequences corresponding to SEQ ID NO:4, 6, 8, 10, 12, 14, 16, 18, 20, 22, 24, 26, 28, 30, 32, 34, 36, 38, 40, 42, 44, 46, 48, 50, 52, 54, 56, and 58.

In some embodiments, the ketoreductase polypeptide is capable of stereospecifically converting the substrate to the product in greater than about 97% diastereomeric excess. Exemplary polypeptides with such stereospecificity include, but are not limited to, the polypeptides comprising the amino acid sequences corresponding to SEQ ID NO:4, 6, 8, 10, 12, 14, 16, 18, 20, 22, 24, 26, 28, 30, 32, 34, 36, 38, 40, 42, 44, 46, 48, 50, 52, 54, 56, and 58.

In some embodiments, the ketoreductase polypeptide is capable of stereospecifically converting the substrate to the product in greater than about 98% diastereomeric excess. Exemplary ketoreductase polypeptides with such high stereospecificity include, but are not limited to, the polypeptides comprising the amino acid sequences corresponding to SEQ ID NO: 4, 6, 8, 10, 12, 14, 16, 18, 20, 22, 24, 26, 28, 30, 32, 34, 36, 38, 40, 42, 44, 46, 48, 50, 52, 54, 56, and 58.

In some embodiments, the ketoreductase polypeptide is capable of stereospecifically converting the substrate to the product with a percent diastereomeric excess that is at least about 98%, 99%, 99.9%, or 99.99%, where the polypeptide comprises an amino acid sequence corresponding to: SEQ ID NO: 4, 6, 8, 10, 12, 14, 16, 18, 20, 22, 24, 26, 28, 30, 32, 34, 36, 38, 40, 42, 44, 46, 48, 50, 52, 54, 56, and 58.

In some embodiments, the ketoreductase polypeptides are equivalent to or improved as compared to wild-type (SEQ ID NO:2) with respect to their rate of enzymatic activity, i.e., their rate or ability of converting the substrate to the product. Exemplary polypeptides that are capable of converting the substrate to the product at a conversion rate that is equivalent to or improved over wild-type, include but are not limited to, polypeptides that comprise the amino acid sequences corresponding to SEQ ID NO:4, 6, 8, 10, 12, 14, 16, 18, 20, 22, 24, 26, 28, 30, 32, 34, 36, 38, 40, 42, 44, 46, 48, 50, 52, 54, 56, and 58.

In some embodiments, the ketoreductase polypeptides are improved as compared to wild-type (SEQ ID NO:2) with respect to their rate of enzymatic activity, i.e., their rate or ability of converting the substrate to the product. Exemplary polypeptides that are capable of converting the substrate to the product at a conversion rate that is at least about 1.2-fold improved over wild-type, include but are not limited to, polypeptides that comprise the amino acid sequences corresponding to SEQ ID NO:4, 6, 14, 16, 18, 22, 24, 26, 28, 30, 32, 34, 36, 38, 40, 50, 52, 54, and 56.

In some embodiments, the ketoreductase polypeptides are improved as compared to wild-type (SEQ ID NO:2) with respect to their rate of enzymatic activity, i.e., their rate or ability of converting the substrate to the product. Exemplary polypeptides that are capable of converting the substrate to the product at a conversion rate that is at least about 1.5-fold improved over wild-type, include but are not limited to, polypeptides that comprise the amino acid sequences corresponding to SEQ ID NO: 6, 18, 22, 30, 38, 40, 50, 52, 54, and 56.

In some embodiments, the ketoreductase polypeptides are improved as compared to wild-type (SEQ ID NO:2) with respect to their rate of enzymatic activity, i.e., their rate or ability of converting the substrate to the product. Exemplary polypeptides that are capable of converting the substrate to the product at a conversion rate that is at least about 3-fold improved over wild-type, include but are not limited to, polypeptides that comprise the amino acid sequences corresponding to SEQ ID NO:6, 50, 52, and 56.

In some embodiments, the engineered ketoreductase polypeptides of the disclosure are capable of converting the substrate to product with a diastereomeric excess of at least about 90%, 91%, 92%, 93%, 94%, 95%, 96%, 97%, 98%, 99%, 99.9%, 99.99%, or more. Exemplary engineered ketoreductase polypeptides that have this capability include, but are not limited to, polypeptides comprising the sequence that corresponds to SEQ ID NO: 4, 6, 8, 10, 12, 14, 16, 18, 20, 22, 24, 26, 28, 30, 32, 34, 36, 38, 40, 42, 44, 46, 48, 50, 52, 54, 56 and 58.

In some embodiments, the engineered ketoreductase polypeptides of the disclosure are capable of improved conversion rates for reducing a substrate compound of Formula (I) (e.g., compound (1)) to a product compound of Formula (II) (e.g., compound (2)). For example, in some embodiments, the engineered ketoreductase polypeptides of the disclosure are capable of converting at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more of the substrate to the product in about 24 hours or less. In some embodiments, the engineered ketoreductase polypeptides are capable of converting at least about 90% of the substrate to the product in less than about 24 hours, less than about 20 hours, less than about 16 hours, less than about 12 hours, and even less than about 10 hours. Exemplary engineered ketoreductase polypeptides that have this capability include, but are not limited to, polypeptides comprising the sequence that corresponds to SEQ ID NO: 6, 50, 52, and 56.

In some embodiments, the engineered ketoreductase polypeptides of the disclosure are capable of converting at least about 70%, 80%, 90%, 95%, 99% or more of a substrate of compound of Formula (I) (e.g., compound (1)) to a product compound of Formula (II) (e.g., compound (2)) in about 24 hours or less when the reaction mixture comprises about 1% or less (but more than 0%), 0.5% or less (but more than 0%), 0.2% or less (but more than 0%), or even 0.1% or less (but more than 0%) of the ketoreductase polypeptide by weight with respect to the weight of the amount of substrate. Exemplary polypeptides that have this capability include, but are not limited to, polypeptides comprising the sequence that corresponds to SEQ ID NO: 6, 50, 52, and 56.

In some embodiments, the engineered ketoreductase polypeptides of the disclosure are capable of converting at least about 70%, 80%, 90%, 95%, 99% or more of a substrate of compound of Formula (I) (e.g., compound (1)) to a product compound of Formula (II) (e.g., compound (2)) in about 24 hours or less when the reaction mixture comprises a ketoreductase polypeptide loading of about 10 g/L or less, 5 g/L or less, 2 g/L or less, 1 g/L or less and an initial concentration of substrate in the reaction mixture (i.e., substrate loading) of at least about 25 g/L, at least about 50 g/L, at least about 75 g/L, at least about 100 g/L, at least about 125 g/L, at least about 150 g/L, at least about 175 g/L, or at least about 200 g/L. Exemplary polypeptides that have this capability include, but are not limited to, polypeptides comprising the sequence that corresponds to SEQ ID NO: 6, 50, 52, and 56.

In some embodiments, the ketoreductase polypeptides have improved activity and stability over wild-type, and can reduce the substrate to the product in greater than about 98% d.e. Exemplary polypeptides with such capabilities include, but are not limited to SEQ ID NO: 4, 6, 14, 16, 18, 22, 24, 26, 28, 30, 32, 34, 36, 38, 40, 50, 52, 54, and 56. Table 2 below lists engineered ketoreductase polypeptides (and encoding polynucleotides) by sequence identifier (SEQ ID NO) disclosed herein together with the specific residue differences of the variant sequences of the engineered polypeptides relative to the wild-type *Novosphingobium aromaticivorans* ketoreductase sequences (SEQ ID NO:2) from which they were derived by directed evolution (see e.g., Stemmer et al., 1994, *Proc Natl Acad Sci USA* 91:10747-10751). Each row of Table 2 lists two SEQ ID NOs, where the odd number refers to the nucleotide sequence that encodes for the polypeptide amino acid sequence provided by the even number.

The activity of each engineered ketoreductase polypeptide was determined relative to the activity wild-type enzyme of SEQ ID NO: 2 (wild-type: ~30% conversion in 24 hours, 3 g/L substrate loading, 5 g/L enzyme loading). Activity was determined as conversion of compound (1) to compound (2) monitored over time, as described in Example 7. As summarized in Table 2, the improvement in activity was quantified as follows: "Control" indicates 100% to 120% as compared to the activity of KRED of SEQ ID NO:2; "+" indicates >120% to 150% as compared to the KRED of SEQ ID NO:2; "++" indicates >150% to 300% as compared to the KRED of SEQ ID NO:2; and "+++" indicates >300% as compared to the KRED of SEQ ID NO:2.

TABLE 2

| SEQ ID NO: (nt/aa) | Residue Difference(s) (relative to SEQ ID NO: 2) | Improvement in Activity |
|---|---|---|
| 3/4 | G145A; | + |
| 5/6 | G145A; I199L; | +++ |
| 7/8 | S90V; A232V | Control |
| 9/10 | F152L | Control |
| 11/12 | A34S | Control |
| 13/14 | A47V; I199M | + |
| 15/16 | I199L | + |
| 17/18 | N153G | ++ |
| 19/20 | N153V | Control |
| 21/22 | N153H | ++ |
| 23/24 | A150G | + |
| 25/26 | I91L | + |
| 27/28 | I91W | + |
| 29/30 | I91R | ++ |
| 31/32 | I91K | + |
| 33/34 | V144T | + |
| 35/36 | A150G; P231F | + |
| 37/38 | G190A | ++ |
| 39/40 | F260Y | ++ |
| 41/42 | S198N | Control |
| 43/44 | D81N; M200I | Control |
| 45/46 | G145A; S261N | Control |
| 47/48 | V28A; D112Y; G117D; S143R; G145A; R148H; E233Q; S261N | Control |
| 49/50 | P2L; E50K; G145A; A217T | +++ |
| 51/52 | G145A | +++ |
| 53/54 | K94R; G145A; I199N | ++ |
| 55/56 | G145A; I225V | +++ |
| 57/58 | G145A; T158S; D244G | Control |

The improved activity of the engineered ketoreductase polypeptides for the conversion of the secondary alcohol, isopropanol (IPA) to its corresponding product, acetone was determined relative to the same activity for the reference polypeptide of SEQ ID NO: 2. Relative IPA activity was determined using an assay with the following reaction conditions: 100 µl 10× diluted engineered KRED lysate, 10% IPA (v/v), 0.5 g/L NAD$^+$, 100 mM TEA, pH 7.5. Exemplary engineered ketoreductase polypeptides exhibiting at least 2-fold increased activity with IPA relative to SEQ ID NO: 2 are listed in Table 3. The fold-improvement in IPA activity relative the WT of SEQ ID NO: 2 was quantified as follows: "+" indicates at least 200% to 250% improvement; "++" indicates <250% to 500% improvement; and "+++" indicates >500% to 1000% improvement; and "++++" indicates >1000% to 2000% improvement.

TABLE 3

| SEQ ID NO: | Residue Differences (relative to SEQ ID NO: 2) | FIOP in IPA activity |
|---|---|---|
| 6 | G145A, I199L | ++ |
| 56 | G145A, I225V | ++ |
| 60 | G145V | + |
| 62 | I199G | ++ |
| 64 | V144C | ++ |
| 66 | A150S | ++ |
| 68 | A150I | ++ |
| 70 | A150W | +++ |
| 72 | G190P | ++ |
| 74 | G190Q | + |
| 76 | G190V | ++++ |
| 78 | V204F | ++ |
| 80 | M200I | +++ |

In some embodiments, the present disclosure provides an improved ketoreductase polypeptide comprising an amino acid sequence that is at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO:2 and comprising at least one amino acid substitution listed in Table 2 or Table 3.

In some embodiments, the present disclosure provides an improved ketoreductase polypeptide capable of exhibiting a relative activity at least about 3-fold that of a polypeptide of SEQ ID NO: 2 (i.e., "+++" based on relative activity designations of Table 2 above), wherein the improved ketoreductase polypeptide comprises an amino acid sequence that is at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO:2 and comprises at least one of the following amino acid substitutions or sets of amino acid substitutions: G145A; G145A and I225V; P2L, E50K, G145A, and A217T; G145A, and I199L. Such improved ketoreductase polypeptides disclosed herein may further comprise additional modifications, including substitutions, deletions, insertions, or combinations thereof. The substitutions can be non-conservative substitutions, conservative substitutions, or a combination of non-conservative and conservative substitutions. Other useful amino acid sequence substitutions for improved ketoreductases at positions P2, E50, G145, I199, A217, and I225, are disclosed below. In some embodiments, these ketoreductase polypeptides can have optionally from about 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 mutations at other amino acid residues. In some embodiments, the number of modifications can be 1, 2, 3, 4, 5, 6, 7, 8, 9, 10, 11, 12, 14, 15, 16, 18, 20, 22, 24, 26, 30, 35 or about 40 other amino acid residues.

In some embodiments, the present disclosure provides an improved ketoreductase polypeptide capable of exhibiting a relative activity at least about 1.5-fold that of a polypeptide of SEQ ID NO: 2 (i.e., "++" based on relative activity designations of Table 2 above), wherein the improved ketoreductase polypeptide comprises an amino acid sequence that is at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO:2 and comprises at least one of the following amino acid substitutions as compared to SEQ ID NO:2: N153G; N153H; G190A; F260Y; I91R; K94R; G145A; I199N; or the following set of amino acid substitutions as compared to SEQ ID NO:2: K94R, G145A, and I199N. Such improved ketoreductase polypeptides disclosed herein may further comprise additional modifications, including substitutions, deletions, insertions, or combinations thereof. The substitutions can be non-conservative substitutions, conservative substitutions, or a combination of non-conservative and conservative substitutions. Other useful amino acid sequence substitutions for improved ketoreductases at positions I91, K94, G145, N153, G190, I199, and F260, are disclosed below. In some embodiments, these ketoreductase polypeptides can have optionally from about 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 mutations at other amino acid residues. In some embodiments, the number of modifications can be 1, 2, 3, 4, 5, 6, 7, 8, 9, 10, 11, 12, 14, 15, 16, 18, 20, 22, 24, 26, 30, 35 or about 40 other amino acid residues.

In some embodiments, the present disclosure provides an improved ketoreductase polypeptide capable of exhibiting a relative activity at least about 1.2-fold that of a polypeptide of SEQ ID NO: 2 (i.e., "+" based on relative activity designations of Table 2 above), wherein the improved ketoreductase polypeptide comprises an amino acid sequence that is at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO:2 and comprises at least one of the following amino acid substitutions as compared to SEQ ID NO:2: I199L; A150G; I91L; I91W; I91K; and V144T; or one of the following sets of amino acid substitutions as compared to SEQ ID NO:2: G145A; A47V and I199M; A150G and P231F. Such improved ketoreductase polypeptides disclosed herein may further comprise additional modifications, including substitutions, deletions, insertions, or combinations thereof. The substitutions can be non-conservative substitutions, conservative substitutions, or a combination of non-conservative and conservative substitutions. Other useful amino acid sequence substitutions for improved ketoreductases at positions A47, I91, V144, G145, A150, I199, and P231, are disclosed below. In some embodiments, these ketoreductase polypeptides can have optionally from about 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 mutations at other amino acid residues. In some embodiments, the number of modifications can be 1, 2, 3, 4, 5, 6, 7, 8, 9, 10, 11, 12, 14, 15, 16, 18, 20, 22, 24, 26, 30, 35 or about 40 other amino acid residues.

In some embodiments, the present disclosure provides an improved ketoreductase polypeptide capable of exhibiting a relative activity in converting isopropanol to acetone of at least about 2-fold that of a polypeptide of SEQ ID NO: 2 (i.e., "+" based on relative activity designations of Table 3 above), wherein the improved ketoreductase polypeptide comprises an amino acid sequence that is at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO:2 and comprises at least one of the following amino acid substitutions as compared to SEQ ID NO:2: V144C, G145A, G145V, A150S, A150I, A150W, G190P, G190Q, G190V, I199G, I199L, M200I, V204F, or I225V; or one of the following sets of amino acid substitutions as compared to SEQ ID NO:2: G145A, I199L; or G145A, I225V. Such improved ketoreductase polypeptides disclosed herein may further comprise additional modifications, including substitutions, deletions, insertions, or combinations thereof. The substitutions can be non-conservative substitutions, conservative substitutions, or a combination of non-conservative and conservative substitutions. Other useful amino acid sequence substitutions for improved ketoreductases at positions V144, G145, A150, G190, I199, M200, V204, and I225, are disclosed below. In some embodiments, these ketoreductase polypeptides can have optionally from about 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 mutations at other amino acid residues. In some embodiments, the number of modifications can be 1, 2, 3, 4, 5, 6, 7, 8, 9, 10, 11, 12, 14, 15, 16, 18, 20, 22, 24, 26, 30, 35 or about 40 other amino acid residues.

Accordingly, in some embodiments the present disclosure provides an engineered ketoreductase polypeptide capable of oxidizing isopropanol (IPA) to acetone with an activity at least 2-fold, 2.5-fold, 5-fold, or 10-fold greater than the reference polypeptide of SEQ ID NO: 2, wherein the polypeptide comprises an amino acid sequence having at least 70%, 80%, 85%, 90%, 95%, 98%, 99% or greater identity to a sequence selected from SEQ ID NO: 6, 56, 60, 62, 64, 66, 68, 70, 72, 74, 76, 78, and 80. In some embodiments, the engineered polypeptide has an amino acid sequence that has at least 95% identity to a sequence selected from SEQ ID NO: 6, 56, 60, 62, 64, 66, 68, 70, 72, 74, 76, 78, and 80. In some embodiments, the engineered polypeptide has an amino acid sequence selected from SEQ ID NO: 6, 56, 60, 62, 64, 66, 68, 70, 72, 74, 76, 78, and 80.

In some embodiments, the engineered ketoreductase polypeptide capable of oxidizing isopropanol (IPA) to acetone with an activity at least 2-fold, 2.5-fold, 5-fold, or 10-fold greater than the reference polypeptide of SEQ ID NO: 2, has an amino acid sequence comprises at least one of the following features: residue corresponding to amino acid 144 of SEQ ID NO:2 is cysteine; residue corresponding to amino acid 145 of SEQ ID NO:2 is selected from the group consisting of alanine, and valine; residue corresponding to amino acid 150 of SEQ ID NO:2 is selected from the group consisting of isoleucine, serine, and tryptophan; residue corresponding to amino acid 190 of SEQ ID NO:2 is selected from the group consisting of glutamine, proline, and valine; residue corresponding to amino acid 199 of SEQ ID NO:2 is selected from the group consisting of glycine, and leucine; residue corresponding to amino acid 200 of SEQ ID NO:2 is isoleucine; residue corresponding to amino acid 204 of SEQ ID NO:2 is phenylalanine; and residue corresponding to amino acid 225 of SEQ ID NO:2 is valine. In certain embodiments, the amino acid sequence of the engineered polypeptide comprises at least one of the following substitutions as compared to SEQ ID NO:2: V144C, A150I, A150S, A150W, G190P, G190V, M200I, and V204F. In certain embodiments, the amino acid sequence of the engineered polypeptide comprises at least one of the following sets of amino acid substitutions as compared to SEQ ID NO:2: G145A, and I199L; and G145A, and I225V.

In some embodiments, the engineered ketoreductase polypeptide is capable of oxidizing isopropanol (IPA) to acetone with an activity at least 5-fold greater than the reference polypeptide of SEQ ID NO: 2, and wherein the amino acid sequence comprises at least one of the following substitutions as compared to SEQ ID NO:2: A150W, M200I, and G190V.

In some embodiments, the ketoreductase polypeptides of the present disclosure can have one or more modifications (i.e., residue differences) as compared to the reference amino acid sequence or as compared to any of SEQ ID NO: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, or 80. The modifications can include substitutions, deletions, insertions, or combinations thereof. The substitutions can be non-conservative substitutions, conservative substitutions, or a combination of non-conservative and conservative substitutions. In some embodiments, these ketoreductase polypeptides can have optionally from about 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 mutations at other amino acid residues. In some embodiments, the number of modifications can be 1, 2, 3, 4, 5, 6, 7, 8, 9, 10, 11, 12, 14, 15, 16, 18, 20, 22, 24, 26, 30, 35 or about 40 other amino acid residues.

In some embodiments the present disclosure provides an improved ketoreductase polypeptide comprising an amino acid sequence that is at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO:2, and comprise at least one amino acid substitution as compared to SEQ ID NO: 2 selected from the group consisting of: the proline residue at position 2 is replaced with an aliphatic or nonpolar amino acid selected from among alanine, leucine, valine, isoleucine, glycine and methionine; the valine residue at position 28, in a conservative change, is replaced with an aliphatic or nonpolar amino acid selected from among alanine, leucine, valine, isoleucine, glycine and methionine; the alanine residue at position 34 is replaced with a polar amino acid selected from among asparagine, glutamine, serine, and threonine; the alanine residue at position 47, in a conservative change, is replaced with an aliphatic or nonpolar amino acid selected from among alanine, leucine, valine, isoleucine, glycine and methionine; the glutamic acid residue at position 50 is replaced with a basic amino acid selected from lysine and arginine; the aspartic acid residue at position 81 is replaced with a polar amino acid selected from among asparagine, glutamine, serine, and threonine; the serine residue at position 90 is replaced with an aliphatic or nonpolar amino acid selected from among alanine, leucine, valine, isoleucine, glycine and methionine; the isoleucine residue at position 91 is, in a conservative change, replaced with an aliphatic or nonpolar amino acid selected from among alanine, leucine, valine, isoleucine, glycine and methionine, while in other aspects, the isoleucine residue at position 91 is replaced with an aromatic amino acid selected from among tyrosine, tryptophan, and phenylalanine, or a basic amino acid selected from among lysine and arginine; the lysine residue at position 94 is, in a conservative change, replaced with another basic amino acid, arginine; the aspartic acid residue at position 112 is replaced with an aromatic amino acid selected from among tyrosine, tryptophan, and phenylalanine; the glycine residue at position 117 is replaced with an acidic amino acid selected from among aspartic acid and glutamic acid; the serine residue at position 143 is replaced with a basic amino acid selected from among lysine and arginine; the valine residue at position 144 is replaced with a cysteine or a polar amino acid selected from among asparagine, glutamine, serine, and threonine; the glycine residue at position 145, in either a conservative or non-conservative change, may be replaced with a nonpolar amino acid selected from among alanine, leucine, valine, isoleucine, and methionine or an aliphatic amino acid selected from among alanine, leucine, valine, isoleucine; the arginine residue at position 148 is replaced with a constrained amino acid selected from among proline and histidine; the alanine residue at position 150, in conservative or non-conservative change, is replaced with another nonpolar or aliphatic amino acid selected from among leucine, valine, isoleucine, glycine and methionine, or a polar amino acid selected from among asparagine, glutamine, serine, and threonine, or an aromatic amino acid selected from among tyrosine, tryptophan, and phenylalanine; the phenylalanine residue at position 152 is replaced with a nonpolar or aliphatic amino acid selected from among alanine, leucine, valine, isoleucine, glycine and methionine; the asparagine residue at position 153 is replaced with a nonpolar or aliphatic amino acid selected from among alanine, leucine, valine, isoleucine, glycine and methionine, or with a constrained amino acid selected from among histidine and proline; the threonine residue at position 158, in a conservative change, is replaced with another polar amino acid selected from among asparagine, glutamine, and serine; the glycine residue at position 190, in either a conservative or a nonconservative change, is replaced with either a nonpolar or an aliphatic amino acid selected from among alanine, valine, leucine, isoleucine, glycine, and methionine, or a polar amino acid selected from among asparagine, glutamine, and serine, or a proline; the serine residue at position 198, in a conservative change, is replaced with another polar amino acid selected from among asparagine, glutamine, and threonine; the isoleucine residue at position 199 is, in a conservative change replaced with another aliphatic or nonpolar amino acid selected from among alanine, leucine, valine, glycine, and methionine, or with a polar amino acid selected from among asparagine, glutamine, serine, and threonine; the methionine residue at position 200, in a conservative change, is replaced with another nonpolar amino acid selected from among alanine, leucine, valine, isoleucine, and glycine; the valine at position 204, in a non-conservative change, is replaced with an aromatic amino acid selected from among tyrosine, tryptophan, and phenylalanine; the alanine residue at position 217 is replaced with a polar amino acid selected from among asparagine, glutamine, serine and threonine; the isoleucine residue at position 225, in a conservative change, is replaced with another nonpolar amino acid selected from among valine, leucine, glycine, and methionine; the proline residue at position 231 is replaced with an aromatic amino acid selected from among tyrosine, tryptophan, and phenylalanine; the alanine residue at position 232, in a conservative change, is replaced with another nonpolar amino acid selected from among leucine, isoleucine, valine, glycine, and methionine; the glutamic acid residue at position 233 is replaced with a polar amino acid selected from among asparagine, glutamine, serine, and threonine; the aspartic acid residue at position 244 is replaced with a nonpolar amino acid selected from among alanine, leucine, isoleucine, valine, glycine, and methionine; the phenylalanine residue at position 260, in a conservative change, is replaced with another aromatic amino acid selected from among tyrosine and tryptophan; and the serine residue at position 261, in a conservative change, is replaced with another polar amino acid selected from among asparagine, glutamine, and threonine. The forgoing improved ketoreductase polypeptides may further comprise additional modifications, including substitutions, deletions, insertions, or combinations thereof. The substitutions can be non-conservative substitutions, conservative substitutions, or a combination of non-conservative and conservative substitutions. In some embodiments, these ketoreductase polypeptides can have optionally from about 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 mutations at other amino acid residues. In some embodiments, the number of modifications can be 1, 2, 3, 4, 5, 6, 7, 8, 9, 10, 11, 12, 14, 15, 16, 18, 20, 22, 24, 26, 30, 35 or about 40 other amino acid residues.

In certain embodiments, the improved ketoreductase polypeptides of the present disclosure comprise an amino acid sequence that is at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO:2, and comprise, as compared to SEQ ID NO:2, at least one amino acid substitution selected from the group consisting of: the proline residue at position 2 is replaced with leucine (P2L); the valine residue at position 28 is replaced with alanine (V28A); the alanine residue at position 34 is replaced with serine (A34S); the alanine residue at position 47 is replaced with valine (A47V); the glutamic acid residue at position 50 is replaced with lysine (E50K); the aspartic acid residue at position 81 is replaced with asparagine (D81N); the serine residue at position 90 is replaced with valine (S90V); the isoleucine residue at position 91 is replaced with an amino acid selected from among leucine (I91L), tryptophan (I91W), arginine (I91R), and lysine (I91K); the lysine residue at position 94 is replaced with arginine (K94R); the aspartic acid residue at position 112 is replaced with tyrosine (D112Y); the glycine residue at position 117 is replaced with aspartic acid (G117D); the serine residue at position 143 is replaced with arginine (S143R); the valine residue at position 144 is replaced with an amino acid selected from among cysteine (V144C) and threonine (V144T); the glycine residue at position 145 is replaced with an amino acid selected from among alanine (G145A) and valine (G145V); the arginine residue at position 148 is replaced with histidine (R148H); the alanine residue at position 150 is replaced with an amino acid selected from among glycine (A150G), isoleucine (A150I), serine (A150S), and tryptophan (A150W); the phenylalanine residue at position 152 is replaced with leucine (F152L); the asparagine residue at position 153 is replaced with an amino acid selected from among glycine (N153G), valine (N153V), and histidine (N153H); the threonine residue at position 158 is replaced with serine (T158S); the glycine residue at position 190 is replaced with an amino acid selected from among alanine (G190A), proline (G190P), glutamine (G190Q), and valine (G190V); the serine residue at position 198 is replaced with asparagine (S198N); the isoleucine residue at position 199 is replaced with an amino acid selected from among glycine (I199G), methionine (I199M), leucine (I199L), and asparagine (I199N); the methionine residue at position 200 is replaced with isoleucine (M200I); the valine residue at position 204 is replaced with phenylalanine (V204F); the alanine residue at position 217 is replaced with threonine (A217T); the isoleucine residue at position 225 is replaced with valine (I225V); the proline residue at position 231 is replaced with phenylalanine (P231F); the alanine residue at position 232 is replaced with valine (A232V); the glutamic acid residue at position 233 is replaced with glutamine (E233Q); the aspartic acid residue at position 244 is replaced with glycine (D244G); the phenylalanine residue at position 260 is replaced with tyrosine (F260Y); and the serine residue at position 261 is replaced with asparagine (S261N).

In certain embodiments, an engineered ketoreductase polypeptide of the present disclosure comprises an amino acid sequence selected from the group consisting of SEQ ID NO: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, and 80. The foregoing improved ketoreductase polypeptides may further comprise additional modifications, including substitutions, deletions, insertions, or combinations thereof. The substitutions can be non-conservative substitutions, conservative substitutions, or a combination of non-conservative and conservative substitutions. In some embodiments, these ketoreductase polypeptides can have optionally from about 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 mutations at other amino acid residues. In some embodiments, the number of modifications can be 1, 2, 3, 4, 5, 6, 7, 8, 9, 10, 11, 12, 14, 15, 16, 18, 20, 22, 24, 26, 30, 35 or about 40 other amino acid residues.

In some embodiments, the improved engineered ketoreductase enzymes can comprise deletions of the naturally occurring ketoreductase polypeptides as well as deletions of other improved ketoreductase polypeptides. In some embodiments, each of the improved engineered ketoreductase enzymes described herein can comprise deletions of the polypeptides described herein. Thus, for each and every embodiment of the ketoreductase polypeptides of the disclosure, the deletions can comprise one or more amino acids, 2 or more amino acids, 3 or more amino acids, 4 or more amino acids, 5 or more amino acids, 6 or more amino acids, 8 or more amino acids, 10 or more amino acids, 15 or more amino acids, or 20 or more amino acids, up to 10% of the total number of amino acids, up to 10% of the total number of amino acids, up to 20% of the total number of amino acids, or up to 30% of the total number of amino acids of the ketoreductase polypeptides, as long as the functional activity of the ketoreductase activity is maintained. In some embodiments, the deletions can comprise, 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 amino acid residues.

As described herein, the ketoreductase polypeptides of the disclosure can be in the form of fusion polypeptides in which the ketoreductases polypeptides are fused to other polypeptides, such as antibody tags (e.g., myc epitope) or purifications sequences (e.g., His tags). Thus, the ketoreductase polypeptides can be used with or without fusions to other polypeptides.

In some embodiments, the improved engineered ketoreductase enzymes can comprise additions or insertions of amino acid sequences the naturally occurring ketoreductase polypeptides as well as additions to or insertions of amino acid sequences to other improved ketoreductase polypeptides. In particular embodiments, a ketoreductases polypeptide of the present disclosure may, for example, comprise 1-20, 2-15, 3-10, 4-8, or 5-7 additional amino acid at the amino- or carboxy-terminus of the naturally occurring ketoreductase polypeptides, as well as to improved ketoreductase polypeptides of the disclosure. For each and every embodiment of the ketoreductase polypeptides of the disclosure, the insertions or additions can comprise one or more amino acids, 2 or more amino acids, 3 or more amino acids, 4 or more amino acids, 5 or more amino acids, 6 or more amino acids, 8 or more amino acids, 10 or more amino acids, 15 or more amino acids, or 20 or more amino acids, up to 10% of the total number of amino acids, up to 10% of the total number of amino acids, up to 20% of the total number of amino acids, or up to 30% of the total number of amino acids of the ketoreductase polypeptides, as long as the functional activity of the ketoreductase activity is maintained. In some embodiments, the insertions or additions can comprise, 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 amino acid residues.

The polypeptides described herein are not restricted to the genetically encoded amino acids. In addition to the genetically encoded amino acids, the polypeptides described herein may be comprised, either in whole or in part, of naturally-occurring and/or synthetic non-encoded amino acids. Certain commonly encountered non-encoded amino acids of which the polypeptides described herein may be comprised include, but are not limited to: the D-enantiomers of the genetically-encoded amino acids; 2,3-diaminopropionic acid (Dpr); α-aminoisobutyric acid (Aib); ε-aminohexanoic acid (Aha); 6-aminovaleric acid (Ava); N-methylglycine or sarcosine (MeGly or Sar); ornithine (Orn); citrulline (Cit); t-butylalanine (Bua); t-butylglycine (Bug); N-methylisoleucine (MeIle); phenylglycine (Phg); cyclohexylalanine (Cha); norleucine (Nle); naphthylalanine (Nal); 2-chlorophenylalanine (Ocf); 3-chlorophenylalanine (Mcf); 4 chlorophenylalanine (Pcf); 2 fluorophenylalanine (Off); 3 fluorophenylalanine (Mff); 4 fluorophenylalanine (Pff); 2-bromophenylalanine (Obf); 3-bromophenylalanine (Mbf); 4-bromophenylalanine (Pbf); 2-methylphenylalanine (Omf); 3-methylphenylalanine (Mmf); 4-methylphenylalanine (Pmf); 2-nitrophenylalanine (Onf); 3-nitrophenylalanine (Mnf); 4-nitrophenylalanine (Pnf); 2-cyanophenylalanine (Ocf); 3-cyanophenylalanine (Mcf); 4-cyanophenylalanine (Pcf); 2-trifluoromethylphenylalanine (Otf); 3-trifluoromethylphenylalanine (Mtf); 4-trifluoromethylphenylalanine (Ptf); 4-aminophenylalanine (Paf); 4-iodophenylalanine (Pif); 4-aminomethylphenylalanine (Pamf); 2,4-dichlorophenylalanine (Opef); 3,4-dichlorophenylalanine (Mpcf); 2,4-difluorophenylalanine (Opff); 3,4-difluorophenylalanine (Mpff); pyrid-2-ylalanine (2pAla); pyrid-3-ylalanine (3pAla); pyrid-4-ylalanine (4pAla); naphth-1-ylalanine (1nAla); naphth-2-ylalanine (2nAla); thiazolylalanine (taAla); benzothienylalanine (bAla); thienylalanine (tAla); furylalanine (fAla); homophenylalanine (hPhe); homotyrosine (hTyr); homotryptophan (hTrp); pentafluorophenylalanine (5ff); styrylkalanine (sAla); authrylalanine (aAla); 3,3-diphenylalanine (Dfa); 3-amino-5-phenypentanoic acid (Afp); penicillamine (Pen); 1,2,3,4-tetrahydroisoquinoline-3-carboxylic acid (Tic); β-2-thienylalanine (Thi); methionine sulfoxide (Mso); N(w)-nitroarginine (nArg); homolysine (hLys); phosphonomethylphenylalanine (pmPhe); phosphoserine (pSer); phosphothreonine (pThr); homoaspartic acid (hAsp); homoglutanic acid (hGlu); 1-aminocyclopent-(2 or 3)-ene-4 carboxylic acid; pipecolic acid (PA), azetidine-3-carboxylic acid (ACA); 1-aminocyclopentane-3-carboxylic acid; allylglycine (aOly); propargylglycine (pgGly); homoalanine (hAla); norvaline (nVal); homoleucine (hLeu), homovaline (hVal); homoisolencine (hIle); homoarginine (hArg); N acetyl lysine (AcLys); 2,4 diaminobutyric acid (Dbu); 2,3-diaminobutyric acid (Dab); N-methylvaline (MeVal); homocysteine (hCys); homoserine (hSer); hydroxyproline (Hyp) and homoproline (hPro). Additional non-encoded amino acids of which the polypeptides described herein may be comprised will be apparent to those of skill in the art (see, e.g., the various amino acids provided in Fasman, 1989, CRC Practical Handbook of Biochemistry and Molecular Biology, CRC Press, Boca Raton, Fla., at pp. 3-70 and the references cited therein, all of which are incorporated by reference). These amino acids may be in either the L or D configuration.

Those of skill in the art will recognize that amino acids or residues bearing side chain protecting groups may also comprise the polypeptides described herein. Non-limiting examples of such protected amino acids, which in this case belong to the aromatic category, include (protecting groups listed in parentheses), but are not limited to: Arg(tos), Cys (methylbenzyl), Cys (nitropyridinesulfenyl), Glu(δ-benzylester), Gln(xanthyl), Asn(N-δ-xanthyl), His(bom), His(benzyl), His(tos), Lys(fmoc), Lys(tos), Ser(O-benzyl), Thr (O-benzyl) and Tyr(O-benzyl).

Non-encoding amino acids that are conformationally constrained of which the polypeptides described herein may be composed include, but are not limited to, N methyl amino acids (L configuration); 1 aminocyclopent-(2 or 3)-ene-4-carboxylic acid; pipecolic acid; azetidine-3-carboxylic acid; homoproline (hPro); and 1 aminocyclopentane-3-carboxylic acid.

As described above the various modifications introduced into the naturally occurring polypeptide to generate an engineered ketoreductase enzyme can be targeted to a specific property of the enzyme.

5.3. Polynucleotides Encoding Engineered Ketoreductases

In another aspect, the present disclosure provides polynucleotides encoding the engineered ketoreductase enzymes. The polynucleotides may be operatively linked to one or more heterologous regulatory sequences that control gene expression to create a recombinant polynucleotide capable of expressing the polypeptide. Expression constructs containing a heterologous polynucleotide encoding the engineered ketoreductase can be introduced into appropriate host cells to express the corresponding ketoreductase polypeptide.

Because of the knowledge of the codons corresponding to the various amino acids, availability of a protein sequence provides a description of all the polynucleotides capable of encoding the subject. The degeneracy of the genetic code, where the same amino acids are encoded by alternative or synonymous codons allows an extremely large number of nucleic acids to be made, all of which encode the improved ketoreductase enzymes disclosed herein. Thus, having identified a particular amino acid sequence, those skilled in the art could make any number of different nucleic acids by simply modifying the sequence of one or more codons in a way which does not change the amino acid sequence of the protein. In this regard, the present disclosure specifically contemplates each and every possible variation of polynucleotides that could be made by selecting combinations based on the possible codon choices, and all such variations are to be considered specifically disclosed for any polypeptide disclosed herein, including the amino acid sequences presented in Table 2.

In some embodiments, the polynucleotide comprises a nucleotide sequence encoding a ketoreductase polypeptide with an amino acid sequence that has at least about 80% or more sequence identity, at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity, or more sequence identity to any of the engineered ketoreductase polypeptides described herein, i.e., a polypeptide comprising an amino acid sequence selected from the group consisting of SEQ ID NO: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, and 80.

In various embodiments, the codons are preferably selected to fit the host cell in which the protein is being produced. For example, preferred codons used in bacteria are used to express the gene in bacteria; preferred codons used in yeast are used for expression in yeast; and preferred codons used in mammals are used for expression in mammalian cells.

For example, the polynucleotide of SEQ ID NO:1 could be codon optimized for expression in *E. coli*, but otherwise encode the naturally occurring ketoreductase of *Novosphingobium aromaticivorans*.

In some embodiments, all codons need not be replaced to optimize the codon usage of the ketoreductases since the natural sequence will comprise preferred codons and because use of preferred codons may not be required for all amino acid residues. Consequently, codon optimized polynucleotides encoding the ketoreductase enzymes may contain preferred codons at about 40%, 50%, 60%, 70%, 80%, or greater than 90% of codon positions of the full length coding region.

In some embodiments, the polynucleotides encoding the engineered ketoreductases are selected from SEQ ID NO:3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, and 79. In some embodiments, the polynucleotides encoding the engineered ketoreductases are capable of hybridizing under highly stringent conditions to a polynucleotide comprising SEQ ID NO: 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, and 79. These polynucleotides encode some of the polypeptides represented by the amino acid sequences listed in Tables 2 and 3.

In other embodiments, the polynucleotides comprise polynucleotides that encode the polypeptides described herein but have about 80% or more sequence identity, about 85% or more sequence identity, about 90% or more sequence identity, about 95% or more sequence identity, about 98% or more sequence identity, or 99% or more sequence identity at the nucleotide level to a reference polynucleotide encoding an engineered ketoreductase. In some embodiments, the reference polynucleotide is selected from polynucleotide sequences represented by SEQ ID NO: 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, and 79.

An isolated polynucleotide encoding an improved ketoreductase polypeptide may be manipulated in a variety of ways to provide for expression of the polypeptide. Manipulation of the isolated polynucleotide prior to its insertion into a vector may be desirable or necessary depending on the expression vector. The techniques for modifying polynucleotides and nucleic acid sequences utilizing recombinant DNA methods are well known in the art. Guidance is provided in Sambrook et al., 2001, Molecular Cloning: A Laboratory Manual, 3rd Ed., Cold Spring Harbor Laboratory Press; and Current Protocols in Molecular Biology, Ausubel. F. ed., Greene Pub. Associates, 1998, updates to 2006.

For bacterial host cells, suitable promoters for directing transcription of the nucleic acid constructs of the present disclosure, include the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, and prokaryotic beta-lactamase gene (Villa-Kamaroff et al., 1978, Proc. Natl Acad. Sci. USA 75: 3727-3731), as well as the tac promoter (DeBoer et al., 1983, Proc. Natl Acad. Sci. USA 80: 21-25).

For filamentous fungal host cells, suitable promoters for directing the transcription of the nucleic acid constructs of the present disclosure include promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, and *Fusarium oxysporum* trypsin-like protease (WO 96/00787), as well as the NA2-tpi promoter (a hybrid of the promoters from the genes for *Aspergillus niger* neutral alpha-amylase and *Aspergillus oryzae* triose phosphate isomerase), and mutant, truncated, and hybrid promoters thereof.

In a yeast host, useful promoters can be from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH2/GAP), and *Saccharomyces cerevisiae* 3-phosphoglycerate kinase. Other useful promoters for yeast host cells are described by Romanos et al., 1992, Yeast 8:423-488.

The control sequence may also be a suitable transcription terminator sequence, a sequence recognized by a host cell to terminate transcription. The terminator sequence is operably linked to the 3' terminus of the nucleic acid sequence encoding the polypeptide. Any terminator which is functional in the host cell of choice may be used in the present invention.

For example, exemplary transcription terminators for filamentous fungal host cells can be obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Exemplary terminators for yeast host cells can be obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, a nontranslated region of an mRNA that is important for translation by the host cell. The leader sequence is operably linked to the 5' terminus of the nucleic acid sequence encoding the polypeptide. Any leader sequence that is functional in the host cell of choice may be used. Exemplary leaders for filamentous fungal host cells are obtained from the genes for *Aspergillus oryzae* TAKA amylase and *Aspergillus nidulans* triose phosphate isomerase. Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3' terminus of the nucleic acid sequence and which, when transcribed, is recognized by the host cell as a signal to add polyadenosine residues to transcribed mRNA. Any polyadenylation sequence which is functional in the host cell of choice may be used in the present invention. Exemplary polyadenylation sequences for filamentous fungal host cells can be from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase. Useful polyadenylation sequences for yeast host cells are described by Guo and Sherman, 1995, Mol Cell Bio 15:5983-5990.

The control sequence may also be a signal peptide coding region that codes for an amino acid sequence linked to the amino terminus of a polypeptide and directs the encoded polypeptide into the cell's secretory pathway. The 5'-end of the coding sequence of the nucleic acid sequence may inherently contain a signal peptide coding region naturally linked in translation reading frame with the segment of the coding region that encodes the secreted polypeptide. Alternatively, the 5'-end of the coding sequence may contain a signal peptide coding region that is foreign to the coding sequence. The foreign signal peptide coding region may be required where the coding sequence does not naturally contain a signal peptide coding region.

Alternatively, the foreign signal peptide coding region may simply replace the natural signal peptide coding region in order to enhance secretion of the polypeptide. However, any signal peptide coding region which directs the expressed polypeptide into the secretory pathway of a host cell of choice may be used in the present invention.

Effective signal peptide coding regions for bacterial host cells are the signal peptide coding regions obtained from the genes for *Bacillus* NC1B 11837 maltogenic amylase, *Bacillus stearothermophilus* alpha-amylase, *Bacillus licheniformis* subtilisin, *Bacillus licheniformis* beta-lactamase, *Bacillus stearothermophilus* neutral proteases (nprT, nprS, nprM), and *Bacillus subtilis* prsA. Further signal peptides are described by Simonen and Palva, 1993, Microbiol Rev 57: 109-137.

Effective signal peptide coding regions for filamentous fungal host cells can be the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, and *Humicola lanuginosa* lipase.

Useful signal peptides for yeast host cells can be from the genes for *Saccharomyces cerevisiae* alpha-factor and *Saccharomyces cerevisiae* invertase. Other useful signal peptide coding regions are described by Romanos et al., 1992, supra.

The control sequence may also be a propeptide coding region that codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* lactase (WO 95/33836).

Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences, which allow the regulation of the expression of the polypeptide relative to the growth of the host cell. Examples of regulatory systems are those which cause the expression of the gene to be turned on or off in response to a chemical or physical stimulus, including the presence of a regulatory compound. In prokaryotic host cells, suitable regulatory sequences include the lac, tac, and trp operator systems. In yeast host cells, suitable regulatory systems include, as examples, the ADH2 system or GAL1 system. In filamentous fungi, suitable regulatory sequences include the TAKA alpha-amylase promoter, *Aspergillus niger* glucoamylase promoter, and *Aspergillus oryzae* glucoamylase promoter.

Other examples of regulatory sequences are those which allow for gene amplification. In eukaryotic systems, these include the dihydrofolate reductase gene, which is amplified in the presence of methotrexate, and the metallothionein genes, which are amplified with heavy metals. In these cases, the nucleic acid sequence encoding the KRED polypeptide of the present invention would be operably linked with the regulatory sequence.

Thus, in another embodiment, the present disclosure is also directed to a recombinant expression vector comprising a polynucleotide encoding an engineered ketoreductase polypeptide or a variant thereof, and one or more expression regulating regions such as a promoter and a terminator, a replication origin, etc., depending on the type of hosts into which they are to be introduced. The various nucleic acid and control sequences described above may be joined together to produce a recombinant expression vector which may include one or more convenient restriction sites to allow for insertion or substitution of the nucleic acid sequence encoding the polypeptide at such sites. Alternatively, the nucleic acid sequence of the present disclosure may be expressed by inserting the nucleic acid sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus), which can be conveniently subjected to recombinant DNA procedures and can bring about the expression of the polynucleotide sequence. The choice of the vector will typically depend on the compatibility of the vector with the host cell into which the vector is to be introduced. The vectors may be linear or closed circular plasmids.

The expression vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The expression vector of the present invention preferably contains one or more selectable markers, which permit easy selection of transformed cells. A selectable marker is a gene the product of which provides for biocide or viral resistance, resistance to heavy metals, prototrophy to auxotrophs, and the like. Examples of bacterial selectable markers are the dal genes from *Bacillus subtilis* or *Bacillus licheniformis*, or markers, which confer antibiotic resistance such as ampicillin, kanamycin, chloramphenicol or tetracycline resistance. Suitable markers for yeast host cells are ADE2, HIS3, LEU2, LYS2, MET3, TRP1, and URA3.

Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), cysC (sulfate adenyltransferase), and trpC (anthranilate synthase), as well as equivalents thereof. Embodiments for use in an *Aspergillus* cell include the amdS and pyrG genes of *Aspergillus nidulans* or *Aspergillus oryzae* and the bar gene of *Streptomyces hygroscopicus*.

The expression vectors of the present invention preferably contain an element(s) that permits integration of the vector into the host cell's genome or autonomous replication of the vector in the cell independent of the genome. For integration into the host cell genome, the vector may rely on the nucleic acid sequence encoding the polypeptide or any other element of the vector for integration of the vector into the genome by homologous or nonhomologous recombination.

Alternatively, the expression vector may contain additional nucleic acid sequences for directing integration by homologous recombination into the genome of the host cell. The additional nucleic acid sequences enable the vector to be integrated into the host cell genome at a precise location(s) in the chromosome(s). To increase the likelihood of integration at a precise location, the integrational elements should preferably contain a sufficient number of nucleic acids, such as 100 to 10,000 base pairs, preferably 400 to 10,000 base pairs, and most preferably 800 to 10,000 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleic acid sequences. On the other hand, the vector may be integrated into the genome of the host cell by non-homologous recombination.

For autonomous replication, the vector may further comprise an origin of replication enabling the vector to replicate autonomously in the host cell in question. Examples of bacterial origins of replication are P15A ori or the origins of replication of plasmids pBR322, pUC19, pACYC177 (which plasmid has the P15A ori), or pACYC184 permitting replication in *E. coli*, and pUB110, pE194, pTA1060, or pAMß1 permitting replication in *Bacillus*. Examples of origins of replication for use in a yeast host cell are the 2 micron origin of replication, ARS1, ARS4, the combination of ARS1 and CEN3, and the combination of ARS4 and CEN6. The origin of replication may be one having a mutation which makes it's functioning temperature-sensitive in the host cell (see, e.g., Ehrlich, 1978, Proc Natl Acad Sci. USA 75:1433).

More than one copy of a nucleic acid sequence of the present invention may be inserted into the host cell to increase production of the gene product. An increase in the copy number of the nucleic acid sequence can be obtained by integrating at least one additional copy of the sequence into the host cell genome or by including an amplifiable selectable marker gene with the nucleic acid sequence where cells containing amplified copies of the selectable marker gene, and thereby additional copies of the nucleic acid sequence, can be selected for by cultivating the cells in the presence of the appropriate selectable agent.

Many of the expression vectors for use in the present invention are commercially available. Suitable commercial expression vectors include p3×FLAGTMTM expression vectors from Sigma-Aldrich Chemicals, St. Louis Mo., which includes a CMV promoter and hGH polyadenylation site for expression in mammalian host cells and a pBR322 origin of replication and ampicillin resistance markers for amplification in *E. coli*. Other suitable expression vectors are pBluescriptll SK(−) and pBK-CMV, which are commercially available from Stratagene, LaJolla Calif., and plasmids which are derived from pBR322 (Gibco BRL), pUC (Gibco BRL), pREP4, pCEP4 (Invitrogen) or pPoly (Lathe et al., 1987, Gene 57:193-201).

5.4. Host Cells for Expression of Ketoreductase Polypeptides

In another aspect, the present disclosure provides a host cell comprising a polynucleotide encoding an improved ketoreductase polypeptide of the present disclosure, the polynucleotide being operatively linked to one or more control sequences for expression of the ketoreductase enzyme in the host cell. Host cells for use in expressing the KRED polypeptides encoded by the expression vectors of the present invention are well known in the art and include but are not limited to, bacterial cells, such as *E. coli, Lactobacillus, Streptomyces* and *Salmonella typhimurium* cells; fungal cells, such as yeast cells (e.g., *Saccharomyces cerevisiae* or *Pichia pastoris* (ATCC Accession No. 201178)); insect cells such as *Drosophila* S2 and *Spodoptera* Sf9 cells; animal cells such as CHO, COS, BHK, 293, and Bowes melanoma cells; and plant cells. Appropriate culture mediums and growth conditions for the above-described host cells are well known in the art. Accordingly, in some embodiments, the engineered ketoreductase polypeptides disclosed herein can be prepared by standard methods comprising culturing a host cell containing a suitable expression vector comprising the polynucleotide encoding the polypeptide.

Polynucleotides for expression of the ketoreductase may be introduced into cells by various methods known in the art. Techniques include among others, electroporation, biolistic particle bombardment, liposome mediated transfection, calcium chloride transfection, and protoplast fusion. Various methods for introducing polynucleotides into cells will be apparent to the skilled artisan.

An exemplary host cell is *Escherichia coli* W3110. Another exemplary host cell is *Escherichia coli* BL21. The expression vector is created by operatively linking a polynucleotide encoding an improved ketoreductase into the plasmid pCK110900 (see, US application publication 20040137585) operatively linked to the lac promoter under control of the lad repressor. The expression vector also contains the P15a origin of replication and the chloramphenicol resistance gene. Cells containing the subject polynucleotide in *Escherichia coli* W3110 or BL21 are isolated by subjecting the cells to chloramphenicol selection.

5.5. Methods of Generating Engineered Ketoreductase Polypeptides.

In some embodiments, to make the improved KRED polynucleotides and polypeptides of the present disclosure, the naturally-occurring ketoreductase enzyme that catalyzes the reduction reaction is obtained (or derived) from *Novosphingobium aromaticivorans*. In some embodiments, the parent polynucleotide sequence is codon optimized to enhance expression of the ketoreductase in a specified host cell. As an illustration, the parental polynucleotide sequence encoding the wild-type KRED polypeptide of *Novosphingobium aromaticivorans* (SEQ ID NO:1), can be assembled from oligonucleotides based upon that sequence or from oligonucleotides comprising a codon-optimized coding sequence for expression in a specified host cell, e.g., an *E. coli* host cell. In one embodiment, the polynucleotide can be cloned into an expression vector, placing the expression of the ketoreductase gene under the control of the lac promoter and lad repressor gene. Clones expressing the active ketoreductase in *E. coli* can be identified and the genes sequenced to confirm their identity.

The engineered ketoreductases can be obtained by subjecting the polynucleotide encoding the naturally occurring ketoreductase to mutagenesis and/or directed evolution methods, as discussed above. An exemplary directed evolution technique is mutagenesis and/or DNA shuffling as described in Stemmer, 1994, Proc Natl Acad Sci USA 91:10747-10751; WO 95/22625; WO 97/0078; WO 97/35966; WO 98/27230; WO 00/42651; WO 01/75767 and U.S. Pat. No. 6,537,746. Other directed evolution procedures that can be used include, among others, staggered extension process (StEP), in vitro recombination (Zhao et al., 1998, Nat. Biotechnol. 16:258-261), mutagenic PCR (Caldwell et al., 1994, PCR Methods Appl. 3:S136-S140), and cassette mutagenesis (Black et al., 1996, Proc Natl Acad Sci USA 93:3525-3529).

The clones obtained following mutagenesis treatment are screened for engineered ketoreductases having a desired improved enzyme property. Measuring enzyme activity from the expression libraries can be performed using the standard biochemistry technique of monitoring the rate of decrease (via a decrease in absorbance or fluorescence) of NADH or NADPH concentration, as it is converted into NAD+ or NADP+. In this reaction, the NADH or NADPH is consumed (oxidized) by the ketoreductase as the ketoreductase reduces a ketone substrate to the corresponding hydroxyl group. The rate of decrease of NADH or NADPH concentration, as measured by the decrease in absorbance or fluorescence, per unit time indicates the relative (enzymatic) activity of the KRED polypeptide in a fixed amount of the lysate (or a lyophilized powder made therefrom). Where the improved enzyme property desired is thermal stability, enzyme activity may be measured after subjecting the enzyme preparations to a defined temperature and measuring the amount of enzyme activity remaining after heat treatments. Clones containing a polynucleotide encoding a ketoreductase are then isolated, sequenced to identify the nucleotide sequence changes (if any), and used to express the enzyme in a host cell.

Where the sequence of the engineered polypeptide is known, the polynucleotides encoding the enzyme can be prepared by standard solid-phase methods, according to known synthetic methods. In some embodiments, fragments of up to about 100 bases can be individually synthesized, then joined (e.g., by enzymatic or chemical litigation methods, or polymerase mediated methods) to form any desired continuous sequence. For example, polynucleotides and oligonucleotides of the invention can be prepared by chemical synthesis using, e.g., the classical phosphoramidite method described by Beaucage et al., 1981, Tet Left 22:1859-69, or the method described by Matthes et al., 1984, EMBO J. 3:801-05, e.g., as it is typically practiced in automated synthetic methods. According to the phosphoramidite method, oligonucleotides are synthesized, e.g., in an automatic DNA synthesizer, purified, annealed, ligated and cloned in appropriate vectors. In addition, essentially any nucleic acid can be obtained from any of a variety of commercial sources, such as The Midland Certified Reagent Company, Midland, Tex., The Great American Gene Company, Ramona, Calif., ExpressGen Inc. Chicago, Ill., Operon Technologies Inc., Alameda, Calif., and many others.

Engineered ketoreductase enzymes expressed in a host cell can be recovered from the cells and or the culture medium using any one or more of the well known techniques for protein purification, including, among others, lysozyme treatment, sonication, filtration, salting-out, ultra-centrifugation, and chromatography. Suitable solutions for lysing and the high efficiency extraction of proteins from bacteria, such as *E. coli*, are commercially available under the trade name Cel-Lytic BTM from Sigma-Aldrich of St. Louis Mo. Accordingly, in some embodiments, the engineered ketoreductase polypeptides disclosed herein can be prepared by standard methods comprising culturing a host cell containing a suitable expression vector comprising the polynucleotide encoding the polypeptide and isolating the polypeptide from the host cell.

Chromatographic techniques for isolation of the ketoreductase polypeptide include, among others, reverse phase chromatography high performance liquid chromatography, ion exchange chromatography, gel electrophoresis, and affinity chromatography. Conditions for purifying a particular enzyme will depend, in part, on factors such as net charge, hydrophobicity, hydrophilicity, molecular weight, molecular shape, etc., and will be apparent to those having skill in the art.

In some embodiments, affinity techniques may be used to isolate the improved ketoreductase enzymes. For affinity chromatography purification, any antibody which specifically binds the ketoreductase polypeptide may be used. For the production of antibodies, various host animals, including but not limited to rabbits, mice, rats, etc., may be immunized by injection with a polypeptide of the disclosure. The polypeptide may be attached to a suitable carrier, such as BSA, by means of a side chain functional group or linkers attached to a side chain functional group. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacilli Calmette Guerin) and *Corynebacterium parvum*.

5.6. Methods of Using the Engineered Ketoreductase Enzymes and Compounds Prepared Therewith The ketoreductase enzymes described herein can catalyze the enantiospecific reduction of the N-protected (S)-3-amino-1-chloro-4-phenylbutan-2-one compound of Formula (I) ("the substrate") (e.g. compound (1) where the protecting group is a BOC moiety) to the corresponding stereoisomeric alcohol product N-protected (2R,3S)-3-amino-1-chloro-4-phenylbutan-2-ol compound of Formula (II) ("the product") (e.g. compound (2)), as depicted in Scheme 1 (see above).

In some embodiments, the invention provides a method for stereospecifically enriching an N-protected (R)-3-amino-1-chloro-4-phenylbutan-2-one compound in a mixture with an N-protected (S)-3-amino-1-chloro-4-phenylbutan-2-one by reducing the latter ketone compound in the mixture by contacting or incubating with a ketoreductase polypeptide disclosed herein under suitable reaction conditions for producing a chiral alcohol product, N-protected (2R,3S)-3-amino-1-chloro-4-phenylbutan-2-ol, as illustrated in the reaction of Scheme 5 (see above). Accordingly, in some embodiments, the ketoreductase polypeptides having improved stereospecificity (compared to SEQ ID NO: 2) of the present disclosure can be use to resolve mixtures of chiral alpha-chloroketone compounds.

In some embodiments of the method, at least about 45% of a racemic substrate mixture is reduced to the product in less than 24, 23, 22, 21, 20, 19, 18, 17, 16, 15, 14, 13, 12, 11, 10, 9, 8, or 7 hours when the method is conducted with greater than or equal to 200 g/L substrate and less than or equal to 2 g/L ketoreductase enzyme (but more than 0 g/L enzyme).

The processes for converting a compound of Formula (I) to a chiral chloroalcohol compound of Formula (II) using ketoreductase enzymes disclosed herein represent substantial improvements over known methods due in part to the resulting high yield (e.g., conversion rate>80% or more in less than 24 hours), high purity (e.g., >99% d.e.), and favorable solvent systems that allow for a "telescoped" reaction for preparing the compound of Formula (II) and using it as a reagent for subsequent reaction.

In some embodiments of the methods, the product has greater than about 90%, 95%, 97%, 98%, 99%, or even greater diastereomeric excess of the N-protected (2R,3S)-3-amino-1-chloro-4-phenylbutan-2-ol.

In some embodiments of the methods, about 95% of the substrate is converted to the product in less than about 24 hours when carried out with greater than about 100 g/L of substrate and less than about 5 g/L of the polypeptide.

In some embodiments of the methods at least about 90%, 95%, 97%, 98%, or more, of the compound of Formula (I) is converted to the compound of Formula (II) in less than about 24 hours, 20 hours, 12 hours, 8 hours, or even less.

In some embodiments of the methods at least about 95% of the compound of Formula (I) is converted to the compound of Formula (II) in less than about 24 hours, wherein the compound of Formula (I) concentration is at least about 150 g/L and the polypeptide concentration is less than about 1 g/L.

In certain embodiments, the present disclosure further provides a method for preparing an epoxide compound of Formula (III) by converting a compound of Formula (I) to a chiral chloroalcohol compound of Formula (II) (e.g., compound (2)) using a ketoreductase of the present disclosure, and then cyclizing the compound of Formula (II) to an epoxide compound of Formula (III) (e.g., compound (3)), according to Schemes 3 and 4, depicted above. This conversion can be carried out very efficiently by extracting the crude enzymatic reaction mixture containing the compound of Formula (II) with a suitable solvent (e.g., MTBE) and contacting this extract with a suitable base (e.g., KOH).

In certain embodiments of the methods provided herein, the base is selected from potassium hydroxide (KOH), potassium tert-butoxide, potassium carbonate, and triethylamine.

In certain embodiments, the preparation of compound (3) can be carried by reacting 0.3 M compound (2) in MTBE (e.g., crude extract from ketoreductase reaction mixture) with 0.6 M KOH (or other suitable base) in MTBE solution. This reaction reaches >99% conversion to the epoxide of compound (3) within 5 hours and 99.9% conversion within 8 hours (determined via HPLC).

In certain embodiments, the methods for preparing compounds of Formula (III) of the present disclosure comprise the steps of extracting the enzyme reaction mixture with an organic solvent, and contacting the organic solvent extract with a base. In certain embodiments, the method is carried out wherein said step of contacting the compound of Formula (II) with base is carried out without first purifying and/or isolating the compound of Formula (II) (e.g., a "telescoped" reaction or a "one-pot" reaction).

Thus, in some embodiments, the present disclosure provides in a method for preparing a compound of Formula (III) (e.g., compound (3)) the step of converting the compound of Formula (I) to a compound of Formula (II) (e.g., compound (2)) using a ketoreductase of the present disclosure. In some embodiments of preparing compounds of Formula (III), the method further comprises the step of contacting the compound of Formula (II) with base. In certain embodiments, the method is carried out wherein said step of contacting the compound of Formula (II) with base is carried out without first purifying and/or isolating the compound of Formula (II).

In certain embodiments, the method further comprises exchanging (or swapping) the organic solvent of the organic solvent extract with a crystallization solvent, and crystallizing the compound of Formula (III) from the crystallization solvent. In certain embodiments, the organic solvent extract is MTBE which is exchanged for the crystallization solvent, heptane.

Other organic solvents that may be used for extraction and crystallization according to the methods provided herein are those well-known in the art and accessible to the ordinary artisan, including well-known hydrocarbons, ethers, esters, and alcohols e.g., acetonitrile, n-butanol, toluene, isopropyl acetate.

As noted above, any of the ketoreductase polypeptides described herein, including those exemplified in Table 2, can be used in the methods. Moreover, in some embodiments, the methods can use a ketoreductase polypeptides comprising an amino acid sequence that is at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO:2, and, further, that comprises, as compared to SEQ ID NO:2, at least one amino acid substitution selected from the group consisting of: the proline residue at position 2 is replaced with an aliphatic or nonpolar amino acid selected from among alanine, leucine, valine, isoleucine, glycine and methionine; the valine residue at position 28, in a conservative change, is replaced with an aliphatic or nonpolar amino acid selected from among alanine, leucine, valine, isoleucine, glycine and methionine; the alanine residue at position 34 is replaced with a polar amino acid selected from among asparagine, glutamine, serine, and threonine; the alanine residue at position 47, in a conservative change, is replaced with an aliphatic or nonpolar amino acid selected from among alanine, leucine, valine, isoleucine, glycine and methionine; the glutamic acid residue at position 50 is replaced with a basic amino acid selected from lysine and arginine; the aspartic acid residue at position 81 is replaced with a polar amino acid selected from among asparagine, glutamine, serine, and threonine; the serine residue at position 90 is replaced with an aliphatic or nonpolar amino acid selected from among alanine, leucine, valine, isoleucine, glycine and methionine; the isoleucine residue at position 91 is, in a conservative change, replaced with an aliphatic or nonpolar amino acid selected from among alanine, leucine, valine, isoleucine, glycine and methionine, while in other aspects, the isoleucine residue at position 91 is replaced with an aromatic amino acid selected from among tyrosine, tryptophan, and phenylalanine, or a basic amino acid selected from among lysine and arginine; the lysine residue at position 94 is, in a conservative change, replaced with another basic amino acid, arginine; the aspartic acid residue at position 112 is replaced with an aromatic amino acid selected from among tyrosine, tryptophan, and phenylalanine; the glycine residue at position 117 is replaced with an acidic amino acid selected from among aspartic acid and glutamic acid; the serine residue at position 143 is replaced with a basic amino acid selected from among lysine and arginine; the valine residue at position 144 is replaced with a cysteine or a polar amino acid selected from among asparagine, glutamine, serine, and threonine; the glycine residue at position 145, in either a conservative or non-conservative change, may be replaced with a nonpolar amino acid selected from among alanine, leucine, valine, isoleucine, and methionine or an aliphatic amino acid selected from among alanine, leucine, valine, isoleucine; the arginine residue at position 148 is replaced with a constrained amino acid selected from among proline and histidine; the alanine residue at position 150, in conservative or non-conservative change, is replaced with another nonpolar or aliphatic amino acid selected from among leucine, valine, isoleucine, glycine and methionine, or a polar amino acid selected from among asparagine, glutamine, serine, and threonine, or an aromatic amino acid selected from among tyrosine, tryptophan, and phenylalanine; the phenylalanine residue at position 152 is replaced with a nonpolar or aliphatic amino acid selected from among alanine, leucine, valine, isoleucine, glycine and methionine; the asparagine residue at position 153 is replaced with a nonpolar or aliphatic amino acid selected from among alanine, leucine, valine, isoleucine, glycine and methionine, or with a constrained amino acid selected from among histidine and proline; the threonine residue at position 158, in a conservative change, is replaced with another polar amino acid selected from among asparagine, glutamine, and serine; the glycine residue at position 190, in either a conservative or a nonconservative change, is replaced with either a nonpolar or an aliphatic amino acid selected from among alanine, valine, leucine, isoleucine, glycine, and methionine, or a polar amino acid selected from among asparagine, glutamine, and serine, or a proline; the serine residue at position 198, in a conservative change, is replaced with another polar amino acid selected from among asparagine, glutamine, and threonine; the isoleucine residue at position 199 is, in a conservative change replaced with another aliphatic or nonpolar amino acid selected from among alanine, leucine, valine, glycine, and methionine, or with a polar amino acid selected from among asparagine, glutamine, serine, and threonine; the methionine residue at position 200, in a conservative change, is replaced with another nonpolar amino acid selected from among alanine, leucine, valine, isoleucine, and glycine; the valine at position 204, in a non-conservative change, is replaced with an aromatic amino acid selected from among tyrosine, tryptophan, and phenylalanine; the alanine residue at position 217 is replaced with a polar amino acid selected from among asparagine, glutamine, serine and threonine; the isoleucine residue at position 225, in a conservative change, is replaced with an other nonpolar amino acid selected from among valine, leucine, glycine, and methionine; the proline residue at position 231 is replaced with an aromatic amino acid selected from among tyrosine, tryptophan, and phenylalanine; the alanine residue at position 232, in a conservative change, is replaced with another nonpolar amino acid selected from among leucine, isoleucine, valine, glycine, and methionine; the glutamic acid residue at position 233 is replaced with a polar amino acid selected from among asparagine, glutamine, serine, and threonine; the aspartic acid residue at position 244 is replaced with a nonpolar amino acid selected from among alanine, leucine, isoleucine, valine, glycine, and methionine; the phenylalanine residue at position 260, in a conservative change, is replaced with another aromatic amino acid selected from among tyrosine and tryptophan; and the serine residue at position 261, in a conservative change, is replaced with another polar amino acid selected from among asparagine, glutamine, and threonine. The forgoing improved ketoreductase polypeptides may further comprise additional modifications, including substitutions, deletions, insertions, or combinations thereof. The substitutions can be non-conservative substitutions, conservative substitutions, or a combination of non-conservative and conservative substitutions. In some embodiments, these ketoreductase polypeptides can have optionally from about 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 mutations at other amino acid residues. In some embodiments, the number of modifications can be 1, 2, 3, 4, 5, 6, 7, 8, 9, 10, 11, 12, 14, 15, 16, 18, 20, 22, 24, 26, 30, 35 or about 40 other amino acid residues.

In some embodiments, the methods can use an improved ketoreductase polypeptide of the present disclosure that comprises an amino acid sequence that is at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO:2, and that further comprises, as compared to SEQ ID NO:2, at least one amino acid substitution selected from the group consisting of: the proline residue at position 2 is replaced with leucine (P2L); the valine residue at position 28 is replaced with alanine (V28A); the alanine residue at position 34 is replaced with serine (A34S); the alanine residue at position 47 is replaced with valine (A47V); the glutamic acid residue at position 50 is replaced with lysine (E50K); the aspartic acid residue at position 81 is replaced with asparagine (D81N); the serine residue at position 90 is replaced with valine (S90V); the isoleucine residue at position 91 is replaced with an amino acid selected from among leucine (I91L), tryptophan (I91W), arginine (I91R), and lysine (I91K); the lysine residue at position 94 is replaced with arginine (K94R); the aspartic acid residue at position 112 is replaced with tyrosine (D112Y); the glycine residue at position 117 is replaced with aspartic acid (G117D); the serine residue at position 143 is replaced with arginine (S143R); the valine residue at position 144 is replaced with an amino acid selected from among cysteine (V144C) and threonine (V144T); the glycine residue at position 145 is replaced with an amino acid selected from among alanine (G145A) and valine (G145V); the arginine residue at position 148 is replaced with histidine (R148H); the alanine residue at position 150 is replaced with an amino acid selected from among glycine (A150G), isoleucine (A150I), serine (A150S), and tryptophan (A150W); the phenylalanine residue at position 152 is replaced with leucine (F152L); the asparagine residue at position 153 is replaced with an amino acid selected from among glycine (N153G), valine (N153V), and histidine (N153H); the threonine residue at position 158 is replaced with serine (T158S); the glycine residue at position 190 is replaced with an amino acid selected from among alanine (G190A), proline (G190P), glutamine (G190Q), and valine (G190V); the serine residue at position 198 is replaced with asparagine (S198N); the isoleucine residue at position 199 is replaced with an amino acid selected from among glycine (I199G), methionine (I199M), leucine (I199L), and asparagine (I199N); the methionine residue at position 200 is replaced with isoleucine (M200I); the valine residue at position 204 is replaced with phenylalanine (V204F); the alanine residue at position 217 is replaced with threonine (A217T); the isoleucine residue at position 225 is replaced with valine (I225V); the proline residue at position 231 is replaced with phenylalanine (P231F); the alanine residue at position 232 is replaced with valine (A232V); the glutamic acid residue at position 233 is replaced with glutamine (E233Q); the aspartic acid residue at position 244 is replaced with glycine (D244G); the phenylalanine residue at position 260 is replaced with tyrosine (F260Y); and the serine residue at position 261 is replaced with asparagine (S261N). In certain embodiments, a ketoreductase polypeptide of the present disclosure comprises an amino acid sequence selected from the group consisting of SEQ ID NO: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 65, 66, 68, 70, 72, 74, 76, 78, and 80. The forgoing improved ketoreductase polypeptides may further comprise additional modifications, including substitutions, deletions, insertions, or combinations thereof. The substitutions can be non-conservative substitutions, conservative substitutions, or a combination of non-conservative and conservative substitutions. In some embodiments, these ketoreductase polypeptides can have optionally from about 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 mutations at other amino acid residues. In some embodiments, the number of modifications can be 1, 2, 3, 4, 5, 6, 7, 8, 9, 10, 11, 12, 14, 15, 16, 18, 20, 22, 24, 26, 30, 35 or about 40 other amino acid residues.

In some embodiments, the methods of the present disclosure use a ketoreductase comprising the amino acid sequence selected from the group consisting of SEQ ID NO: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 65, 66, 68, 70, 72, 74, 76, 78, 80, and combinations thereof. Exemplary groups comprising combinations of sequences include: the group consisting of SEQ ID NOs 4, 6, 14, 16, 18, 22, 24, 26, 28, 30, 32, 34, 36, 38, 40, 50, 52, 54, and 56; the group consisting of SEQ ID NOs 6, 18, 22, 30, 38, 40, 50, 52, 54, and 56; and the group consisting of SEQ ID NOs 6, 50, 52, and 56.

In some embodiments of the method, the product has greater than about 90%, 95%, 97%, 98%, 99%, or even greater diastereomeric excess of the N-protected (2R,3S)-3-amino-1-chloro-4-phenylbutan-2-ol, wherein the ketoreductase polypeptide comprises an amino acid sequence corresponding to SEQ ID NO: 4, 6, 8, 10, 12, 14, 16, 18, 20, 22, 24, 26, 28, 30, 32, 34, 36, 38, 40, 42, 44, 46, 48, 50, 52, 54, 56, and 58.

In some embodiments of the method, at least about 45% of a racemic substrate mixture is reduced to the product in less than 24, 23, 22, 21, 20, 19, 18, 17, 16, 15, 14, 13, 12, 11, 10, 9, 8, or 7 hours when the method is conducted with greater than or equal to 200 g/L substrate and less than or equal to 2 g/L ketoreductase enzyme (but more than 0 g/L enzyme), wherein the ketoreductase polypeptide comprises an amino acid sequence corresponding to SEQ ID NO:6, 50, 52, and 56.

As is known by those of skill in the art, ketoreductase-catalyzed reduction reactions typically require a cofactor. Reduction reactions catalyzed by the engineered ketoreductase enzymes described herein also typically require a cofactor, although many embodiments of the engineered ketoreductases require far less cofactor than reactions catalyzed with wild-type ketoreductase enzymes. As used herein, the term "cofactor" refers to a non-protein compound that operates in combination with a ketoreductase enzyme. Cofactors suitable for use with the engineered ketoreductase enzymes described herein include, but are not limited to, NADP$^+$ (nicotinamide adenine dinucleotide phosphate), NADPH (the reduced form of NADP$^+$), NAD$^+$ (nicotinamide adenine dinucleotide) and NADH (the reduced form of NAD$^+$). Generally, the reduced form of the cofactor is added to the reaction mixture. The reduced NAD(P)H form can be optionally regenerated from the oxidized NAD(P)$^+$ form using a cofactor regeneration system.

The term "cofactor regeneration system" refers to a set of reactants that participate in a reaction that reduces the oxidized form of the cofactor (e.g., NADP$^+$ to NADPH). Cofactors oxidized by the ketoreductase-catalyzed reduction of the keto substrate are regenerated in reduced form by the cofactor regeneration system. Cofactor regeneration systems comprise a stoichiometric reductant that is a source of reducing hydrogen equivalents and is capable of reducing the oxidized form of the cofactor. The cofactor regeneration system may further comprise a catalyst, for example an enzyme that catalyzes the reduction of the oxidized form of the cofactor by the reductant. Cofactor regeneration systems to regenerate NADH or NADPH from NAD+ or NADP+, respectively, are known in the art and may be used in the methods described herein.

Suitable exemplary cofactor regeneration systems that may be employed include, but are not limited to, glucose and glucose dehydrogenase, formate and formate dehydrogenase, glucose-6-phosphate and glucose-6-phosphate dehydrogenase, a secondary (e.g., isopropanol) alcohol and secondary alcohol dehydrogenase, phosphite and phosphite dehydrogenase, molecular hydrogen and hydrogenase, and the like. These systems may be used in combination with either NADP$^+$/NADPH or NAD$^+$/NADH as the cofactor. Electrochemical regeneration using hydrogenase may also be used as a cofactor regeneration system. See, e.g., U.S. Pat. Nos. 5,538,867 and 6,495,023, both of which are incorporated herein by reference. Chemical cofactor regeneration systems comprising a metal catalyst and a reducing agent (for example, molecular hydrogen or formate) are also suitable. See, e.g., PCT publication WO 2000/053731, which is incorporated herein by reference.

The terms "glucose dehydrogenase" and "GDH" are used interchangeably herein to refer to an NAD+ or NADP+-dependent enzyme that catalyzes the conversion of D-glucose and NAD+ or NADP+ to gluconic acid and NADH or NADPH, respectively. Equation (1), below, describes the glucose dehydrogenase-catalyzed reduction of NAD+ or NADP+ by glucose:

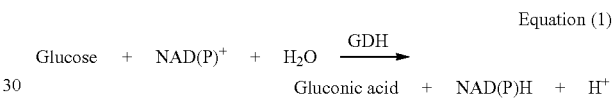

$$\text{Glucose} + \text{NAD(P)}^+ + \text{H}_2\text{O} \xrightarrow{\text{GDH}} \text{Gluconic acid} + \text{NAD(P)H} + \text{H}^+ \quad \text{Equation (1)}$$

Glucose dehydrogenases that are suitable for use in the practice of the methods described herein include both naturally occurring glucose dehydrogenases, as well as non-naturally occurring glucose dehydrogenases. Naturally occurring glucose dehydrogenase encoding genes have been reported in the literature. For example, the *Bacillus subtilis* 61297 GDH gene was expressed in *E. coli* and was reported to exhibit the same physicochemical properties as the enzyme produced in its native host (Vasantha et al., 1983, Proc. Natl. Acad. Sci. USA 80:785). The gene sequence of the *B. subtilis* GDH gene, which corresponds to Genbank Acc. No. M12276, was reported by Lampel et al., 1986, J. Bacteriol. 166:238-243, and in corrected form by Yamane et al., 1996, Microbiology 142:3047-3056 as Genbank Acc. No. D50453. Naturally occurring GDH genes also include those that encode the GDH from *B. cereus* ATCC 14579 (Nature, 2003, 423:87-91; Genbank Acc. No. AE017013) and *B. megaterium* (Eur. J. Biochem., 1988, 174:485-490, Genbank Acc. No. X12370; J. Ferment. Bioeng., 1990, 70:363-369, Genbank Acc. No. GI216270). Glucose dehydrogenases from *Bacillus* sp. are provided in PCT publication WO 2005/018579 as SEQ ID NOS: 10 and 12 (encoded by polynucleotide sequences corresponding to SEQ ID NOS: 9 and 11, respectively, of the PCT publication), the disclosure of which is incorporated herein by reference.

Non-naturally occurring glucose dehydrogenases may be generated using known methods, such as, for example, mutagenesis, directed evolution, and the like. GDH enzymes having suitable activity, whether naturally occurring or non-naturally occurring, may be readily identified using the assay described in Example 4 of PCT publication WO 2005/018579, the disclosure of which is incorporated herein by reference. Exemplary non-naturally occurring glucose dehydrogenases are provided in PCT publication WO 2005/018579 as SEQ ID NO: 62, 64, 66, 68, 122, 124, and 126. The polynucleotide sequences that encode them are provided in PCT publication WO 2005/018579 as SEQ ID NO: 61, 63, 65, 67, 121, 123, and 125, respectively. All of these sequences are incorporated herein by reference. Additional non-naturally occurring glucose dehydrogenases that are suitable for use in the ketoreductase-catalyzed reduction reactions disclosed herein are provided in U.S. application publication Nos. 2005/0095619 and 2005/0153417, the disclosures of which are incorporated herein by reference.

Glucose dehydrogenases employed in the ketoreductase-catalyzed reduction reactions described herein may exhibit an activity of at least about 10 μmol/min/mg and sometimes at least about $10^2$ μmol/min/mg or about $10^3$ μmol/min/mg, up to about $10^4$ μmol/min/mg or higher in the assay described in Example 4 of PCT publication WO 2005/018579.

The ketoreductase-catalyzed reduction reactions described herein are generally carried out in a solvent. Suitable solvents include water, organic solvents (e.g., ethyl acetate, butyl acetate, 2-propanol (isopropanol or IPA), 1-octanol, heptane, octane, methyl t-butyl ether (MTBE), toluene, and the like), ionic liquids (e.g., 1-ethyl-4-methylimidazolium tetrafluoroborate, 1-butyl-3-methylimidazolium tetrafluoroborate, 1-butyl-3-methylimidazolium hexafluorophosphate, and the like). In some embodiments, aqueous solvents, including water and aqueous co-solvent systems, are used.

Exemplary aqueous co-solvent systems have water, pH buffering salts, and one or more organic solvent. In general, an organic solvent component of an aqueous co-solvent system is selected such that it does not completely inactivate the ketoreductase enzyme. Appropriate co-solvent systems can be readily identified by measuring the enzymatic activity of the specified engineered ketoreductase enzyme with a defined substrate of interest in the candidate solvent system, utilizing an enzyme activity assay, such as those described herein.

The organic solvent component of an aqueous co-solvent system may be miscible with the aqueous component, providing a single liquid phase, or may be partly miscible or immiscible with the aqueous component, providing two liquid phases. Generally, when an aqueous co-solvent system is employed, it is selected to be biphasic, with water dispersed in an organic solvent, or vice-versa. Generally, when an aqueous co-solvent system is utilized, it is desirable to select an organic solvent that can be readily separated from the aqueous phase. In general, the ratio of water to organic solvent in the co-solvent system is typically in the range of from about 90:10 to about 10:90 (v/v) organic solvent to water, and between 80:20 and 20:80 (v/v) organic solvent to water. The co-solvent system may be pre-formed prior to addition to the reaction mixture, or it may be formed in situ in the reaction vessel. In certain embodiments, the aqueous co-solvent system comprises isopropyl alcohol (IPA) of about 5%-40% (v/v), about 5%-20% (v/v), about 10-20% (v/v), about 15% (v/v), or about 10% (v/v).

The aqueous solvent (water or aqueous co-solvent system) may be pH-buffered or unbuffered. Generally, the reduction can be carried out at a pH of about 10 or below, usually in the range of from about 5 to about 10. In some embodiments, the reduction is carried out at a pH of about 9.5 or below, usually in the range of from about 6.5 to about 9.5. The reduction may be carried out at a pH of about 7.0 to about 9.5. In certain embodiments, the reduction is carried out at a pH of about 8.5 to about 9.5. In a particular embodiment, the reduction is carried out at a pH of about 9.0. Alternatively, the reduction may be carried out at neutral pH, i.e., about 7.

In certain embodiments where an aqueous co-solvent is used, the reaction conditions for reduction can comprise a pH of about 8.5 to about 9.5 and about 5% to about 40% IPA, about pH 9.0 to 9.5 and about 25% to about 40% IPA, about pH 8.5 to 9.5 and about 5% to about 15% IPA, or about pH 9.0 and about 10% IPA. In certain embodiments, the reaction conditions for reduction can comprise a pH of about 6.5 to about 7.0 and about 5% to about 15% IPA, or about pH 7.0 and about 5% to 10% IPA.

During the course of the reduction reactions, the pH of the reaction mixture (e.g., the aqueous co-solvent solution) may change. The pH of the reaction mixture may be maintained at a desired pH or within a desired pH range by the addition of an acid or a base during the course of the reaction. Alternatively, the pH may be controlled by using an aqueous solvent that comprises a buffer. Suitable buffers to maintain desired pH ranges are known in the art and include, for example, phosphate buffer, triethanolamine buffer (TEA), and the like. Combinations of buffering and acid or base addition may also be used. Accordingly, in certain embodiments, the aqueous co-solvents having pH and organic solvent (e.g., IPA) in certain ranges specified above, may also comprise a buffer such as TEA.

When the glucose/glucose dehydrogenase cofactor regeneration system is employed, the co-production of gluconic acid (pKa=3.6), as represented in equation (1) causes the pH of the reaction mixture to drop if the resulting aqueous gluconic acid is not otherwise neutralized. The pH of the reaction mixture may be maintained at the desired level by standard buffering techniques, wherein the buffer neutralizes the gluconic acid up to the buffering capacity provided, or by the addition of a base concurrent with the course of the conversion. Combinations of buffering and base addition may also be used. Suitable buffers to maintain desired pH ranges are described above. Suitable bases for neutralization of gluconic acid are organic bases, for example amines, alkoxides and the like, and inorganic bases, for example, hydroxide salts (e.g., NaOH), carbonate salts (e.g., $NaHCO_3$), bicarbonate salts (e.g., $K_2CO_3$), basic phosphate salts (e.g., $K_2HPO_4$, $Na_3PO_4$), and the like. The addition of a base concurrent with the course of the conversion may be done manually while monitoring the reaction mixture pH or, more conveniently, by using an automatic titrator as a pH stat. A combination of partial buffering capacity and base addition can also be used for process control.

When base addition is employed to neutralize gluconic acid released during a ketoreductase-catalyzed reduction reaction, the progress of the conversion may be monitored by the amount of base added to maintain the pH. Typically, bases added to unbuffered or partially buffered reaction mixtures over the course of the reduction are added in aqueous solutions.

In some embodiments, the co-factor regenerating system can comprises a formate dehydrogenase. The terms "formate dehydrogenase" and "FDH" are used interchangeably herein to refer to an NAD+ or NADP+-dependent enzyme that catalyzes the conversion of formate and NAD+ or NADP+ to carbon dioxide and NADH or NADPH, respectively. Formate dehydrogenases that are suitable for use as cofactor regenerating systems in the ketoreductase-catalyzed reduction reactions described herein include both naturally occurring formate dehydrogenases, as well as non-naturally occurring formate dehydrogenases. Formate dehydrogenases include those corresponding to SEQ ID NOS: 70 (*Pseudomonas* sp.) and 72 (*Candida boidinii*) of PCT publication WO 2005/018579, which are encoded by polynucleotide sequences corresponding to SEQ ID NOS: 69 and 71, respectively, of PCT publication 2005/018579, the disclosures of which are incorporated herein by reference. Formate dehydrogenases employed in the methods described herein, whether naturally occurring or non-naturally occurring, may exhibit an activity of at least about 1 μmol/min/mg, sometimes at least about 10 μmol/min/mg, or at least about $10^2$ μmol/min/mg, up to about $10^3$ μmol/min/mg or higher, and can be readily screened for activity in the assay described in Example 4 of PCT publication WO 2005/018579.

As used herein, the term "formate" refers to formate anion ($HCO_2^-$), formic acid ($HCO_2H$), and mixtures thereof. Formate may be provided in the form of a salt, typically an alkali or ammonium salt (for example, $HCO_2Na$, $KHCO_2NH_4$, and the like), in the form of formic acid, typically aqueous formic acid, or mixtures thereof. Formic acid is a moderate acid. In aqueous solutions within several pH units of its pKa ($pK_a$=3.7 in water) formate is present as both $HCO_2^-$ and $HCO_2H$ in equilibrium concentrations. At pH values above about pH 4, formate is predominantly present as $HCO_2^-$. When formate is provided as formic acid, the reaction mixture is typically buffered or made less acidic by adding a base to provide the desired pH, typically of about pH 5 or above. Suitable bases for neutralization of formic acid include, but are not limited to, organic bases, for example amines, alkoxides and the like, and inorganic bases, for example, hydroxide salts (e.g., NaOH), carbonate salts (e.g., $NaHCO_3$), bicarbonate salts (e.g., $K_2CO_3$), basic phosphate salts (e.g., $K_2HPO_4$, $Na_3PO_4$), and the like.

For pH values above about pH 5, at which formate is predominantly present as $HCO_2^-$, Equation (2) below, describes the formate dehydrogenase-catalyzed reduction of NAD+ or NADP+ by formate.

Equation (2)

When formate and formate dehydrogenase are employed as the cofactor regeneration system, the pH of the reaction mixture may be maintained at the desired level by standard buffering techniques, wherein the buffer releases protons up to the buffering capacity provided, or by the addition of an acid concurrent with the course of the conversion. Suitable acids to add during the course of the reaction to maintain the pH include organic acids, for example carboxylic acids, sulfonic acids, phosphonic acids, and the like, mineral acids, for example hydrohalic acids (such as hydrochloric acid), sulfuric acid, phosphoric acid, and the like, acidic salts, for example dihydrogenphosphate salts (e.g., $KH_2PO_4$), bisulfate salts (e.g., $NaHSO_4$) and the like. Some embodiments utilize formic acid, whereby both the formate concentration and the pH of the solution are maintained.

When acid addition is employed to maintain the pH during a reduction reaction using the formate/formate dehydrogenase cofactor regeneration system, the progress of the conversion may be monitored by the amount of acid added to maintain the pH. Typically, acids added to unbuffered or partially buffered reaction mixtures over the course of conversion are added in aqueous solutions.

The terms "secondary alcohol dehydrogenase" and "sADH" are used interchangeably herein to refer to an NAD+ or NADP+-dependent enzyme that catalyzes the conversion of a secondary alcohol and NAD+ or NADP+ to a ketone and NADH or NADPH, respectively. Equation (3), below, describes the reduction of NAD+ or NADP+ by a secondary alcohol, illustrated by isopropanol.

Equation (3)

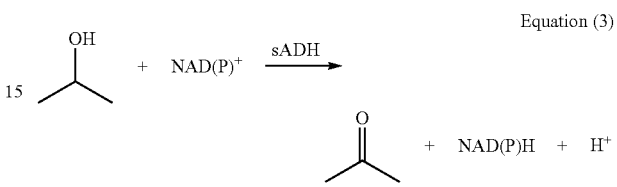

Secondary alcohol dehydrogenases that are suitable for use as cofactor regenerating systems in the ketoreductase-catalyzed reduction reactions described herein include both naturally occurring secondary alcohol dehydrogenases, as well as non-naturally occurring secondary alcohol dehydrogenases. Naturally occurring secondary alcohol dehydrogenases include known alcohol dehydrogenases from, *Thermoanaerobium brockii*, *Rhodococcus etythropolis*, *Lactobacillus kefiri*, *Lactobacillus brevis*, *Lactobacillus minor*, *Novosphingobium aromaticivorans* and non-naturally occurring secondary alcohol dehydrogenases include engineered alcohol dehdyrogenases derived therefrom. Secondary alcohol dehydrogenases employed in the methods described herein, whether naturally occurring or non-naturally occurring, may exhibit an activity of at least about 1 μmol/min/mg, sometimes at least about 10 μmol/min/mg, or at least about $10^2$ μmol/min/mg, up to about $10^3$ μmol/min/mg or higher.

Suitable secondary alcohols include lower secondary alkanols and aryl-alkyl carbinols. Examples of lower secondary alcohols include isopropanol, 2-butanol, 3-methyl-2-butanol, 2-pentanol, 3-pentanol, 3,3-dimethyl-2-butanol, and the like. In one embodiment the secondary alcohol is isopropanol. Suitable aryl-alkyl carbinols include unsubstituted and substituted 1-arylethanols.

When a secondary alcohol and secondary alcohol dehydrogenase are employed as the cofactor regeneration system, the resulting NAD+ or NADP+ is reduced by the coupled oxidation of the secondary alcohol to the ketone by the secondary alcohol dehydrogenase. Some engineered ketoreductases also have activity to dehydrogenate a secondary alcohol reductant. In some embodiments using secondary alcohol as reductant, the engineered ketoreductase and the secondary alcohol dehydrogenase are the same enzyme. Therefore, in certain embodiments, the reactions of the present disclosure are as depicted in Schemes 6 and 7, below:

Scheme 6

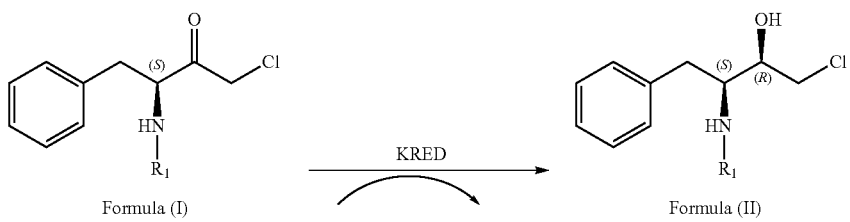

Formula (I)　　　　　　　　　　Formula (II)

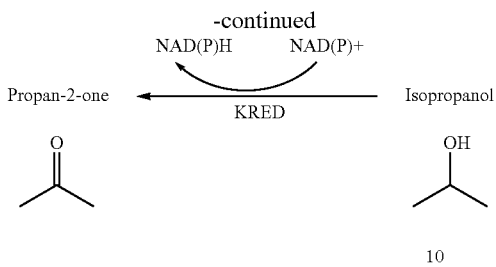

Scheme 7

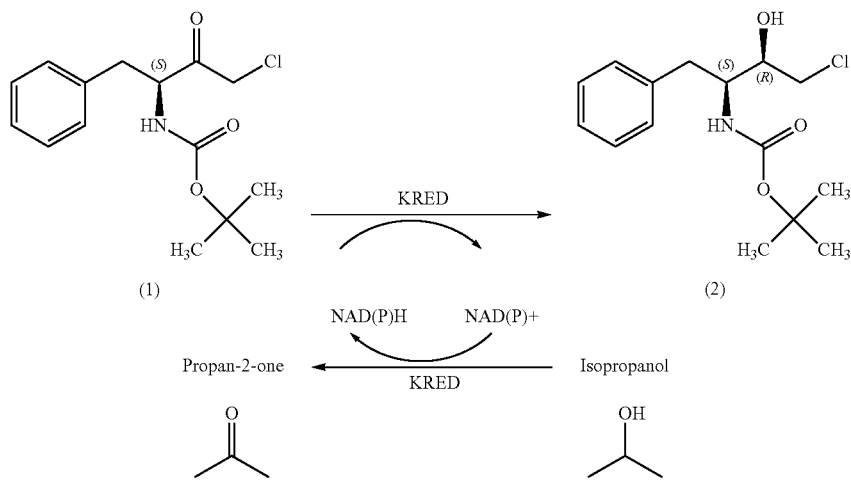

In carrying out embodiments of the ketoreductase-catalyzed reduction reactions described herein employing a cofactor regeneration system, e.g. as depicted in Schemes 6 and 7, the reactions may be run under low pressure and/or increased temperature to effect removal of the propan-2-one product. Such embodiments may further comprise the addition of isopropanol as the reaction proceeds, e.g., by continuous feeding or batch additions.

In carrying out embodiments of the ketoreductase-catalyzed reduction reactions described herein employing a cofactor regeneration system, either the oxidized or reduced form of the cofactor may be provided initially. As described above, the cofactor regeneration system converts oxidized cofactor to its reduced form, which is then utilized in the reduction of the ketoreductase substrate.

In some embodiments, cofactor regeneration systems are not used. For reduction reactions carried out without the use of a cofactor regenerating systems, the cofactor is added to the reaction mixture in reduced form.

In some embodiments, when the process is carried out using whole cells of the host organism, the whole cell may natively provide the cofactor. Alternatively or in combination, the cell may natively or recombinantly provide the glucose dehydrogenase.

In carrying out the stereospecific reduction reactions described herein, the engineered ketoreductase enzyme, and any enzymes comprising the optional cofactor regeneration system, may be added to the reaction mixture in the form of the purified enzymes, whole cells transformed with gene(s) encoding the enzymes, and/or cell extracts and/or lysates of such cells. The gene(s) encoding the engineered ketoreductase enzyme and the optional cofactor regeneration enzymes can be transformed into host cells separately or together into the same host cell. For example, in some embodiments one set of host cells can be transformed with gene(s) encoding the engineered ketoreductase enzyme and another set can be transformed with gene(s) encoding the cofactor regeneration enzymes. Both sets of transformed cells can be utilized together in the reaction mixture in the form of whole cells, or in the form of lysates or extracts derived therefrom. In other embodiments, a host cell can be transformed with gene(s) encoding both the engineered ketoreductase enzyme and the cofactor regeneration enzymes.

Whole cells transformed with gene(s) encoding the engineered ketoreductase enzyme and/or the optional cofactor regeneration enzymes, or cell extracts and/or lysates thereof, may be employed in a variety of different forms, including solid (e.g., lyophilized, spray-dried, and the like) or semisolid (e.g., a crude paste).

The cell extracts or cell lysates may be partially purified by precipitation (ammonium sulfate, polyethyleneimine, heat treatment or the like, followed by a desalting procedure prior to lyophilization (e.g., ultrafiltration, dialysis, and the like). Any of the cell preparations may be stabilized by crosslinking using known crosslinking agents, such as, for example, glutaraldehyde or immobilization to a solid phase (e.g., Eupergit C, and the like).

The solid reactants (e.g., enzyme, salts, etc.) may be provided to the reaction in a variety of different forms, including powder (e.g., lyophilized, spray dried, and the like), solution, emulsion, suspension, and the like. The reactants can be readily lyophilized or spray dried using methods and equipment that are known to those having ordinary skill in the art. For example, the protein solution can be frozen at −80° C. in small aliquots, then added to a pre-chilled lyophilization chamber, followed by the application of a vacuum. After the removal of water from the samples, the temperature is typically raised to 4° C. for two hours before release of the vacuum and retrieval of the lyophilized samples.

The quantities of reactants used in the reduction reaction will generally vary depending on the quantities of product desired, and concomitantly the amount of ketoreductase substrate employed. The following guidelines can be used to determine the amounts of ketoreductase, cofactor, and optional cofactor regeneration system to use. Generally, keto substrates can be employed at a concentration of about 20 g/L to 300 g/L using from about 50 mg/L to about 5 g/L of ketoreductase and about 10 mg to about 150 mg of cofactor. Those having ordinary skill in the art will readily understand how to vary these quantities to tailor them to the desired level of productivity and scale of production. Appropriate quantities of optional cofactor regeneration system may be readily determined by routine experimentation based on the amount of cofactor and/or ketoreductase utilized. In general, the reductant (e.g., glucose, formate, isopropanol) is utilized at levels above the equimolar level of ketoreductase substrate to achieve essentially complete or near complete conversion of the ketoreductase substrate.

The order of addition of reactants is not critical. The reactants may be added together at the same time to a solvent (e.g., monophasic solvent, biphasic aqueous co-solvent system, and the like), or alternatively, some of the reactants may be added separately, and some together at different time points. For example, the cofactor regeneration system, cofactor, ketoreductase, and ketoreductase substrate may be added first to the solvent.

For improved mixing efficiency when an aqueous co-solvent system is used, the cofactor regeneration system, ketoreductase, and cofactor may be added and mixed into the aqueous phase first. The organic phase may then be added and mixed in, followed by addition of the ketoreductase substrate. Alternatively, the ketoreductase substrate may be premixed in the organic phase, prior to addition to the aqueous phase.

Suitable conditions for carrying out the ketoreductase-catalyzed reduction reactions described herein include a wide variety of conditions which can be readily optimized by routine experimentation that includes, but is not limited to, contacting the engineered ketoreductase enzyme and substrate at an experimental pH and temperature and detecting product, for example, using the methods described in the Examples provided herein.

The ketoreductase catalyzed reduction is typically carried out at a temperature within the range of from about 15° C. to about 85° C., from about 20° C. to about 80° C., from about 25° C. to about 75° C., from about 30° C. to about 70° C., from about 35° C. to about 65° C., from about 40° C. to about 60° C., or from about 45° C. to about 55° C. In certain embodiments, the ketoreductase catalyzed reduction is carried out at a temperature of about 45° C.

The reduction reaction is generally allowed to proceed until essentially complete, or nearly complete, conversion of substrate to product is obtained. The reduction of substrate to product can be monitored using known methods by detecting substrate and/or product. Suitable methods include gas chromatography, HPLC, and the like. Conversion yields of the alcohol reduction product generated in the reaction mixture are generally greater than about 50%, may also be greater than about 60%, may also be greater than about 70%, may also be greater than about 80%, may also be greater than about 90%, and are often greater than about 97%, 98%, or even 99%.

Various features and embodiments of the disclosure are illustrated in the following representative examples, which are intended to be illustrative, and not limiting.

6. EXAMPLES

Example 1

Wild-Type Ketoreductase Gene Acquisition and Construction of Expression Vectors

The ketoreductase (KRED) encoding gene from wild-type *Novosphingobium aromaticivorans* (SEQ ID NO:2) was designed for expression in *E. coli* using standard codon optimization. (Standard codon-optimization software is reviewed in e.g., "OPTIMIZER: a web server for optimizing the codon usage of DNA sequences," Puigbò et al., Nucleic Acids Res. 2007 July; 35(Web Server issue): W126-31. Epub 2007 Apr. 16.) Genes were synthesized using oligonucleotides composed of 42 nucleotides and cloned into expression vector pCK110900, which is depicted as FIG. 3 in US Patent Application Publication 20060195947, which is hereby incorporated by reference herein, under the control of a lac promoter. The expression vector also contained the P15a origin of replication and the chloramphenicol resistance gene. Resulting plasmids were transformed into *E. coli* W3110 or *E. coli* BL21 using standard methods.

Polynucleotides encoding the engineered ketoreductase polypeptides of the present disclosure were also cloned into vector pCK110900 for expression in *E. coli* W3110 or *E. coli* BL21. Multiple rounds of directed evolution of the codon-optimized KRED gene were carried out yielding the variant sequences listed in Table 2.

Example 2

Shake-Flask Procedure for Production of Ketoreductase Polypeptides

A single microbial colony of *E. coli* containing a plasmid encoding an engineered ketoreductase of interest was inoculated into 50 mL Luria Bertani broth containing 30 µg/ml chloramphenicol and 1% glucose. Cells were grown overnight (at least 16 hours) in an incubator at 30° C. with shaking at 250 rpm. The culture was diluted into 250 ml Terrific Broth (12 g/L bacto-tryptone, 24 g/L yeast extract, 4 ml/L glycerol, 65 mM potassium phosphate, pH 7.0, 1 mM MgSO4) containing 30 µg/ml chloramphenicol, in a 1 liter flask to an optical density at 600 nm (OD600) of 0.2 and allowed to grow at 30° C. Expression of the ketoreductase gene was induced by addition of isopropyl-β-D-thiogalactoside ("IPTG") to a final concentration of 1 mM when the OD600 of the culture is 0.6 to 0.8 and incubation was then continued overnight (at least 16 hours).

Cells were harvested by centrifugation (5000 rpm, 15 min, 4° C.) and the supernatant discarded. The cell pellet was resuspended with an equal volume of cold (4° C.) 100 mM triethanolamine (chloride) buffer, pH 7.0 (optionally including 2 mM $MgSO_4$), and harvested by centrifugation as above. The washed cells were resuspended in two volumes of the cold triethanolamine (chloride) buffer and passed through a French Press twice at 12,000 psi while maintained at 4° C. Cell debris was removed by centrifugation (9000 rpm, 45 minutes, 4° C.). The clear lysate supernatant was collected and stored at −20° C. Lyophilization of frozen clear lysate provides a dry shake-flask powder of crude ketoreductase

Example 3

Fermentation Procedure for Production of Ketoreductase Polypeptides

Bench-scale fermentations were carried out at 30° C. in an aerated, agitated 15 L fermentor using 6.0 L of growth medium (0.88 g/L ammonium sulfate, 0.98 g/L of sodium citrate; 12.5 g/L of dipotassium hydrogen phosphate trihydrate, 6.25 g/L of potassium dihydrogen phosphate, 6.2 g/L of Tastone-154 yeast extract, 0.083 g/L ferric ammonium citrate, and 8.3 ml/L of a trace element solution containing 2 g/L of calcium chloride dihydrate, 2.2 g/L of zinc sulfate septahydrate, 0.5 g/L manganese sulfate monohydrate, 1 g/L cuprous sulfate heptahydrate, 0.1 g/L ammonium molybdate tetrahydrate and 0.02 g/L sodium tetraborate). The fermentor was inoculated with a late exponential culture of *E. coli* W3110 or *E. coli* BL21 containing the plasmid encoding the engineered ketoreductase gene of interest (grown in a shake flask as described in Example 2) to a starting OD600 of 0.5 to 2.0. The fermentor was agitated at 500-1500 rpm with air supplied to the fermentation vessel at 1.0-15.0 L/minutes to maintain a dissolved oxygen level of 30% saturation or greater. The pH of the culture was maintained at 7.0 by addition of 20% v/v ammonium hydroxide. Growth of the culture was maintained by addition of a feed solution containing 500 g/L cerelose, 12 g/L ammonium chloride and 10.4 g/L magnesium sulfate heptahydrate. After the culture reached an OD600 of 50, expression of ketoreductase was induced by addition of isopropyl-β-D-thiogalactoside (IPTG) to a final concentration of 1 mM and fermentation continued for another 14 hours. The culture was then chilled to 4° C. and maintained at that temperature until harvested. Cells were collected by centrifugation at 5000 G for 40 minutes at 4° C. Harvested cells were used directly in the following downstream recovery process or were stored at 4° C. or frozen at −80° C. until such use.

The cell pellet was resuspended in 2 volumes of 100 mM triethanolamine (chloride) buffer, pH 6.8, at 4° C. to each volume of wet cell paste. The intracellular ketoreductase was released from the cells by passing the suspension through a homogenizer fitted with a two-stage homogenizing valve assembly using a pressure of 12000 psig. The cell homogenate was cooled to 4° C. immediately after disruption. A solution of 10% w/v polyethyleneimine, pH 7.2, was added to the lysate to a final concentration of 0.5% w/v and stirred for 30 minutes. The resulting suspension was clarified by centrifugation at 5000G in a standard laboratory centrifuge for 30 minutes. The clear supernatant was decanted and concentrated ten-fold using a cellulose ultrafiltration membrane with a molecular weight cut off of 30 kD. The final concentrate was dispensed into shallow containers, frozen at −20° C. and lyophilized to a powder. The crude ketoreductase polypeptide powder is stored at −80° C.

Example 4

Determination of Percent Conversion and Diastereomeric Purity for ketoreductase catalyzed reduction of compound (1) ((S)-tert-butyl 4-chloro-3-oxo-1-phenylbutan-2-ylcarbamate) to the corresponding alcohol, compound (2) (tert-butyl(2S,3R)-4-chloro-3-hydroxy-1-phenylbutan-2-ylcarbamate)

The conversion rate ketoreductase catalyzed stereoselective reduction of compound (1) ((S)-tert-butyl 4-chloro-3-oxo-1-phenylbutan-2-ylcarbamate) to the corresponding alcohol, compound (2) (tert-butyl(2S,3R)-4-chloro-3-hydroxy-1-phenylbutan-2-ylcarbamate) was determined by sampling enzymatic reaction mixtures at time intervals (e.g., at hours 0.5, 2, 4, 7, 9, and 24) using an Agilent 1200 HPLC equipped with an Agilent XDB C18 (15 cm length, 4.6 mm diameter), using 60% MeCN, 40% water (isocratic) as eluent at a flow 1.8 ml/min; and a column temperature 25° C. Compound (1) retention time: 3.119 minutes; compound (2) retention time: 2.378 minutes. The amounts of substrate (compound (1)) and product (compound (2)) were determined based HPLC peak areas detected at 210 nm.

Diastereopurity of the product of the ketoreductase polypeptide catalyzed reaction, compound (2) (tert-butyl(2S, 3R)-4-chloro-3-hydroxy-1-phenylbutan-2-ylcarbamate) was determined using an Agilent 1200 HPLC equipped with Agilent XDB C18 (15 cm length, 4.6 mm diameter) using 50% MeCN, 50% water (isocratic) as the eluent at a flow rate of 1.50 mL/min at a temperature of 20° C. Desired diastereomer of compound (2) retention time: 5.083 min; and undesired diastereomer (and substrate) retention time: 4.050 min.

Example 5

Prescreen for Engineered Ketoreductase Polypeptides Capable of Reducing Isopropanol in the Presence of NADP⁺ to Yield NADPH and Acetone This example illustrates a prescreening assay used to identify variant genes encoding ketoreductases capable of reducing isopropanol in the presence of NADP$^+$ to produce acetone and NADPH. An *E. coli* colony containing a plasmid encoding an engineered ketoreductase was picked using a Q-Bot® robotic colony picker (Genetix USA, Inc., Boston, Mass.) into 96-well shallow well microtiter plates containing 180 μL Terrific Broth (TB), 1% glucose and 30 μg/mL chloramphenicol (CAM). Cells were grown overnight at 30° C. with shaking at 200 rpm. A 10 μL aliquot of this culture was then transferred into 96-deep well plates containing 390 μL Terrific Broth (TB), 1 mM MgSO$_4$ and 30 μg/mL CAM. After incubation of the deep-well plates at 30° C. with shaking at 250 rpm for 2 to 3 hours, recombinant gene expression within the cultured cells was induced by addition of IPTG to a final concentration of 1 mM. The plates were then incubated at 30° C. with shaking at 250 rpm for 18 hours.

Cells were pelleted by centrifugation (4000 RPM, 10 minutes, 4° C.), resuspended in 400 μL lysis buffer and lysed by shaking at room temperature for 2 hours. The lysis buffer contains 100 mM triethanolamine (chloride) buffer, pH 7, 1 mg/mL lysozyme, 500 μg/mL polymixin B sulfate ("PMBS") and 1 mM MgSO$_4$. After sealing with aluminum/polypropylene laminate heat seal tape (Velocity 11 (Menlo Park, Calif.), Cat#06643-001), the plates were shaken vigorously for 2 hours at room temperature. Cell debris was collected by centrifugation (4000 RPM, 10 minutes, 4° C.) and the clear supernatant was assayed directly or stored at 4° C. until use.

In this assay, 20 μl of sample (diluted in 100 mM triethanolamine(chloride) buffer, at the same pH as the lysis buffer, and 1 mM MgSO$_4$) was added to 180 μl of an assay mixture in a well of 96-well black microtiter plates. Assay buffer consists of 100 mM triethanolamine (chloride) buffer, pH 7, 50% isopropyl alcohol (IPA), 1 mM MgSO$_4$ and 222 μM NADP$^+$. The reaction was followed by measuring the reduction in fluorescence of NADP$^+$ as it is converted to NADPH using a Flexstation® instrument (Molecular Devices, Sunnyvale, Calif.). NADPH fluorescence was measured at 445 nm upon excitation at 330 nm. If desired, samples of lysates can be preincubated at 25-40° C. in the presence or absence of 50% IPA prior to addition to the assay mixture.

Example 6

Screening for Engineered Ketoreductase Polypeptides Capable of stereoselective conversion of the substrate, compound (1) ((S)-tert-butyl 4-chloro-3-oxo-1-phenylbutan-2-ylcarbamate) to the corresponding product, compound (2) (tert-butyl(2S,3R)-4-chloro-3-hydroxy-1-phenylbutan-2-ylcarbamate)

The codon-optimized ketoreductase gene of derived from *Novosphingobium aromaticivorans* (SEQ ID NO: 1) constructed as in Example 1, was submitted to mutagenesis using directed evolution methods described above and the population of mutant DNA molecules were transformed into a suitable *E. coli* host strain. Antibiotic resistant transformants were selected and processed to identify those expressing a ketoreductase having an improved ability to convert compound (1) to compound (2).

Cell selection, growth, induction of the variant ketoreductase genes and collection of cell pellets were as described in Example 5. Cell pellets were lysed by addition of 400 μL lysis buffer (1 mM MgSO$_4$, 0.5 mg/ml polymyxin B sulfate ("PMBS"), 1 mg/ml lysozyme, 100 mM triethanolamine (pH ~6), and 1 mg/mL NADP$^+$) to each well. The plates were sealed, shaken vigorously for two hours at room temperature, and then centrifuged at 4000 rpm for 10 minutes at 4° C. The supernatants was recovered and stored at 4° C. until use.

Enzymatic Reduction Assay: An aliquot (450 μL) of a mixture of isopropanol and solid substrate ((S)-tert-butyl 4-chloro-3-oxo-1-phenylbutan-2-ylcarbamate) was added to each well of a Costar® deep well plate using a Multidrop instrument (MTX Lab Systems, Vienna Va.), followed by robotic addition of 50 μL of the recovered lysate supernatant using a Multimek™ instrument (Multimek, Inc., Santa Clara Calif.), to provide a reaction comprising 10 mg/ml substrate (S)-tert-butyl 4-chloro-3-oxo-1-phenylbutan-2-ylcarbamate, 0.1 mg/ml NADP$^+$, 10 mM triethanolamine pH ~6, and 10% isopropanol (v/v). The plates were heat sealed with aluminum/polypropylene laminate heat seal tape (Velocity 11 (Menlo Park, Calif.), Cat#06643-001) at 170° C. for 2.5 seconds and then shaken overnight (at least 16 hours) at ambient temperature. Reactions were quenched by the addition of 1 ml of methyl-t-butyl ether (MTBE). Plates were resealed, shaken for 5 minutes, and then centrifuged at 4000 rpm for 10 minutes. A 250 μL aliquot of the cleared reaction mixture was transferred to a new shallow well polypropylene plate (Costar #3365), which was sealed, after which the extracts are subjected to HPLC analysis using methods described above (e.g., see Example 4).

High-throughput Screening Assay at pH ~6 and 10% IPA (v/v): 50 μl of cell lysate containing 1 g/L NADP$^+$ was transferred to a deep well plate (Costar #3960) containing 450 μl of an assay mix (per 100 ml assay mix: 5 ml 100 mM triethanolamine (chloride) (pH 7), 13.4 g (S)-tert-butyl 4-chloro-3-oxo-1-phenylbutan-2-ylcarbamate, and 10 ml isopropyl alcohol). After sealing the plates, reactions were run for at least 16 hours at ambient temperature. Reactions were quenched by the addition of 1 ml of 95% MTBE, and the plates sealed with aluminum/polypropylene laminate heat seal tape (Velocity 11 (Menlo Park, Calif.), Cat#06643-001), shaken for 5-10 min, and centrifuged at 4000 rpm for 10 minutes. A 250 μL aliquot of the cleared reaction mixture was transferred to a new shallow well polypropylene plate (Costar #3365), which was then sealed. The extracts prepared in this manner were subjected to HPLC analysis as described above.

Engineered ketoreductase polypeptides capable of converting (S)-tert-butyl 4-chloro-3-oxo-1-phenylbutan-2-ylcarbamate to tert-butyl(2S,3R)-4-chloro-3-hydroxy-1-phenylbutan-2-ylcarbamate with high conversion rate (e.g., at least about 70-95% in 24 hours) and high diastereomeric purity (e.g., at least about 85-99% d.e.) were identified using the procedures disclosed above. Multiple iterations of these procedures were carried out in which one or more engineered ketoreductase gene with improved properties were isolated from one round of mutagenesis and used as the starting material for subsequent rounds of mutagenesis and screening. Some of the improved engineered ketoreductases resulting from these multiple rounds of directed evolution are disclosed herein and listed in Table 2.

Example 7

Stereoselective reduction of (S)-tert-butyl 4-chloro-3-oxo-1-phenylbutan-2-ylcarbamate, compound (1), using isopropyl alcohol for co-factor regeneration by engineered ketoreductases derived from *Novosphingobium aromaticivorans*

Engineered ketoreductase enzymes derived from *Novosphingobium aromaticivorans* as described above were assayed for use in a preparative scale reduction of (S)-tert-butyl 4-chloro-3-oxo-1-phenylbutan-2-ylcarbamate as follows. A 100 μL solution of the engineered ketoreductase to be tested (10 mg/mL) and NADP-Na (1 mg/mL) in 100 mM triethanolamine(chloride) buffer pH 7 were combined in a 5 mL reaction vial equipped with a magnetic stir bar. Subsequently, 85 μL of isopropyl alcohol ("IPA") was added to the enzyme/NADP-Na solution, followed by 120 mg of compound (1). The reaction was stirred at ambient temperature and conversion of the compound (1) to compound (2) was monitored by HPLC analysis of samples taken periodically over a 24 hour period from the reaction using analytical methods disclosed in Example 4.

Table 2 identifies the ketoreductase variants (by polynucleotide and polypeptide SEQ ID NO), the amino acid mutations relative to wild-type ketoreductase polypeptide of SEQ ID NO:2, and the relative activity of each variant, relative to the activity of the wild-type enzyme having the amino acid sequence of SEQ ID NO: 2. As shown by the results listed in Table 2, nearly all of the engineered ketoreductases have at least 120% (i.e., 1.2-fold or greater) of the activity of the wild-type polypeptide activity, and several of the engineered ketoreductases (e.g., polypeptides of SEQ ID NOs: 6, 50, 52, 56) have mutations resulting in improved activity at least 300% greater (i.e., 3-fold or greater) than that of SEQ ID NO: 2. These results illustrate that engineered ketoreductases derived from the ketoreductase *Novosphingobium aromaticivorans* disclosed herein provide improved activities compared to the wild-type ketoreductase of SEQ ID NO:2 for the reduction of compounds of Formula (I) such as compound (1).

Example 8

Use of Engineered Ketoreductases in a Stereoselective Preparative Scale Conversion of Compound (1) to Compound (2), and Compound (2) to Compound (3)

A 1 L jacketed process reactor, equipped with over head stirrer, baffle and internal thermometer was charged sequentially with 90.0 g of compound (1), 400 ml of a 100 mM triethanolamine solution (pH 9.0), 60 ml IPA and NAD⁺ (300 mg). The resulting slurry was stirred for 10 min and 600 mg of the engineered ketoreductase polypeptide of SEQ ID NO: 6 was added. The reaction mixture was heated to 45° C. and stirred at 150 rpm for the first 4 hours and at 250 rpm afterwards. In-process HPLC analysis to determine conversion of compound (1) to compound (2) was carried out on the reaction (as described in Example 4). After in-process analysis indicated 99.8% conversion (at 9 hours) the reaction was cooled to 20° C.

MTBE (600 mL) was added to the reaction slurry and agitated at 250 rpm for 50 min. Phases were allowed to separate and the aqueous layer removed. The MTBE phase was collected separately. The aqueous layer was recharged and MTBE (300 mL) added. The biphasic mixture was agitated for 250 rpm for 45 min. The phases were allowed to separate and the aqueous layer removed. HPLC analysis of the aqueous phase (as described for determining conversion in Example 4) indicated that >99% of the product had been removed. The combined MTBE layers were filtered through a pad of celite (30 g), the filter cake was washed with 90 mL MTBE, and the unified MTBE phases washed with 90 mL water at 250 rpm for 15 min. The phases were allowed to separate and the aqueous phase removed. The purity of the desired product compound (2) was determined to be 98.4% according to HPLC.

KOH (39.7 g, 85% w/w) was added to the organic phase containing compound (2) and stirred at 250 rpm and 25° C. After in-process HPLC analysis indicated >99.9% conversion (at 8 hours) 180 ml of water was added and the biphasic mixture stirred for 30 min at 250 rpm. The phases were allowed to separate and the aqueous phase removed. The wash was repeated twice with water (90 mL and 180 mL). The remaining MTBE phase (1 L) was concentrated to 400 mL and then 600 ml of n-heptane was added. The resulting mixture was concentrated again to 400 mL using a jacket temperature of 50° C. while incrementally reducing the pressure to 105 Torr. This procedure was repeated once. GC analysis of the remaining n-heptane layer indicates that ≤0.7% MTBE remained and n-heptane was added to give an overall volume of 1 L. The solution was stirred at 120 rpm and the temperature of the solution adjusted to 20° C. The solution was seeded with 20 mg of pure compound (3) and stirred for 1 hour. The temperature was gradually reduced in 0.5° c. steps over 150 min to 17.5° C. After 1 hour of additional stirring crystal formation was observed. The resulting more viscous solution was stirred at 400 rpm and the temperature reduced to 0° C. and stirred for 30 min. The reactor was drained and the white mass filtered under reduced pressure, washed with cold n-heptane (2×180 ml) and dried at approx 20 mm Hg for 24 hours. This provided 64.4 g (81% yield) of compound (3), tert-butyl(S)-1-((R)-oxiran-2-yl)-2-phenylethylcarbamate, in a single crop as a white solid with chemical purity of 98.9% and diastereomeric purity of >99.9% de. The balance of the yield was in the mother liquors and could be isolated as a second crop to provide a near quantitative total yield of approximately 98-99%. It is reasonable to expect that a modified crystallization process can lead to nearly quantitative single crop yields of the pure product of compound (3).

All publications, patents, patent applications and other documents cited in this application are hereby incorporated by reference in their entireties for all purposes to the same extent as if each individual publication, patent, patent application or other document were individually indicated to be incorporated by reference for all purposes.

While various specific embodiments have been illustrated and described, it will be appreciated that various changes can be made without departing from the spirit and scope of the invention(s).

What is claimed is:

1. A recombinant polynucleotide encoding an engineered ketoreductase polypeptide capable of converting (S)-tert-butyl 4-chloro-3-oxo-1-phenylbutan-2-ylcarbamate to tert-butyl (2S,3R)-4-chloro-3-hydroxy-1-phenylbutan-2-ylcarbamate with a relative activity at least 1.2-fold that of the polypeptide of SEQ ID NO:2, wherein the engineered ketoreductase polypeptide comprises an amino acid sequence at least 90% identical to SEQ ID NO:2 and includes one or more amino acid substitutions relative to SEQ ID NO:2, selected from the group consisting of: P2L; V28A; A34S;
A47V; E50K; D81N; S90V; I91L; I91W; I91R; I91K; K94R; D112Y; G117D; S143R; V144T;
G145A; R148H; A150G; F152L; N153G; N153V; N153H; T158S; G190A; S198N; I199M;
I199L; I199N; M200I; A217T; I225V; P231F; A232V; E233Q; D244G; F260Y; and S261N.

2. The polynucleotide of claim 1, wherein said engineered ketoreductase polypeptide comprises an amino acid sequence selected from the group consisting of SEQ ID NO: 6, 4, 14, 16, 18, 20, 22, 24, 26, 28, 30, 32, 34, 36, 38, 40, 50, 52, 54, 56, 60, 62, 65, 66, 68, 70, 72, 74, 76, 78, and 80.

3. The polynucleotide of claim 1, wherein said engineered ketoreductase polypeptide wherein the relative activity of said engineered ketoreductase polypeptide is at least 1.5-fold that of the polypeptide of SEQ ID NO: 2 and the engineered ketoreductase polypeptide comprises an amino acid sequence selected from the group consisting of SEQ ID NO: 6, 18, 22, 30, 38, 40, 50, 52, 54, and 56.

4. The polynucleotide of claim 1, wherein the amino acid sequence of said engineered ketoreductase polypeptide comprises at least one of the following substitutions: I91L; I91W; I91R; I91K; V144T; G145A; A150G; N153G; N153V; N153H; G190A; I199M; I199L; I199N; and F260Y, wherein the substitutions are relative to SEQ ID NO:2.

5. The polynucleotide of claim 1, wherein the amino acid sequence of said engineered ketoreductase polypeptide comprises at least one of the following substitutions: I91R;

G145A; N153G; N153V; N153H; G190A; and F260Y, wherein the substitutions are relative to SEQ ID NO:2.

6. The polynucleotide of claim 1, wherein the relative activity of said engineered ketoreductase polypeptide is at least 3-fold that of the polypeptide of SEQ ID NO:2, and wherein the engineered ketoreductase polypeptide sequence comprises the substitution G145A, wherein the sequence is relative to SEQ ID NO:2.

7. The polynucleotide of claim 1, wherein said engineered ketoreductase_polypeptide is capable of converting a reaction mixture comprising an initial concentration of at least 10 g/L (S)-tert-butyl 4-chloro-3-oxo-1-phenylbutan-2-ylcarbamate to tert-butyl(2S,3R)-4-chloro-3-hydroxy-1-phenylbutan-2-ylcarbamate in at least 97% diastereomeric excess with a conversion rate of at least 70% in 24 hours.

8. An expression vector comprising the polynucleotide of claim 1, operably linked to control sequences capable of directing expression of the encoded polypeptide in a host cell.

9. The expression vector of claim 8, wherein the control sequences comprises a secretion signal.

10. An host cell comprising the expression vector of claim 8.

11. The host cell of claim 10, wherein codons of the polynucleotide encoding the engineered ketoreductase have been optimized for expression in the host cell.

12. The host cell of claim 11, wherein said host cell is *E. coli*.

13. A method for producing an engineered ketoreductase encoded by the polynucleotide of Claim 1, wherein said method comprises culturing a host cell transformed with an expression Vector comprising the polynucleotide of claim 1 under conditions such that said polynucleotide is expressed and said engineered ketoreductase is produced.

14. The method of claim 13, wherein said engineered ketoreductase polypeptide is isolated from said host cell.

* * * * *

UNITED STATES PATENT AND TRADEMARK OFFICE
CERTIFICATE OF CORRECTION

PATENT NO. : 9,029,112 B2
APPLICATION NO. : 14/313465
DATED : May 12, 2015
INVENTOR(S) : Bong et al.

Page 1 of 1

It is certified that error appears in the above-identified patent and that said Letters Patent is hereby corrected as shown below:

In the Claims

In Column 170, Claim 10, line 3, please replace "An host cell" with "An isolated host cell".

Signed and Sealed this
Twentieth Day of October, 2015

Michelle K. Lee
*Director of the United States Patent and Trademark Office*